US011584961B2

(12) United States Patent
Howell et al.

(10) Patent No.: US 11,584,961 B2
(45) Date of Patent: Feb. 21, 2023

(54) BIOMARKERS FOR INFLAMMATORY SKIN DISEASE

(71) Applicant: Incyte Corporation, Wilmington, DE (US)

(72) Inventors: Michael D. Howell, Kennett Square, PA (US); Huiqing Liu, Berwyn, PA (US)

(73) Assignee: Incyte Corporation, Wilmington, DE (US)

( * ) Notice: Subject to any disclaimer, the term of this patent is extended or adjusted under 35 U.S.C. 154(b) by 283 days.

(21) Appl. No.: 16/369,724

(22) Filed: Mar. 29, 2019

(65) Prior Publication Data

US 2020/0063188 A1    Feb. 27, 2020

Related U.S. Application Data

(60) Provisional application No. 62/650,636, filed on Mar. 30, 2018.

(51) Int. Cl.
| | |
|---|---|
| *C12Q 1/68* | (2018.01) |
| *C12Q 1/686* | (2018.01) |
| *G16H 50/30* | (2018.01) |
| *G16B 40/10* | (2019.01) |
| *C12Q 1/6883* | (2018.01) |

(52) U.S. Cl.
CPC ........... *C12Q 1/686* (2013.01); *C12Q 1/6883* (2013.01); *G16B 40/10* (2019.02); *G16H 50/30* (2018.01); *C12Q 2600/106* (2013.01); *C12Q 2600/112* (2013.01); *C12Q 2600/118* (2013.01); *C12Q 2600/158* (2013.01)

(58) Field of Classification Search
CPC ...................................................... C12Q 1/68
See application file for complete search history.

(56) References Cited

U.S. PATENT DOCUMENTS

| | | |
|---|---|---|
| 6,812,341 B1 | 11/2004 | Conrad et al. |
| 7,101,663 B2 | 9/2006 | Godfrey |
| 7,335,667 B2 | 2/2008 | Rodgers et al. |
| 7,598,257 B2 | 10/2009 | Rodgers et al. |
| 7,834,022 B2 | 11/2010 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,486,902 B2 | 7/2013 | Rodgers et al. |
| 8,513,270 B2 | 8/2013 | Arvanitis et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,765,734 B2 | 7/2014 | Huang et al. |
| 8,933,085 B2 | 1/2015 | Rodgers et al. |
| 8,987,443 B2 | 3/2015 | Liu et al. |
| 9,034,884 B2 | 5/2015 | Rodgers et al. |
| 9,181,271 B2 | 11/2015 | Li et al. |
| 9,193,733 B2 | 11/2015 | Rodgers et al. |
| 9,249,145 B2 | 2/2016 | Rodgers et al. |
| 9,249,149 B2 | 2/2016 | Silverman et al. |
| 9,358,229 B2 | 6/2016 | Vannucchi et al. |
| 9,359,358 B2 | 6/2016 | Rodgers et al. |
| 9,382,231 B2 | 7/2016 | Li et al. |
| 9,487,521 B2 | 11/2016 | Zhou et al. |
| 9,498,467 B2 | 11/2016 | Leopold et al. |
| 9,540,367 B2 | 1/2017 | Tung et al. |
| 9,655,854 B2 | 5/2017 | Yeleswaram et al. |
| 9,802,957 B2 | 10/2017 | Zhou et al. |
| 9,993,480 B2 | 6/2018 | Vannucchi et al. |
| 10,166,191 B2 | 1/2019 | Ni et al. |
| 11,324,749 B2 | 5/2022 | Assad |
| 2004/0086915 A1 | 5/2004 | Lin et al. |
| 2006/0106020 A1 | 5/2006 | Rodgers et al. |
| 2010/0113416 A1 | 5/2010 | Friedman et al. |
| 2010/0298334 A1 | 11/2010 | Rodgers et al. |
| 2011/0059951 A1 | 3/2011 | Rodgers et al. |
| 2011/0207754 A1 | 8/2011 | Li et al. |
| 2011/0224190 A1 | 9/2011 | Huang et al. |
| 2011/0288107 A1 | 11/2011 | Parikh et al. |
| 2012/0149681 A1 | 6/2012 | Rodgers et al. |
| 2012/0149682 A1 | 6/2012 | Rodgers et al. |
| 2013/0018034 A1 | 1/2013 | Yao et al. |
| 2013/0045963 A1 | 2/2013 | Rodgers et al. |
| 2013/0060026 A1 | 3/2013 | Zhou et al. |

(Continued)

FOREIGN PATENT DOCUMENTS

| | | |
|---|---|---|
| EP | 0543942 | 6/1993 |
| WO | 03037347 A1 | 5/2003 |

(Continued)

OTHER PUBLICATIONS

Speeckaert et al., The many faces of interleukin-17 in inflammatory skin disease, (2016) British J Derm 175: 892-901 (Year: 2016).*
Musumeci et al., "An update on JAK inhibitors", (2019) Current Medicinal Chemistry, vol. 26, 1806-1832. (Year: 2019).*
Nomura et al; J Allergy Clin Immunol; 2003; 112; 1195-1202.*
Punwany et al; J Am Acad Dermatol, 2012; 67; 658-664.*
Mee et al; The American Journal of Pathology, vol. 171, 2007, pp. 32-42.*
Rothstein et al., "Treatment of vitiligo with the topical Janus kinase inhibitor ruxolitinib", The American Academy of Dermatology, vol. 76, No. 6, pp. 1054-1060, Apr. 5, 2017.
Craiglow BG, King BA. Tofacitinib citrate for the treatment of vitiligo: a pathogenesis-directed Therapy. JAMA Dermatol 2015; 151: 1110-1112.

(Continued)

*Primary Examiner* — Jehanne S Sitton
(74) *Attorney, Agent, or Firm* — Fish & Richardson P.C.

(57) ABSTRACT

Biomarkers are provided that are predictive of a subject's responsiveness to a therapy comprising a JAK inhibitor. The biomarkers, compositions, and methods described herein are useful in selecting appropriate treatment modalities for a subject having, suspected of having, or at risk of developing an inflammatory skin disease.

36 Claims, No Drawings

(56) References Cited

U.S. PATENT DOCUMENTS

| | | |
|---|---|---|
| 2014/0005166 A1 | 1/2014 | Rodgers et al. |
| 2014/0121198 A1 | 5/2014 | Li et al. |
| 2014/0256941 A1 | 9/2014 | Liu et al. |
| 2014/0343030 A1 | 11/2014 | Li et al. |
| 2015/0065447 A1 | 3/2015 | Yeleswaram et al. |
| 2015/0246046 A1 | 9/2015 | Vaddi |
| 2015/0250790 A1 | 9/2015 | Parikh et al. |
| 2015/0344497 A1 | 12/2015 | Zhou et al. |
| 2019/0175578 A1 | 6/2019 | Koblish et al. |
| 2019/0233392 A1 | 8/2019 | Wang et al. |
| 2019/0255053 A1 | 8/2019 | Montgomery et al. |
| 2019/0328739 A1 | 10/2019 | Howell et al. |
| 2019/0331697 A1 | 10/2019 | Howell et al. |
| 2020/0197399 A1 | 6/2020 | Yeleswaram et al. |

FOREIGN PATENT DOCUMENTS

| | | |
|---|---|---|
| WO | 03099771 A2 | 12/2003 |
| WO | 04046120 A2 | 6/2004 |

OTHER PUBLICATIONS

Frisoli ML, Harris JE., Vitiligo: mechanistic insights lead to novel treatments. J. Allergy Clin Immunol 2017; 140: 354-662.

Atzrodt et al., "The Renaissance of H/D Exchange," Chem. Int. Ed., Oct. 4, 2007, 46:7744-7765.

Ewald et al., "Meta-analysis 1-25 derived atopic dermatitis (MADAD) transcriptome defines a robust AD signature highlighting the involvement of atherosclerosis and lipid metabolism pathways," BMC Medical Genomics, Oct. 12, 2005, 8:60.

Gibson et al., "A Novel Method for Real Time Quantitative RT-PCR," Genome Res., Oct. 1996, 6:995-1001.

Kerekes et al. ,"Aurora Kinase Inhibitors Based on the Imidazo[1,2-a]pyrazine Core: Fluorine and Deuterium Incorporation Improve Oral Absorption and Exposure," J. Med. Chem. Dec. 3, 2010, 54:201-210.

Kvist et al., "Comparison of the 1-25 effects of vitamin D products in a psoriasis plaque test and a murine psoriasis xenograft model," Journal of Translational Medicine, Dec. 17, 2009, 7:107.

PCT International Invitation to pay additional fees, Appln. No. PCT/US2019/024990, dated Jul. 2, 2019, 99 pages.

PCT International Search Report and Written Opinion in International Appln. No. PCT/US2019/024990, dated Aug. 8, 2019, 3 Pages.

PCT International Preliminary Report on Patentability in International Appl. No. PCT/US2019/024990, dated Oct. 6, 2020, 10 pages.

Pineda et al., "Gene 1-25 polymorphisms as predictors of response to biological therapies in psoriasis patients", Pharmacological Research, Aug. 12, 2016, 113:71-80.

Rodrigues et al., "Current and emerging treatments for vitiligo," Journal of the American Academy of Dermatology, Jun. 13, 2017, 77:17-29.

Tintle et al., "Reversal of atopic dermatitis with narrow band UVB phototherapy and biomarkers for therapeutic response," Journal of Allergy and Clinical Immunology, Elsevier, May 6, 2011, 128:583-593.

Xu et al., "Design, synthesis and biological evaluation of deuterated nintedanib for improving pharmacokinetic properties," Journal of Labelled Compounds and Radiopharmaceuticals, May 26, 2015, 58:308-312.

Yassky et al., "Molecular 1-25 signatures order the potency of topically applied anti-inflammatory drugs in patients with atopic dermatitis," Journal of Allergy and Clinical Immunology, Oct. 1, 2017, 140:1032-1042.

Zhang et al., "Quantitative RT-PCR Methods for Evaluating Toxicant-Induced Effects on Steroidogenesis Using the H295R Cell Line," Environ. Sci. Technol, Mar. 2005, 39:2777-2785.

\* cited by examiner

BIOMARKERS FOR INFLAMMATORY SKIN DISEASE

CROSS-REFERENCE TO RELATED APPLICATIONS

This application claims priority to U.S. Provisional Appl. No. 62/650,636, filed Mar. 30, 2018. The content of the prior application is incorporated by reference herein in its entirety.

TECHNICAL FIELD

The present invention relates generally to biomarkers and inflammatory skin disease.

BACKGROUND

Inflammatory skin diseases are triggered and maintained by aberrant responses of the cells of the immune system. Inflammatory skin diseases are generally classified according to the host defense system of the skin implicated in the disease: the barrier; innate immunity; or acquired immunity. The barrier of the skin is composed of the physical barrier and the chemical barrier. Several diseases, such as atopic dermatitis, result from a disorder of these components of the barrier. Diseases of innate immunity can be classified into innate immunodeficiency, innate immunohyperactivity (general or local autoinflammation), and qualitative disorder (general or local innate autoimmunity). Diseases of acquired immunity can be classified into immunodeficiency, immunohyperactivity (allergy), and qualitative disorder (autoimmunity).

Janus kinase (JAK) inhibitors have been developed as agents for the treatment of inflammatory skin diseases. However, as for any therapeutic, JAK inhibitors may not be equally effective in all subjects that have an inflammatory skin disease. There is a need for means of identifying those subjects having an inflammatory skin disease that could most benefit from treatment with a JAK inhibitor.

SUMMARY

The present application is based, at least in part, on the identification of biomarkers that are predictive of an inflammatory skin disease subject's responsiveness to a therapy comprising a JAK inhibitor. The expression level of certain genes (e.g., the genes listed in Table 1 and Table 2) prior to treatment is identified as a useful predictor of responsiveness to a therapy comprising a JAK inhibitor. Thus, the biomarkers and compositions described herein are useful, for example, in identifying, stratifying, and/or selecting a patient or a subset of patients having an inflammatory skin disease that could benefit from treatment with a JAK inhibitor. In addition, the methods described herein are useful, for example, in selecting appropriate treatment modalities (e.g., therapy comprising a JAK inhibitor) for a subject suffering from, suspected of having, or at risk of developing an inflammatory skin disease.

The disclosure features a method of treating a human subject having, suspected of having, or at risk of developing an inflammatory skin disease by administering to the human subject a therapy comprising a JAK inhibitor, wherein the human subject has been previously determined to have (i) a baseline expression level of at least one gene selected from the group consisting of ARHGEF35, BNIP3P5, BZW1P2, C1QTNF3-AMACR, CAMK4, CCL18, CYTH4, IL17C, IL1RL1, KHSRPP1, KRT18P12, LIPE-AS1, MS4A3, MTND4P9, MYCBP2-AS2, PAPPA, PLA2G2D, PTCHD3P2, RPL7L1P3, SP5, TDRD1, TMED7-TICAM2, TNFRSF11B, TNFSF14, TRAV30, TRBV5-6, TRDV2, and WDR11-AS1 in a biological sample obtained from the human subject that is lower than a control, and/or (ii) a baseline expression level of at least one gene selected from the group consisting of ASIC4, C10orf35, C6orf58, CCDC73, CDH15, CLHC1, DZIP1, EDN1, EEF1DP4, EFCAB10, FDPSP7, FSIP2, GDF9, H1FNT, HMGB1P31, HS6ST2, HTR1F, IGHG3, IL1RAPL2, LINC00339, LINC00623, LINC01118, LINC01127, MEF2C-AS1, MPV17L, NKAPPI, PLCZ1, PRSS30P, PTPN5, RBP3, RNASEK-C17orf49, RPS26P15, SNX29P1, SYDE2, TIMD4, TRPC2, UPK3BL, WDR88, and ZNF738 in a biological sample obtained from the human subject that is higher than a control.

In some embodiments, the human subject has been previously determined to have (i) baseline expression levels of the genes CCL18, BZW1P2, and TMED7-TICAM2 in a biological sample obtained from the human subject that are lower than a control, and (ii) baseline expression levels of the genes IL1RAPL2, PRSS30P and HTR1F in a biological sample obtained from the human subject that are higher than a control.

In some embodiments, the human subject has been previously determined to have (i) baseline expression levels of the genes CCL18 and PLA2G2D in a biological sample obtained from the human subject that are lower than a control, and (ii) baseline expression levels of the genes FSIP2, H1FNT, HTR1F, IL1RAPL2, PTPN5, RBP3, and WDR88 in a biological sample obtained from the human subject that are higher than a control.

The disclosure also features a method of treating a human subject having, suspected of having, or at risk of developing an inflammatory skin disease by: providing a biological sample obtained from the human subject; measuring in the biological sample a reduced expression level, as compared to a control, of at least one gene selected from the group consisting of ARHGEF35, BNIP3P5, BZW1P2, C1QTNF3-AMACR, CAMK4, CCL18, CYTH4, IL17C, IL1RL1, KHSRPP1, KRT18P12, LIPE-AS1, MS4A3, MTND4P9, MYCBP2-AS2, PAPPA, PLA2G2D, PTCHD3P2, RPL7L1P3, SP5, TDRD1, TMED7-TICAM2, TNFRSF11B, TNFSF14, TRAV30, TRBV5-6, TRDV2, and WDR11-AS1, and/or an increased expression level, as compared to a control, of at least one gene selected from the group consisting of ASIC4, C10orf35, C6orf58, CCDC73, CDH15, CLHC1, DZIP1, EDN1, EEF1DP4, EFCAB10, FDPSP7, FSIP2, GDF9, H1FNT, HMGB1P31, HS6ST2, HTR1F, IGHG3, IL1RAPL2, LINC00339, LINC00623, LINC01118, LINC01127, MEF2C-AS1, MPV17L, NKAPP1, PLCZ1, PRSS30P, PTPN5, RBP3, RNASEK-C17orf49, RPS26P15, SNX29P1, SYDE2, TIMD4, TRPC2, UPK3BL, WDR88, and ZNF738; and administering a therapy comprising a JAK inhibitor to the human subject.

In some embodiments, the method includes measuring in the biological sample a reduced expression level, as compared to a control, of the genes CCL18, BZW1P2, and TMED7-TICAM2 and increased expression level, as compared to a control, of the genes IL1RAPL2, PRSS30P and HTR1F.

In some embodiments, the method includes measuring in the biological sample a reduced expression level, as compared to a control, of the genes CCL18 and PLA2G2D and increased expression level, as compared to a control, of the genes FSIP2, H1FNT, HTR1F, IL1RAPL2, PTPN5, RBP3, and WDR88.

In some embodiments of the methods described herein, the JAK inhibitor is topically administered to the human subject.

In some embodiments of the methods described herein, a second therapeutic agent is administered to the human subject in combination with the JAK inhibitor. The second therapeutic agent can be, for example, a corticosteroid (e.g., a topical corticosteroid), a Vitamin D analogue, anthralin, a retinoid (e.g., a topical retinoid), a calcineurin inhibitor (e.g., tacrolimus or pimecrolimus), salicylic acid, phototherapy, azathioprine, mycophenolate mofetil, methotrexate, cyclosporine, etanercept, infliximab, adalimumab, ustekinumab, golimumab, rituximab, apremilast, secukinumab, ixekizumab, thioguanine, hydroxyurea, or isotretinoin.

The disclosure also features a method of predicting the response of a human subject having, suspected of having, or at risk of developing an inflammatory skin disease to a therapy comprising a JAK inhibitor by: providing a biological sample obtained from the human subject before administering the therapy comprising the JAK inhibitor; and measuring the expression level of at least one gene selected from the group consisting of ARHGEF35, BNIP3P5, BZW1P2, C1QTNF3-AMACR, CAMK4, CCL18, CYTH4, IL17C, IL1RL1, KHSRPP1, KRT18P12, LIPE-AS1, MS4A3, MTND4P9, MYCBP2-AS2, PAPPA, PLA2G2D, PTCHD3P2, RPL7L1P3, SP5, TDRD1, TMED7-TICAM2, TNFRSF11B, TNFSF14, TRAV30, TRBV5-6, TRDV2, WDR11-AS1, ASIC4, C10orf35, C6orf58, CCDC73, CDH15, CLHC1, DZIP1, EDN1, EEF1DP4, EFCAB10, FDSP7, FSIP2, GDF9, H1FNT, HMGB1P31, HS6ST2, HTR1F, IGHG3, 1L1RAPL2, LINC00339, LINC00623, LINC01118, LINC01127, MEF2C-AS1, MPV17L, NKAPP1, PLCZ1, PRSS30P, PTPN5, RBP3, RNASEK-C17orf49, RPS26P15, SNX29P1, SYDE2, TIMD4, TRPC2, UPK3BL, WDR88, and ZNF738 in the biological sample, wherein a reduced expression level, as compared to a control, of ARHGEF35, BNIP3P5, BZW1P2, C1QTNF3-AMACR, CAMK4, CCL18, CYTH4, IL17C, IL1RL1, KHSRPP1, KRT18P12, LIPE-AS1, MS4A3, MTND4P9, MYCBP2-AS2, PAPPA, PLA2G2D, PTCHD3P2, RPL7L1P3, SP5, TDRD1, TMED7-TICAM2, TNFRSF11B, TNFSF14, TRAV30, TRBV5-6, TRDV2, and/or WDR11-AS1, and/or an increased expression level, as compared to a control, of ASIC4, C10orf35, C6orf58, CCDC73, CDH15, CLHC1, DZIP1, EDN1, EEF1DP4, EFCAB10, FDPSP7, FSIP2, GDF9, H1FNT, HMGB1P31, HS6ST2, HTR1F, IGHG3, IL1RAPL2, LINC00339, LINC00623, LINC01118, LINC01127, MEF2C-AS1, MPV17L, NKAPP1, PLCZ1, PRSS30P, PTPN5, RBP3, RNASEK-C17orf49, RPS26P15, SNX29P1, SYDE2, TIMD4, TRPC2, UPK3BL, WDR88, and/or ZNF738 is predictive that the human subject will respond to the therapy comprising the JAK inhibitor.

In some embodiments, the method includes measuring the expression level of the genes CCL18, BZW1P2, TMED7-TICAM2, IL1RAPL2, PRSS30P, and HTR1F in the biological sample, wherein a reduced expression level, as compared to a control, of CCL18, BZW1P2, and TMED7-TICAM2, and an increased expression level, as compared to a control, of IL1RAPL2, PRSS30P, and HTR1F is predictive that the human subject will respond to the therapy comprising the JAK inhibitor.

In some embodiments, the method includes measuring the expression level of the genes CCL18, PLA2G2D, FSIP2, H1FNT, HTR1F, IL1RAPL2, PTPN5, RBP3, and WDR88 in the biological sample, wherein a reduced expression level, as compared to a control, of CCL18 and PLA2G2D, and an increased expression level, as compared to a control, of FSIP2, H1FNT, HTR1F, IL1RAPL2, PTPN5, RBP3, and WDR88 is predictive that the human subject will respond to the therapy comprising the JAK inhibitor.

In some embodiments of the methods described herein, the control is a pre-established cut-off value.

In some embodiments of the methods described herein, the control is the expression level of the gene in a sample or samples obtained from one or more subjects that have not responded to treatment with the JAK inhibitor.

The disclosure also features a method for measuring the amount of a protein in a sample by: providing a biological sample obtained from a human subject having, suspected of having, or at risk of developing an inflammatory skin disease; and measuring the expression level of at least one gene selected from the group consisting of ARHGEF35, BNIP3P5, BZW1P2, C1QTNF3-AMACR, CAMK4, CCL18, CYTH4, IL17C, IL1RL1, KHSRPP1, KRT18P12, LIPE-AS1, MS4A3, MTND4P9, MYCBP2-AS2, PAPPA, PLA2G2D, PTCHD3P2, RPL7L1P3, SP5, TDRD1, TMED7-TICAM2, TNFRSF11B, TNFSF14, TRAV30, TRBV5-6, TRDV2, WDR11-AS1, ASIC4, C10orf35, C6orf58, CCDC73, CDH15, CLHC1, DZIP1, EDN1, EEF1DP4, EFCAB10, FDPSP7, FSIP2, GDF9, H1FNT, HMGB1P31, HS6ST2, HTR1F, IGHG3, IL1RAPL2, LINC00339, LINC00623, LINC01118, LINC01127, MEF2C-AS1, MPV17L, NKAPP1, PLCZ1, PRSS30P, PTPN5, RBP3, RNASEK-C17orf49, RPS26P15, SNX29P1, SYDE2, TIMD4, TRPC2, UPK3BL, WDR88, and ZNF738 in the biological sample.

In some embodiments, the method includes measuring the expression level of the genes CCL18, BZW1P2, TMED7-TICAM2, IL1RAPL2, PRSS30P, and HTR1F in the biological sample.

In some embodiments, the method includes measuring the expression level of the genes CCL18, PLA2G2D, FSIP2, H1FNT, HTR1F, IL1RAPL2, PTPN5, RBP3, and WDR88 in the biological sample.

In some embodiments of the methods described herein, the expression levels of no more than 20 genes are measured.

In some embodiments of the methods described herein, the expression levels of no more than 10 genes are measured.

In some embodiments of the methods described herein, the biological sample comprises a skin biopsy, e.g., a skin biopsy obtained by use of a non-invasive tape strip, an adhesive patch, a dermal shaving, or microplaned skin.

In some embodiments of the methods described herein, the expression level of the at least one gene is measured by RNA sequencing or quantitative PCR.

In some embodiments of the methods described herein, the JAK inhibitor is ruxolitinib.

In some embodiments of the methods described herein, the JAK inhibitor is itacitinib, 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide or a pharmaceutically acceptable salt thereof, or ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile or a pharmaceutically acceptable salt thereof.

In some embodiments of the methods described herein, the inflammatory skin disease is psoriasis, atopic dermatitis, vitiligo, hidradenitis suppurativa, rosacea, Lichen planus, generalized pustular psoriasis, palmoplantar pustulosis, acne, cutaneous lupus, dermatomyositis, or a skin disease characterized by elevated Th1, Th2, or Th17 signaling.

The term "baseline expression level" of a gene refers to the expression level of a gene in a subject prior to initiation of treatment with a JAK inhibitor.

The term "reduced expression level" means an expression level of the gene being analyzed that is lower than the expression level of that gene in a control. For example, the expression level of the gene being analyzed can be at least 1.5, 2, 3, 4, 5, 6, 7, 8, 9, 10, 20, 25, 50, 75, or 100 times lower, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% lower, than the expression level of that gene in a control.

The term "increased expression level" means an expression level of the gene being analyzed that is higher than the expression level of that gene in a control. For example, the expression level of the gene being analyzed can be at least 1.5, 2, 3, 4, 5, 6, 7, 8, 9, 10, 20, 25, 50, 75, or 100 times higher, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% higher, than the expression level of that gene in a control.

The term "respond to a therapy" means that the subject administered with the therapy shows a positive response to the JAK inhibitor therapy provided.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DETAILED DESCRIPTION

This disclosure provides methods and compositions for treating a subject having, suspected of having, or at risk of developing an inflammatory skin disease with a JAK inhibitor. The disclosure provides predictive biomarkers (e.g., gene expression levels) to identify those subjects having, suspected of having, or at risk of developing an inflammatory skin disease for whom administering a therapy comprising a JAK inhibitor is likely to be effective.

Inflammatory Skin Disease

Inflammatory skin diseases are skin diseases that occur as a result of aberrant responses of the cells of the immune system. Examples of inflammatory skin diseases that can be treated with a JAK inhibitor include psoriasis and atopic dermatitis.

Psoriasis causes fast growth of skin cells and is marked by raised, scaly, itchy, dry, and red skin patches. There are five types of psoriasis: plaque psoriasis; pustular psoriasis; guttate psoriasis; inverse psoriasis; and erythrodermic psoriasis. Mild psoriasis is when less than three percent of the body surface area is affected. Moderate psoriasis is when three to ten percent of the body surface area is affected. Severe psoriasis is when greater than ten percent of the body surface area is affected. Mild to moderate plaque psoriasis is when plaques cover less than five percent of the body surface area. Moderate to severe plaque psoriasis is when plaques cover five percent or more of the body surface area.

Atopic dermatitis, also known as atopic eczema, is a chronic, pruritic inflammatory skin disease, which often appears as a red, itchy rash on the cheeks, arms and/or legs.

Additional examples of inflammatory skin diseases that can be treated with a JAK inhibitor include conditions such as vitiligo, hidradenitis suppurativa, rosacea, Lichen planus, generalized pustular psoriasis, palmoplantar pustulosis, acne, cutaneous lupus, dermatomyositis, and a skin disease characterized by elevated Th1, Th2, or Th17 signaling.

Methods of Predicting Responsiveness to a Therapy Comprising a JAK Inhibitor

Several genes have been identified in the Examples whose expression levels are useful in predicting responsiveness (e.g., improvement in skin disease scores and/or disease resolution) of a subject having an inflammatory skin disease to a therapy comprising a JAK inhibitor. These genes, as identified by gene symbols, gene names, and UniProtKB Accession Number, are listed in Tables 1 and 2.

TABLE 1

Biomarkers Exhibiting Reduced Expression in Inflammatory Skin Disease Subjects that Respond to Treatment with a JAK inhibitor as Compared to Control Subjects that do not Respond

| Gene Name | Full Gene Name | UniProtKB Accession Number |
| --- | --- | --- |
| ARHGEF35 | Rho guanine nucleotide exchange factor 35 | A5YM69 |
| BNIP3P5 | BCL2 Interacting Protein 3 Pseudogene 5 | (pseudogene) |
| BZW1P2 | Basic Leucine Zipper And W2 Domains 1 Pseudogene 2 | (pseudogene) |
| C1QTNF3-AMACR | C1QTNF3-AMACR readthrough | E9PGA6 |
| CAMK4 | Calcium/calmodulin-dependent protein kinase type IV | Q16566 |
| CCL18 | C-C motif chemokine 18 | P55774 |
| CYTH4 | Cytohesin-4 | Q9UIA0 |
| IL17C | Interleukin-17C | Q9P0M4 |
| IL1RL1 | Interleukin-1 receptor-like 1 | Q01638 |
| KHSRPP1 | KH-Type Splicing Regulatory Protein Pseudogene 1 | (pseudogene) |
| KRT18P12 | Keratin 18 Pseudogene 12 | (pseudogene) |
| LIPE-AS1 | LIPE Antisense RNA 1 | (RNA Gene) |
| MS4A3 | Membrane-spanning 4-domains subfamily A member 3 | Q96HJ5 |
| MTND4P9 | Mitochondrially Encoded NADH:Ubiquinone Oxidoreductase Core Subunit 4 Pseudogene 9 | (pseudogene) |
| MYCBP2-AS2 | MYCBP2 Antisense RNA 2 | (RNA Gene) |
| PAPPA | Pappalysin-1 | Q13219 |
| PLA2G2D | Group IID secretory phospholipase A2 | Q9UNK4 |
| PTCHD3P2 | patched domain containing 3 pseudogene 2 | (pseudogene) |
| RPL7L1P3 | Ribosomal Protein L7 Like 1 Pseudogene 3 | (pseudogene) |
| SP5 | Transcription factor Sp5 | Q6BEB4 |
| TDRD1 | Tudor domain-containing protein 1 | Q9BXT4 |
| TMED7-TICAM2 | TMED7-TICAM2 | A0A0A6YYA0 |
| TNFRSF11B | Tumor necrosis factor receptor superfamily member 11B | O00300 |

TABLE 1-continued

Biomarkers Exhibiting Reduced Expression in Inflammatory Skin Disease Subjects that Respond to Treatment with a JAK inhibitor as Compared to Control Subjects that do not Respond

| Gene Name | Full Gene Name | UniProtKB Accession Number |
|---|---|---|
| TNFSF14 | Tumor necrosis factor ligand superfamily member 14 | O43557 |
| TRAV30 | T-Cell Receptor Alpha Variable 30 | |
| TCRBV5S2 (TRBV5-6) | T-cell receptor beta variable 5-6 | A0A599 |
| TRDV2 | HDV102S1 | A0JD36 |
| WDR11-AS1 | WDR11 Antisense RNA 1 | (RNA Gene) |

TABLE 2

Biomarkers Exhibiting Increased Expression in Inflammatory Skin Disease Subjects that Respond to Treatment with a JAK inhibitor as Compared to Control Subjects that do not Respond

| Gene Symbol | Full Gene Name | UniProtKB Accession Number |
|---|---|---|
| ASIC4 | Acid-sensing ion channel 4 | Q96FT7 |
| FAM241B (C10orf35) | Uncharacterized protein FAM241B | Q96D05 |
| LEG1 (C6orf58) | Protein LEG1 homolog | Q6P5S2 |
| CCDC73 | Coiled-coil domain-containing protein 73 | Q6ZRK6 |
| CDH15 | Cadherin-15 | P55291 |
| CLHC1 | Clathrin heavy chain linker domain-containing protein 1 | Q8NHS4 |
| DZIP1 | Zinc finger protein DZIP1 | Q86YF9 |
| EDN1 | Endothelin-1 | P05305 |
| EEF1DP4 | Eukaryotic Translation Elongation Factor 1 Delta Pseudogene 4 | (pseudogene) |
| EFCAB10 | EF-hand calcium-binding domain-containing protein 10 | A6NFE3 |
| FDPSP7 | Farnesyl Diphosphate Synthase Pseudogene 7 | (pseudogene) |
| FSIP2 | Fibrous sheath-interacting protein 2 | Q5CZC0 |
| GDF9 | Growth/differentiation factor 9 | O60383 |
| H1FNT | Testis-specific H1 histone | Q75WM6 |
| HMGB1P31 | High Mobility Group Box 1 Pseudogene 31 | (pseudogene) |
| HS6ST2 | Heparan-sulfate 6-O-sulfotransferase 2 | Q96MM7 |
| HTR1F | 5-hydroxytryptamine receptor 1F | P30939 |
| IGHG3 | Immunoglobulin heavy constant gamma 3 | P01860 |
| IL1RAPL2 | X-linked interleukin-1 receptor accessory protein-like 2 | Q9NP60 |
| LINC00339 | Long Intergenic Non-Protein Coding RNA 339 | (RNA Gene) |
| LINC00623 | Long Intergenic Non-Protein Coding RNA 623 | (RNA Gene) |
| LINC01118 | Long Intergenic Non-Protein Coding RNA 1118 | (RNA Gene) |
| LINC01127 | Long Intergenic Non-Protein Coding RNA 1127 | (RNA Gene) |
| MEF2C-AS1 | MEF2C Antisense RNA 1 | (RNA Gene) |
| MPV17L | Mpv17-like protein | Q2QL34 |
| NKAPP1 | Putative uncharacterized protein CXorf42 | Q8N9T2 |
| PLCZ1 | 1-phosphatidylinositol 4,5-bisphosphate phosphodiesterase zeta-1 | Q86YW0 |
| PRSS30P | Protease, Serine, 30 Pseudogene | (pseudogene) |

TABLE 2-continued

Biomarkers Exhibiting Increased Expression in Inflammatory Skin Disease Subjects that Respond to Treatment with a JAK inhibitor as Compared to Control Subjects that do not Respond

| Gene Symbol | Full Gene Name | UniProtKB Accession Number |
|---|---|---|
| PTPN5 | Tyrosine-protein phosphatase non-receptor type 5 | P54829 |
| RBP3 | Retinol-binding protein 3 | P10745 |
| RNASEK-C17orf49 | RNASEK-C17orf49 readthrough | H0YIS7 |
| RPS26P15 | Ribosomal Protein S26 Pseudogene 15 | (pseudogene) |
| SNX29P1 | Sorting Nexin 29 Pseudogene 1 | (pseudogene) |
| SYDE2 | Rho GTPase-activating protein SYDE2 | Q5VT97 |
| TIMD4 | T-cell immunoglobulin and mucin domain-containing protein 4 | Q96H15 |
| TRPC2 | Transient Receptor Potential Cation Channel Subfamily C Member 2, Pseudogene | (pseudogene) |
| UPK3BL | Uroplakin-3b-like protein 1 | B0FP48 |
| WDR88 | WD repeat-containing protein 88 | Q6ZMY6 |
| ZNF738 | Protein ZNF738 | Q8NE65 |

A reduced expression level compared to a control of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, or 28) genes listed in Table 1 is indicative/predictive that a subject that has, is suspected of having, or is at risk of developing an inflammatory skin disease will respond to a therapy comprising a JAK inhibitor. For example, low expression levels (compared to a control) of ARHGEF35 in a biological sample obtained from a subject prior to treatment with the therapy comprising a JAK inhibitor are predictive that the subject will respond to the therapy comprising a JAK inhibitor.

An increased expression level compared to a control of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39) genes listed in Table 2 is indicative/predictive that a subject that has, is suspected of having, or is at risk of developing an inflammatory skin disease will respond to a therapy comprising a JAK inhibitor. For example, increased expression levels (compared to a control) of ASIC4 in a biological sample obtained from a subject prior to treatment with the therapy comprising a JAK inhibitor are predictive that the subject will respond to the therapy comprising a JAK inhibitor.

A reduced expression level compared to a control of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, or 28) genes listed in Table 1 combined with an increased expression level compared to a control of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39) genes listed in Table 2 is indicative/predictive that a subject that has, is suspected of having, or is at risk of developing an inflammatory skin disease will respond to a therapy comprising a JAK inhibitor. For example, low expression levels (compared to a control) of ARHGEF35 and increased expression levels (compared to a control) of ASIC4 in a biological sample obtained from a subject prior to treatment with the therapy comprising a JAK inhibitor are predictive that the subject will respond to the therapy comprising a JAK inhibitor. In another example, low expression levels (compared to a control) of ARHGEF35, BNIP3P5, BZW1P2, C1QTNF3-AMACR, CAMK4, CCL18, CYTH4, IL17C, IL1RL1, KHSRPP1, KRT18P12, LIPE-AS1, MS4A3, MTND4P9, MYCBP2-AS2, PAPPA, PLA2G2D, PTCHD3P2, RPL7L1P3, SP5, TDRD1, TMED7-TICAM2, TNFRSF11B, TNFSF14, TRAV30, TRBV5-6, TRDV2, and WDR11-AS1 and increased expression levels (compared to a control) of ASIC4, C10orf35, C6orf58, CCDC73, CDH15, CLHC1, DZIP1, EDN1, EEF1DP4, EFCAB10, FDPSP7, FSIP2, GDF9, H1FNT, HMGB1P31, HS6ST2, HTR1F, IGHG3, IL1RAPL2, LINC00339, LINC00623, LINC01118, LINC01127, MEF2C-AS1, MPV17L, NKAPPI, PLCZ1, PRSS30P, PTPN5, RBP3, RNASEK-C17orf49, RPS26P15, SNX29P1, SYDE2, TIMD4, TRPC2, UPK3BL, WDR88, and ZNF738 in a biological sample obtained from a subject prior to treatment with the therapy comprising a JAK inhibitor are predictive that the subject will respond to the therapy comprising a JAK inhibitor.

In some embodiments, the inflammatory skin disease is psoriasis.

In some embodiments, the inflammatory skin disease is atopic dermatitis.

In some embodiments, the inflammatory skin disease is vitiligo.

In some embodiments, the inflammatory skin disease is hidradenitis suppurativa.

In some embodiments, the inflammatory skin disease is rosacea.

In some embodiments, the inflammatory skin disease is Lichen planus.

In some embodiments, the inflammatory skin disease is generalized pustular psoriasis.

In some embodiments, the inflammatory skin disease is palmoplantar pustulosis.

In some embodiments, the inflammatory skin disease is acne.

In some embodiments, the inflammatory skin disease is cutaneous lupus.

In some embodiments, the inflammatory skin disease is dermatomyositis.

In some embodiments, the inflammatory skin disease is a skin disease characterized by elevated Th1, Th2, or Th17 signaling.

Controls

As described above, the methods of the present invention can involve, measuring the expression level of one or more genes (e.g., one or more genes depicted in Table 1 and/or Table 2) in a biological sample from a subject having, suspected of having or at risk of developing an inflammatory skin disease, wherein the expression level of one or more genes, compared to a control, predicts the response of a subject to treatment comprising a JAK inhibitor. In certain embodiments, when the expression level of a gene in Table 1 in a biological sample from a subject having, suspected of having or at risk of developing an inflammatory skin disease is lower than the control, the subject is identified as likely to respond to a therapy comprising a JAK inhibitor. In other embodiments, when the expression level of a gene in Table 2 in a biological sample from a subject having, suspected of having or at risk of developing an inflammatory skin disease is higher than the control, the subject is identified as likely to respond to a therapy comprising a JAK inhibitor. In this context, the term "control" includes a sample (from the same tissue type) obtained from a subject who is known to not respond to a therapy comprising a JAK inhibitor. The term "control" also includes a sample (from the same tissue type) obtained in the past from a subject who is known to not respond to a therapy comprising a JAK inhibitor and used as a reference for future comparisons to test samples taken from subjects for which therapeutic responsiveness is to be predicted. The "control" expression level for a particular gene in a particular cell type or tissue may be pre-established by an analysis of gene expression in one or more (e.g., 2, 3, 4, 5, 6, 7, 8, 9, 10, 15, 20, 25, 30, 35, or 40 or more) subjects, of the same species, that have not responded to treatment with a JAK inhibitor. This pre-established reference value (which may be an average or median expression level taken from multiple subjects that have not responded to the therapy) may then be used for the "control" expression level of the gene in the comparison with the test sample. In such a comparison, the subject is predicted to respond to a therapy comprising a JAK inhibitor if the expression level of the gene being analyzed is lower (Table 1) or higher (Table 2) than the pre-established reference.

The "control" expression level for a particular gene in a particular cell type or tissue may alternatively be pre-established by an analysis of gene expression in one or more subjects that have responded to treatment with a JAK inhibitor. This pre-established reference value (which may be an average or median expression level taken from multiple subjects that have responded to the therapy) may then be used as the "control" expression level in the comparison with the test sample. In such a comparison, the subject is predicted to respond to a therapy comprising a JAK inhibitor if the expression level of the gene being analyzed is the same as, or comparable to (e.g., at least 85% but less than 100% of), the pre-established reference.

In certain embodiments, the "control" is a pre-established cut-off value. A cut-off value is typically an expression level of a gene above or below which is considered predictive of responsiveness of a subject to a therapy of interest. Thus, in accordance with the methods and compositions described herein, a reference gene expression level (e.g., of a gene of Table 1 or Table 2) is identified as a cut-off value, above or below of which is predictive of responsiveness to a therapy comprising a JAK inhibitor. Cut-off values determined for use in the methods described herein can be compared with, e.g., published ranges of concentrations but can be individualized to the methodology used and patient population.

In some embodiments, the expression level of the gene being analyzed is reduced as compared to the expression level of that gene in a control. For example, the expression level of the gene being analyzed can be at least 1.5, 2, 3, 4, 5, 6, 7, 8, 9, 10, 20, 25, 50, 75, or 100 times lower, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% lower, than the expression level of that gene in a control.

In some embodiments, the expression level of the gene being analyzed is increased as compared to the expression level of that gene in a control. For example, the expression level of the gene being analyzed can be at least 1.5, 2, 3, 4, 5, 6, 7, 8, 9, 10, 20, 25, 50, 75, or 100 times higher, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% higher, than the expression level of that gene in a control.

Biological Samples

Suitable biological samples for the methods described herein include any sample that contains skin tissue obtained or derived from the human subject in need of treatment. For example, a biological sample can contain a skin biopsy. A skin biopsy can be obtained by a variety of means, including use of a non-invasive tape strip, an adhesive patch, a dermal shaving, or microplaned skin.

Epidermal skin samples can be collected non-invasively, for example, by applying D-Squame (CuDerm, Dallas, Tex.), an adhesive patch-based skin biopsy device (DermTech, San Diego, Calif.), or a thin film or membrane. Epidermal skin samples can be collected using minimally invasive techniques such as microneedling, dermarollers, or suction blisters. Isolation of RNA, DNA, and protein obtained via non-invasive or minimally invasive techniques is then used to evaluate the expression of biomarkers.

A biological sample can be obtained from a subject having, suspected of having, or at risk of developing, an inflammatory skin disease. In some embodiments, the inflammatory skin disease is psoriasis. In some embodiments, the inflammatory skin disease is atopic dermatitis. In some embodiments, the inflammatory skin disease is vitiligo. In some embodiments, the inflammatory skin disease is hidradenitis suppurativa. In some embodiments, the inflammatory skin disease is rosacea. In some embodiments, the inflammatory skin disease is Lichen planus. In some embodiments, the inflammatory skin disease is generalized pustular psoriasis. In some embodiments, the inflammatory skin disease is palmoplantar pustulosis. In some embodiments, the inflammatory skin disease is acne. In some embodiments, the inflammatory skin disease is cutaneous lupus. In some embodiments, the inflammatory skin disease is dermatomyositis. In some embodiments, the inflammatory skin disease is a skin disease characterized by elevated Th1, Th2, or Th17 signaling.

Methods for obtaining and/or storing samples that preserve the activity or integrity of molecules (e.g., nucleic acids) in the sample are well known to those skilled in the art. For example, a biological sample can be further contacted with one or more additional agents such as buffers and/or inhibitors, including one or more of nuclease, protease, and phosphatase inhibitors, which preserve or minimize changes in the molecules in the sample.

Determining Expression Levels/Concentrations of Biomarkers

Gene expression levels can be detected as, e.g., RNA expression of a target gene. That is, the expression level (amount) of a gene can be determined by detecting and/or measuring the level of mRNA expression of the gene. In some embodiments, gene expression can be detected as the expression level of a gene depicted in Table 1 and/or Table 2.

In some embodiments, the expression level of a gene of interest is determined by measuring RNA levels. A variety of suitable methods can be employed to detect and/or measure the level of mRNA expression of a gene. For example, mRNA expression can be determined using Northern blot or dot blot analysis, reverse transcriptase-PCR (RT-PCR; e.g., quantitative RT-PCR), in situ hybridization (e.g., quantitative in situ hybridization) or nucleic acid array (e.g., oligonucleotide arrays or gene chips) analysis. Details of such methods are described below and in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989; Gibson et al. (1999) *Genome Res.,* 6(10):995-1001; and Zhang et al. (2005) *Environ. Sci. Technol.,* 39(8):2777-2785; U.S. Publication No. 2004086915; European Patent No. 0543942; and U.S. Pat. No. 7,101,663; the disclosures of each of which are incorporated herein by reference in their entirety.

In one example, the presence or amount of one or more discrete mRNA populations in a biological sample can be determined by isolating total mRNA from the biological sample (see, e.g., Sambrook et al. (supra) and U.S. Pat. No. 6,812,341) and subjecting the isolated mRNA to agarose gel electrophoresis to separate the mRNA by size. The size-separated mRNAs are then transferred (e.g., by diffusion) to a solid support such as a nitrocellulose membrane. The presence or amount of one or more mRNA populations in the biological sample can then be determined using one or more detectably-labeled-polynucleotide probes, complementary to the mRNA sequence of interest, which bind to and thus render detectable their corresponding mRNA populations. Detectable-labels include, e.g., fluorescent (e.g., umbelliferone, fluorescein, fluorescein isothiocyanate, rhodamine, dichlorotriazinylamine fluorescein, dansyl chloride, allophycocyanin (APC), or phycoerythrin), luminescent (e.g., europium, terbium, Qdot™ nanoparticles supplied by the Quantum Dot Corporation, Palo Alto, Calif.), radiological (e.g., $^{125}I$, $^{131}I$, $^{35}S$, $^{32}P$, $^{33}P$, or $^{3}H$), and enzymatic (horseradish peroxidase, alkaline phosphatase, beta-galactosidase, or acetylcholinesterase) labels.

Methods for detecting or measuring gene expression (e.g., mRNA expression) can optionally be performed in formats that allow for rapid preparation, processing, and analysis of multiple samples. This can be, for example, in multi-welled assay plates (e.g., 96 wells or 386 wells) or arrays (e.g., nucleic acid chips or protein chips). Stock solutions for various reagents can be provided manually or robotically, and subsequent sample preparation (e.g., RT-PCR, labeling, or cell fixation), pipetting, diluting, mixing, distribution, washing, incubating (e.g., hybridization), sample readout, data collection (optical data) and/or analysis (computer aided image analysis) can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay. Exemplary high-throughput cell-based assays (e.g., detecting the presence or level of a target protein in a cell) can utilize ArrayScan® VTI HCS Reader or KineticScan® HCS Reader technology (Cellomics Inc., Pittsburgh, Pa.).

In some embodiments, the expression level of 2 genes, 3 genes, 4 genes, 5 genes, 6 genes, 7 genes, 8 genes, 9 genes, 10 genes, 11 genes, 12 genes, 13 genes, 14 genes, 15 genes, 16 genes, 17 genes, 18 genes, 19 genes, 20 genes, 21 genes, 22 genes, 23 genes, 24 genes, 25 genes, 26 genes, 27 genes, or 28 genes, or at least 2 genes, at least 3 genes, at least 4 genes, at least 5 genes, at least 6 genes, at least 7 genes, at least 8 genes, at least 9 genes, at least 10 genes, at least 11 genes, at least 12 genes, at least 13 genes, at least 14 genes, at least 15 genes, at least 16 genes, at least 17 genes, at least 18 genes, at least 19 genes, at least 20 genes, at least 21 genes, at least 22 genes, at least 23 genes, at least 24 genes, at least 25 genes, at least 26 genes, at least 27 genes, or at least 28 genes from Table 1 can be assessed and/or measured.

In some embodiments, the expression level of 2 genes, 3 genes, 4 genes, 5 genes, 6 genes, 7 genes, 8 genes, 9 genes, 10 genes, 11 genes, 12 genes, 13 genes, 14 genes, 15 genes, 16 genes, 17 genes, 18 genes, 19 genes, 20 genes, 21 genes, 22 genes, 23 genes, 24 genes, 25 genes, 26 genes, 27 genes, 28 genes, 29 genes, 30 genes, 31 genes, 32 genes, 33 genes, 34 genes, 35 genes, 36 genes, 37 genes, 38 genes, or 39 genes, or at least 2 genes, at least 3 genes, at least 4 genes, at least 5 genes, at least 6 genes, at least 7 genes, at least 8 genes, at least 9 genes, at least 10 genes, at least 11 genes, at least 12 genes, at least 13 genes, at least 14 genes, at least 15 genes, at least 16 genes, at least 17 genes, at least 18 genes, at least 19 genes, at least 20 genes, at least 21 genes, at least 22 genes, at least 23 genes, at least 24 genes, at least 25 genes, at least 26 genes, at least 27 genes, at least 28 genes, at least 29 genes, at least 30 genes, at least 31 genes, at least 32 genes, at least 33 genes, at least 34 genes, at least 35 genes, at least 36 genes, at least 37 genes, at least 38 genes, or at least 39 genes from Table 2 can be assessed and/or measured.

JAK Inhibitors

In some embodiments, the JAK inhibitor is a compound that inhibits JAK1, JAK2, JAK3, and/or TYK2. In some embodiments, the JAK inhibitor is selective for JAK1 and JAK2 over JAK3 and TYK2. In some embodiments, the JAK inhibitor is selective for JAKI over JAK2, JAK3, and TYK2. For example, some of the compounds described herein, or a pharmaceutically acceptable salt thereof, preferentially inhibit JAK1 over one or more of JAK2, JAK3, and TYK2. In some embodiments, the compounds or salts inhibit JAKI preferentially over JAK2 (e.g., have a JAK2/JAKI $IC_{50}$ ratio>1). In some embodiments, the compounds or salts are about 10-fold more selective for JAK1 over JAK2. In some embodiments, the compounds or salts are about 3-fold, about 5-fold, about 10-fold, about 15-fold, or about 20-fold more selective for JAK1 over JAK2 as calculated by measuring $IC_{50}$ at 1 mM ATP.

In some embodiments, the JAK inhibitor is 3-cyclopentyl-3-[4-(7H-pyrrolo[2,3-d]pyrimidin-4-yl)-1H-pyrazol-1-yl]propanenitrile.

In some embodiments, the JAK inhibitor is (3R)-3-cyclopentyl-3-[4-(7H-pyrrolo[2,3-d]pyrimidin-4-yl)-1H-pyrazol-1-yl]propanenitrile (ruxolitinib; also known 3-Cyclopentyl-3-[4-(7H-pyrrolo[2,3-d]pyrimidin-4-yl)-1H-pyrazol yl]propanenitrile and ruxolitinib can be made by the procedure described in U.S. Pat. No. 7,598,257 (Example 67), filed Dec. 12, 2006, which is incorporated herein by reference in its entirety.

In some embodiments, the JAK inhibitor is (3R)-3-cyclopentyl-3-[4-(7H-pyrrolo[2,3-d]pyrimidin-4-yl)-1H-pyrazol-1-yl]propanenitrile phosphoric acid salt.

In some embodiments, the JAK inhibitor is barcitinib, tofacitinib, oclacitinib, filgotinib, gandotinib, lestaurtinib, momelotinib, bacritinib, PF-04965842, upadacitinib, peficitinib, fedratinib, cucurbitacin I, ATI-501 (Aclaris), ATI-502 (Aclaris), JTE052 (Leo Pharma and Japan Tobacco), or CHZ868.

In some embodiments, the JAK inhibitor can be an isotopically-labeled compound, or a pharmaceutically acceptable salt thereof. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$).

One or more constituent atoms of the compounds described herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

Accordingly, in some embodiments, the JAK inhibitor is a compound, wherein one or more hydrogen atoms in the compound are replaced by deuterium atoms, or a pharmaceutically acceptable salt thereof.

In some embodiments, the JAK inhibitor is ruxolitinib, wherein one or more hydrogen atoms are replaced by deuterium atoms, or a pharmaceutically acceptable salt thereof. In some embodiments, the JAK inhibitor is any of the compounds in U.S. Pat. No. 9,249,149 (which is incorporated herein by reference in its entirety), or a pharmaceutically acceptable salt thereof. In some embodiments, the JAK inhibitor is CTP-543, or a pharmaceutically acceptable salt thereof. In some embodiments, the compound is a compound of Formula I:

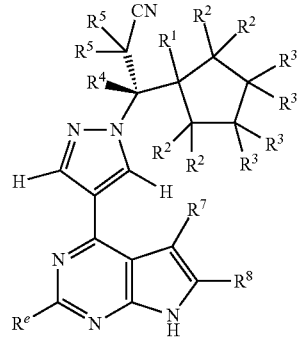

or a pharmaceutically acceptable salt thereof, wherein:
$R^1$ is selected from H and D;
each $R^2$ is independently selected from H and D, provided that each $R^2$ attached to a common carbon is the same;
each $R^3$ is independently selected from H and D, provided that each $R^3$ attached to a common carbon is the same;
$R^4$ is selected from H and D;
each $R^5$ is the same and is selected from H and D; and
$R^6$, $R^7$, and $R^8$ are each independently selected from H and D; provided that when $R^1$ is H, each $R^2$ and each $R^3$ are H, IV is H, and each of $R^6$, $R^7$, and $R^8$ is H, then each $R^5$ is D.

In some embodiments, the JAK inhibitor is a compound of Formula I selected from the following compounds 100-130 in the table below (wherein $R^6$, $R^7$, and $R^8$ are each H), or a pharmaceutically acceptable salt thereof. In some embodiments, the JAK inhibitor is a compound of Formula I selected from the following compounds 200-231 in the table below (wherein $R^6$, $R^7$, and $R^8$ are each D), or a pharmaceutically acceptable salt thereof.

| Compound | R¹ | Each R² | Each R³ | R⁴ | Each R⁵ |
|---|---|---|---|---|---|
| 100 | H | H | H | D | H |
| 101 | H | H | H | H | D |
| 102 | H | H | H | D | D |
| 103 | H | H | D | H | H |
| 104 | H | H | D | D | H |
| 105 | H | H | D | H | D |
| 106 | H | H | D | D | D |
| 107 | H | D | H | H | H |
| 108 | H | D | H | D | H |
| 109 | H | D | H | H | D |
| 110 | H | D | H | D | D |
| 111 | H | D | D | H | H |
| 112 | H | D | D | D | H |
| 113 | H | D | D | H | D |
| 114 | H | D | D | D | D |
| 115 | D | H | H | H | H |
| 116 | D | H | H | D | H |
| 117 | D | H | H | H | D |
| 118 | D | H | H | D | D |
| 119 | D | H | D | H | H |
| 120 | D | H | D | D | H |
| 121 | D | H | D | H | D |
| 122 | D | H | D | D | D |
| 123 | D | D | H | H | H |
| 124 | D | D | H | D | H |
| 125 | D | D | H | H | D |
| 126 | D | D | H | D | D |
| 127 | D | D | D | H | H |
| 128 | D | D | D | D | H |
| 129 | D | D | D | H | D |
| 130 | D | D | D | D | D |
| 200 | H | H | H | D | H |
| 201 | H | H | H | H | D |
| 202 | H | H | H | D | D |
| 203 | H | H | D | H | H |
| 204 | H | H | D | D | H |
| 205 | H | H | D | H | D |
| 206 | H | H | D | D | D |
| 207 | H | D | H | H | H |
| 208 | H | D | H | D | H |
| 209 | H | D | H | H | D |
| 210 | H | D | H | D | D |
| 211 | H | D | D | H | H |
| 212 | H | D | D | D | H |
| 213 | H | D | D | H | D |
| 214 | H | D | D | D | D |
| 215 | D | H | H | H | H |
| 216 | D | H | H | D | H |
| 217 | D | H | H | H | D |
| 218 | D | H | H | D | D |
| 219 | D | H | D | H | H |
| 220 | D | H | D | D | H |
| 221 | D | H | D | H | D |
| 222 | D | H | D | D | D |
| 223 | D | D | H | H | H |
| 224 | D | D | H | D | H |
| 225 | D | D | H | H | D |
| 226 | D | D | H | D | D |
| 227 | D | D | D | H | H |
| 228 | D | D | D | D | H |
| 229 | D | D | D | H | D |
| 230 | D | D | D | D | D |
| 231 | H | H | H | H | H |

In some embodiments, the JAK inhibitor is baricitinib, wherein one or more hydrogen atoms are replaced by deuterium atoms, or a pharmaceutically acceptable salt thereof. In some embodiments, the JAK inhibitor is any of the compounds in U.S. Pat. No. 9,540,367 (which is incorporated herein by reference in its entirety), or a pharmaceutically acceptable salt thereof.

In some embodiments, the JAK inhibitor is a compound of Table 3, or a pharmaceutically acceptable salt thereof. The compounds in Table 3 are selective JAK1 inhibitors (selective over JAK2, JAK3, and TYK2).

TABLE 3

Examples of JAK inhibitors

| Comp. No. | Prep. | Name | Structure |
|---|---|---|---|
| 1 | US 2011/0224190 (Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile (itacitinib; also known as INCB039110) | 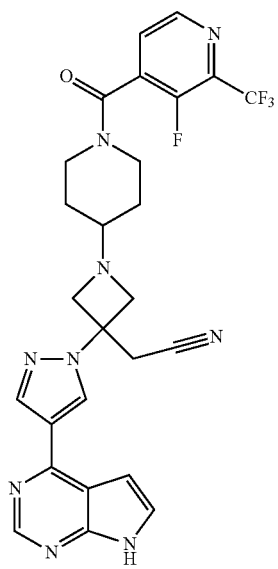 [SMILES: N#CCC1(n2cc(-c3ncnc4[nH]ccc34)cn2)CN(C2CCN(C(=O)c3ccnc(C(F)(F)F)c3F)CC2)C1] |

TABLE 3-continued

Examples of JAK inhibitors

| Comp. No. | Prep. | Name | Structure |
|---|---|---|---|
| 2 | US 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 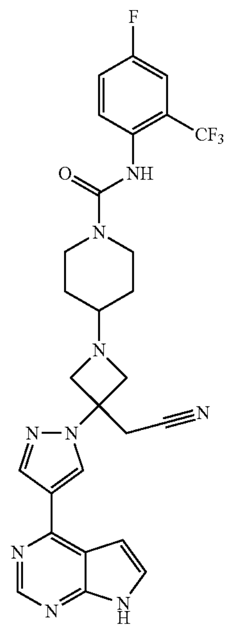 [SMILES: N#CCC1(n2cc(-c3ncnc4[nH]ccc34)cn2)CN(C2CCN(C(=O)Nc3ccc(F)cc3C(F)(F)F)CC2)C1] |
| 3 | US 2011/ 0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 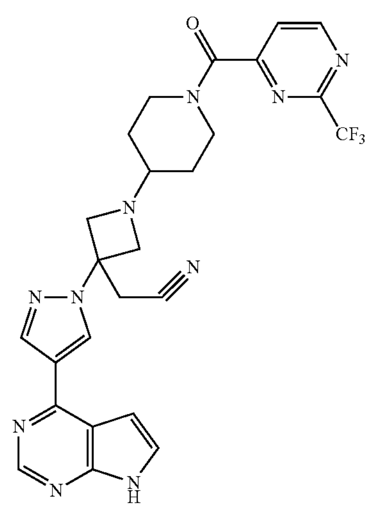 [SMILES: N#CCC1(n2cc(-c3ncnc4[nH]ccc34)cn2)CN(C2CCN(C(=O)c3ccnc(C(F)(F)F)n3)CC2)C1] |
| 4 | US 2014/ 0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 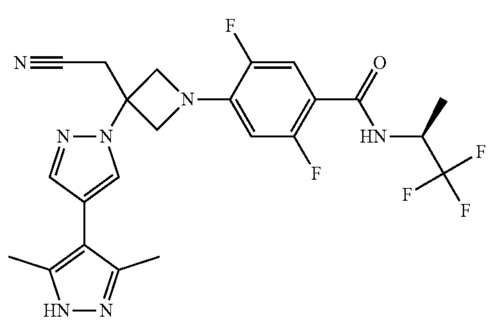 [SMILES: Cc1n[nH]c(C)c1-c1cnn(C2(CC#N)CN(c3cc(F)c(C(=O)N[C@@H](C)C(F)(F)F)cc3F)C2)c1] |

TABLE 3-continued

Examples of JAK inhibitors

| Comp. No. | Prep. | Name | Structure |
|---|---|---|---|
| 5 | US 2014/0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 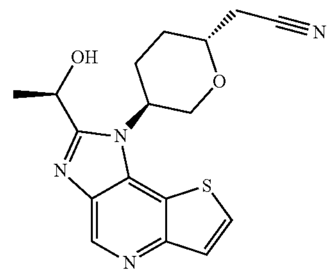 [SMILES: C[C@@H](O)c1nc2cnc3ccsc3c2n1[C@H]1CC[C@H](CC#N)OC1] |
| 6 | US 2010/0298334 (Example 2) | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 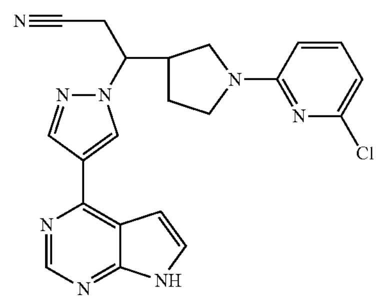 [SMILES: N#CCC(C1CCN(c2cccc(Cl)n2)C1)n1cc(-c2ncnc3[nH]ccc23)cn1] |
| 7 | US 2010/0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 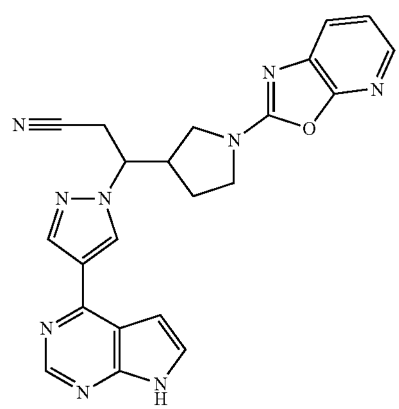 [SMILES: N#CCC(C1CCN(c2nc3cccnc3o2)C1)n1cc(-c2ncnc3[nH]ccc23)cn1] |
| 8 | US 2011/0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 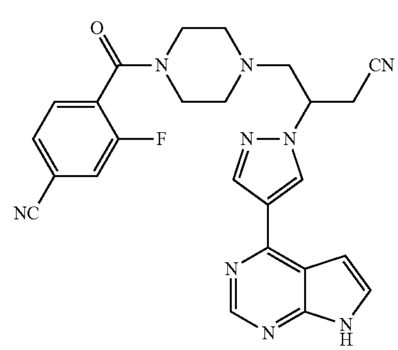 [SMILES: N#CCC(CN1CCN(C(=O)c2ccc(C#N)cc2F)CC1)n1cc(-c2ncnc3[nH]ccc23)cn1] |

TABLE 3-continued

Examples of JAK inhibitors

| Comp. No. | Prep. | Name | Structure |
|---|---|---|---|
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 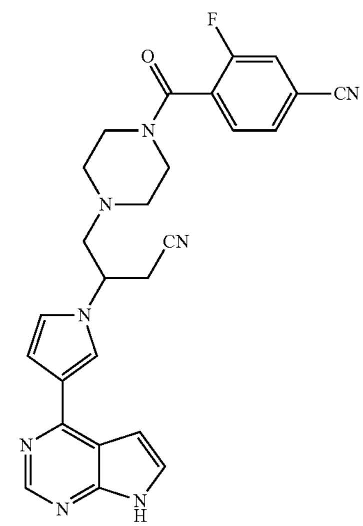 [SMILES: N#CCC(CN1CCN(C(=O)c2ccc(C#N)cc2F)CC1)n1ccc(-c2ncnc3[nH]ccc23)c1] |
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 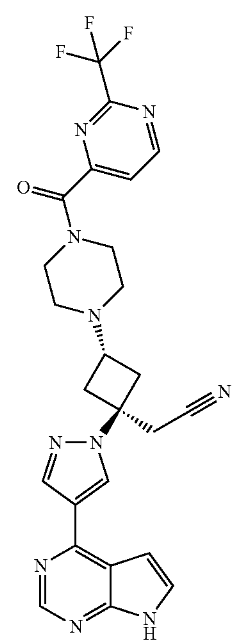 [SMILES: N#CC[C@]1(n2cc(-c3ncnc4[nH]ccc34)cn2)C[C@H](N2CCN(C(=O)c3ccnc(C(F)(F)F)n3)CC2)C1] |

TABLE 3-continued

Examples of JAK inhibitors

| Comp. No. | Prep. | Name | Structure |
|---|---|---|---|
| 11 | US 2012/0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 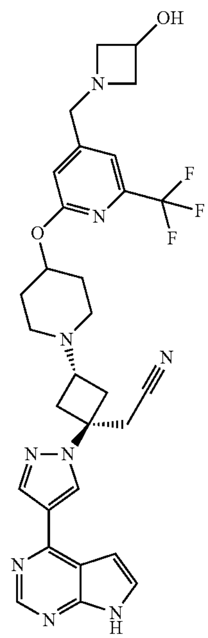 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] |
| 12 | US 2012/0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 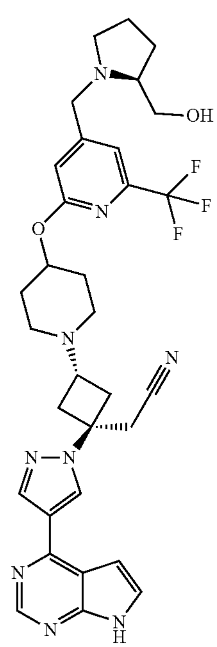 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] |

TABLE 3-continued

Examples of JAK inhibitors

| Comp. No. | Prep. | Name | Structure |
|---|---|---|---|
| 13 | US 2012/ 0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 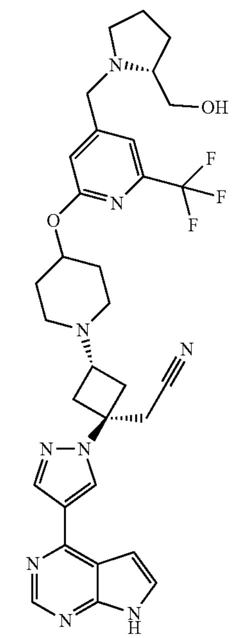 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] |
| 14 | US 2012/ 0149682 (Example 20) | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 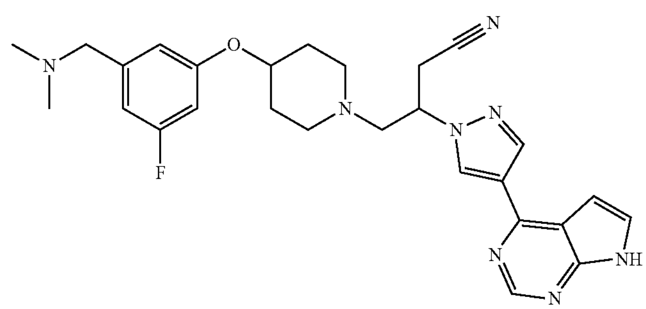 [SMILES: CN(C)Cc1cc(F)cc(OC2CCN(CC(CC#N)n3cc(-c4ncnc5[nH]ccc45)cn3)CC2)c1] |
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 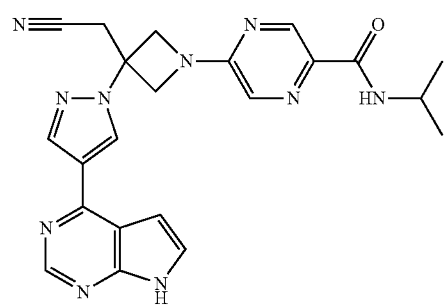 [SMILES: CC(C)NC(=O)c1cnc(N2CC(CC#N)(n3cc(-c4ncnc5[nH]ccc45)cn3)C2)cn1] |

TABLE 3-continued

Examples of JAK inhibitors

| Comp. No. | Prep. | Name | Structure |
|---|---|---|---|
| 16 | US 2013/0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 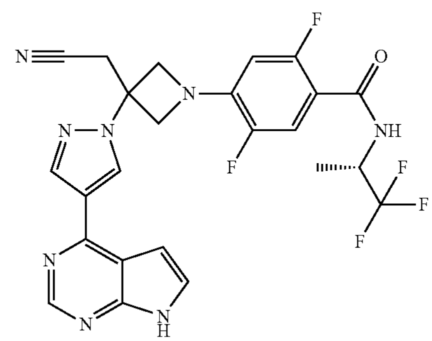 [SMILES: C[C@H](NC(=O)c1cc(F)c(N2CC(CC#N)(n3cc(-c4ncnc5[nH]ccc45)cn3)C2)cc1F)C(F)(F)F] |
| 17 | US 2013/0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 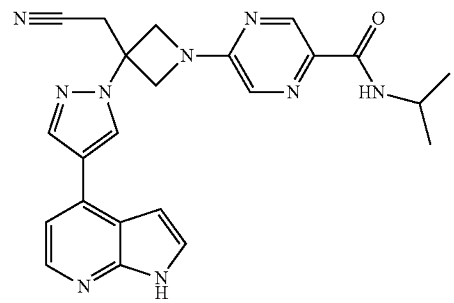 [SMILES: CC(C)NC(=O)c1cnc(N2CC(CC#N)(n3cc(-c4ccnc5[nH]ccc45)cn3)C2)cn1] |
| 18 | US 2013/0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 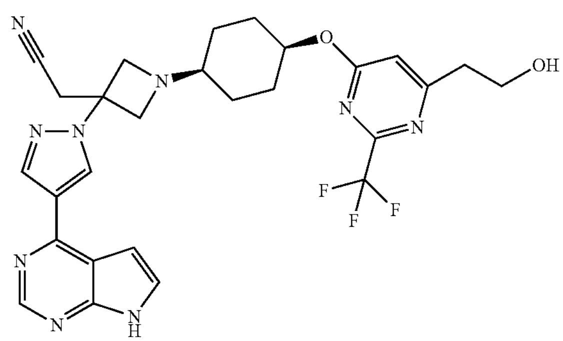 |
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 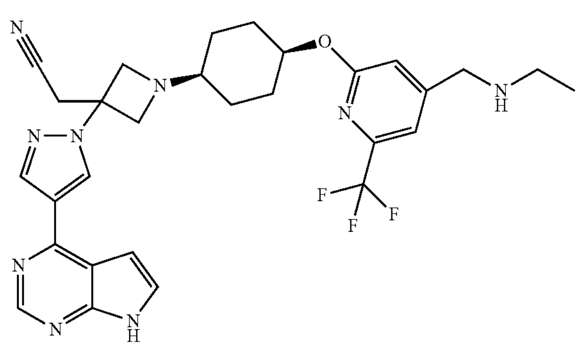 |

TABLE 3-continued

Examples of JAK inhibitors

| Comp. No. | Prep. | Name | Structure |
|---|---|---|---|
| 20 | US 2013/0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 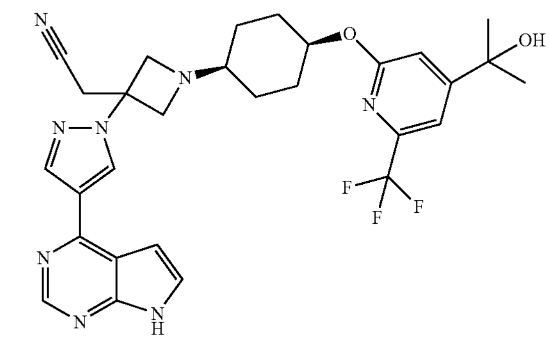 |
| 21 | US 2013/0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 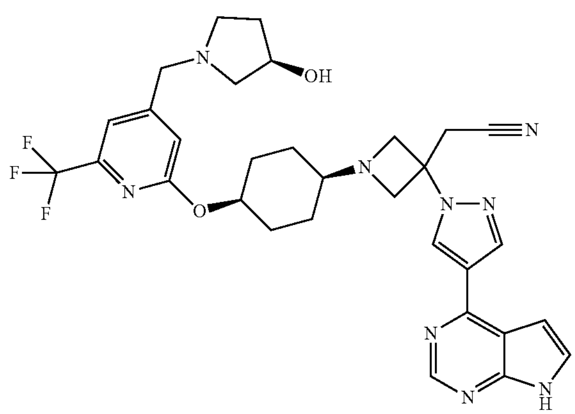 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] |
| 22 | US 2013/0045963 (Example 95) | {1-{cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 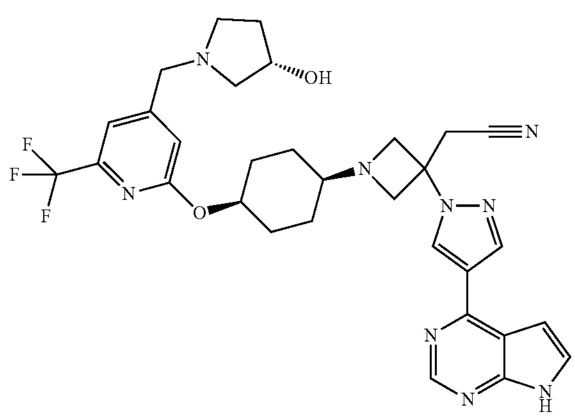 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] |

TABLE 3-continued

Examples of JAK inhibitors

| Comp. No. | Prep. | Name | Structure |
|---|---|---|---|
| 23 | US 2014/0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 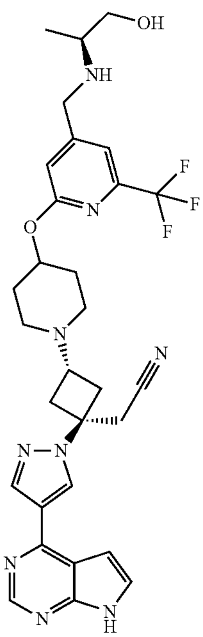 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] |
| 24 | US 2014/0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 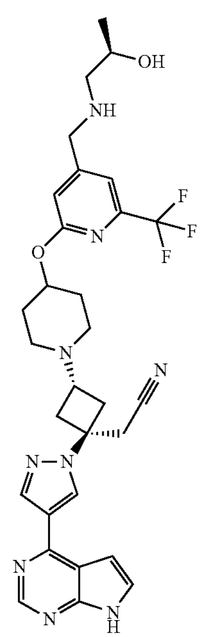 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] |

TABLE 3-continued

Examples of JAK inhibitors

| Comp. No. | Prep. | Name | Structure |
|---|---|---|---|
| 25 | US 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 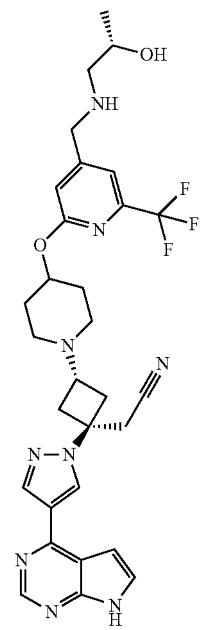 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] |
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 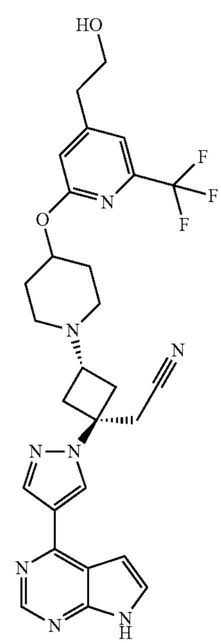 [SMILES: N#CC[C@]1(n2cc(-c3ncnc4[nH]ccc34)cn2)C[C@H](N2CCC(Oc3cc(CCO)cc(C(F)(F)F)n3)CC2)C1] |

In some embodiments, the JAK inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the JAK inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the JAK inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK inhibitor is 4-[3-(cyanomethyl)-3-(3',5'-dimethyl-1H, 1'H-4,4'-bipyrazol-1-yl)azetidin-1-yl]-2,5-difluoro-N-[(1S)-2,2,2-trifluoro-1-methylethyl]benzamide phosphoric acid salt.

The synthesis and preparation of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide and the phosphoric acid salt of the same can be found, e.g., in US Patent Publ. No. US 2014/0343030, filed May 16, 2014, which is incorporated herein by reference in its entirety.

In some embodiments, the JAK inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile monohydrate.

Synthesis of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 3 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, JAK inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

Methods of Treatment

The methods disclosed herein enable the assessment of whether or not a subject having, suspected of having or at risk of developing an inflammatory skin disease is likely to respond (e.g., likely to have greater improvement in disease as evidenced by reduced skin disease severity and/or disease remission/resolution) to a therapy comprising a JAK inhibitor. A subject having, suspected of having or at risk of developing an inflammatory skin disease who is likely to respond to a JAK inhibitor can be administered a JAK inhibitor (e.g., topically administered such as topically administered ruxolitinib). Conversely, a subject having, suspected of having or at risk of developing an inflammatory skin disease who is less likely to respond to a JAK inhibitor (e.g., topically administered such as topically administered ruxolitinib) can be administered an additional therapy that is suitable for treatment of the inflammatory skin disease.

The methods of this disclosure also enable the stratification of subjects having, suspected of having or at risk of developing an inflammatory skin disease into groups of subjects that are more likely to benefit, and groups of subjects that are less likely to benefit, from treatment comprising a JAK inhibitor. The ability to select such subjects from a pool of inflammatory skin disease subjects who are being considered for treatment with a JAK inhibitor is beneficial for administering an effective treatment to the subject.

In one embodiment, the subject to be treated with a JAK inhibitor (e.g., topically administered such as topically administered ruxolitinib) has, is suspected of having, or is likely to develop an inflammatory skin disease. In certain embodiments, the subject to be treated with a therapy comprising a JAK inhibitor (e.g., topically administered such as topically administered ruxolitinib) has, is suspected of having, or is likely to develop psoriasis. In other embodiments, the subject to be treated with a therapy comprising a JAK inhibitor (e.g., topically administered such as topically administered ruxolitinib) has, is suspected of having, or is likely to develop atopic dermatitis. In other embodiments, the subject to be treated with a therapy comprising a JAK inhibitor (e.g., topically administered such as topically administered ruxolitinib) has, is suspected of having, or is likely to develop vitiligo. In other embodiments, the subject to be treated with a therapy comprising a JAK inhibitor (e.g., topically administered such as topically administered ruxolitinib) has, is suspected of having, or is likely to develop hidradenitis suppurativa. In other embodiments, the subject to be treated with a therapy comprising a JAK inhibitor (e.g., topically administered such as topically administered ruxolitinib) has, is suspected of having, or is likely to develop rosacea. In other embodiments, the subject to be treated with a therapy comprising a JAK inhibitor (e.g., topically administered such as topically administered ruxolitinib) has, is suspected of having, or is likely to develop Lichen planus. In other embodiments, the subject to be treated with a therapy comprising a JAK inhibitor (e.g., topically administered such as topically administered ruxolitinib) has, is suspected of having, or is likely to develop generalized pustular psoriasis. In other embodiments, the subject to be treated with a therapy comprising a JAK inhibitor (e.g., topically administered such as topically administered ruxolitinib) has, is suspected of having, or is likely to develop palmoplantar pustulosis. In other embodiments, the subject to be treated with a therapy comprising a JAK inhibitor (e.g., topically administered such as topically administered ruxolitinib) has, is suspected of having, or is likely to develop acne. In other embodiments, the subject to be treated with a therapy comprising a JAK inhibitor (e.g., topically administered such as topically administered ruxolitinib) has, is suspected of having, or is likely to develop cutaneous lupus. In other embodiments, the subject to be treated with a therapy comprising a JAK inhibitor (e.g., topically administered such as topically administered ruxolitinib) has, is suspected of having, or is likely to develop dermatomyositis. In other embodiments, the subject to be treated with a therapy comprising a JAK inhibitor (e.g., topically administered such as topically administered ruxolitinib) has, is suspected of having, or is likely to develop a skin disease characterized by elevated Th1, Th2, or Th17 signaling.

If the subject having an inflammatory skin disease is more likely to respond to a therapy comprising a JAK inhibitor (based on the expression level of one or more of the biomarkers described above (see Tables 1 and 2)), the subject can then be administered an effective amount of the JAK inhibitor (e.g., topically administered such as topically administered ruxolitinib). An effective amount of the JAK inhibitor can suitably be determined by a health care practitioner taking into account, for example, the characteristics of the patient (age, sex, weight, race, etc.), the progression of the disease, and prior exposure to the drug. If the subject is less likely to respond to a therapy comprising a JAK inhibitor, the subject can then be optionally administered a therapy that does not comprise a JAK inhibitor.

The methods can also be applied to individuals at risk of developing an inflammatory skin disease. Such individuals include those who have a family history of the inflammatory skin disease (e.g., having one or two parents with the inflammatory skin disease).

After stratifying or selecting a subject based on whether the subject will be more likely or less likely to respond to a JAK inhibitor, a medical practitioner (e.g., a doctor) can administer the appropriate therapeutic modality to the subject. Methods of administering a JAK inhibitor are well known in the art.

In cases where the subject having an inflammatory skin disease and predicted to respond to a JAK inhibitor has been previously administered one or more non-JAK inhibitor therapies, the therapy comprising a JAK inhibitor can replace or augment a previously or currently administered therapy. For example, upon treating with the therapy comprising a JAK inhibitor, administration of the one or more non-JAK inhibitor therapies can cease or diminish, e.g., be administered at lower levels. Administration of the previous therapy can be maintained while the therapy comprising a JAK inhibitor is administered. In some embodiments, a previous therapy can be maintained until the level of the therapy comprising a JAK inhibitor reaches a level sufficient to provide a therapeutic effect.

A subject treated with a JAK inhibitor according to the methods described herein (e.g., a topically administered a JAK inhibitor such as topically administered ruxolitinib) can be treated in combination with one or more additional compositions that are effective for treatment of an inflammatory skin disease. Examples of compositions that can be used in such combination treatment include corticosteroids (e.g., topical corticosteroids), Vitamin D analogues, anthralin, retinoids (e.g., topical retinoids), calcineurin inhibitors (e.g., tacrolimus or pimecrolimus), salicylic acid, phototherapy, azathioprine, mycophenolate mofetil, methotrexate, cyclosporine, etanercept, infliximab, adalimumab, ustekinumab, golimumab, rituximab, apremilast, secukinumab, ixekizumab, thioguanine, hydroxyurea, and isotretinoin.

The following are examples of the practice of the invention. They are not to be construed as limiting the scope of the invention in any way.

EXAMPLES

Example 1: Identification of Genes Differentially Expressed in Patients with Mild to Moderate Plaque Psoriasis that are Complete Responders to Treatment with Ruxolitinib Full thickness skin biopsies were collected from individuals with mild to moderate plaque psoriasis, enrolled in a study of ruxolitinib (INCB018424) for the treatment of plaque psoriasis involving 2-20% of body surface area. All subjects consented to the biopsy collection and met the inclusion and exclusion criteria outlined in the clinical protocol. Once collected, skin biopsies were processed from full tissue into ribonucleic acid (RNA) for further analysis and subsequently analyzed using RNA sequencing. Samples were separated into to two groups based on clinical response to treatment with topical INCB018424 and outlined in Table 4. Specifically, samples were classified as "responder" or "non-responder" based on their therapeutic response at day 28 of treatment ("PASI" refers to psoriasis area and severity index). Individuals were topically applied INCB018424 twice daily, with applications at least 10 hours apart, at a dose strength of 1.0% or 1.5% INCB018424 phosphate in a cream formulation.

TABLE 4

Characterization and Classification of Subjects Enrolled in Study

| Subject ID | Treatment | Classification | % Change in PASI at Day 28 |
|---|---|---|---|
| 1004 | 1.0% BID | Responder | −60.0% |
| 1005 | 1.0% BID | Responder | −66.7% |
| 1006 | 1.0% BID | Responder | −66.7% |
| 3004 | 1.5% BID | Non-Responder | −40.0% |
| 1001 | 1.5% BID | Responder | −60.0% |
| 2001 | 1.5% BID | Responder | −85.7% |
| 2002 | 1.5% BID | Non-Responder | −40.0% |
| 3001 | 1.5% BID | Non-Responder | −33.3% |
| 4001 | 1.5% BID | Responder | −50.0% |
| 1003 | 1.5% QD | Non-Responder | −33.3% |
| 2005 | 1.5% QD | Responder | −80.0% |
| 6001 | 1.5% QD | Responder | −50.0% |

RNA-sequencing was conducted on all biopsy samples by Beijing Genomics Institute using the Illumina HiSeq 4000 system. Data was then aligned and quality controlled in OmicSoft Array Studio using the Human Genome B38 library. The Fragments Per Kilobase of transcript per Million (FPKM) mapped reads (the relative expression of a transcript) were generated and used in all downstream analysis. Significant differences in differentially expressed genes between groups were identified using ANOVA tests. RNA-sequencing identified a total of 1136 differentially expressed genes between the responder and non-responder groups at baseline (with raw p-value<0.05). Six hundred twenty-nine genes were increased and 507 genes were decreased in responders compared to non-responders (Table 5).

TABLE 5

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| AADACL4 | 3.0934 | 0.0157 | AADAC | −2.965 | 0.0441 |
| ABCA10 | 1.5096 | 0.0388 | AC002480.4 | −3.6976 | 0.0211 |
| ABCC5 | 1.4066 | 0.0439 | AC003991.3 | −7.5887 | 1.5E−05 |
| ABCC6 | 2.4984 | 0.002 | AC005253.2 | −1.3903 | 0.0235 |
| ABHD10 | 1.1785 | 0.0466 | AC005363.9 | −1.7739 | 0.0483 |
| AC005083.1 | 1.7125 | 0.0176 | AC005481.5 | −1.7651 | 0.0043 |
| AC005224.2 | 1.7007 | 0.0311 | AC006129.3 | −2.7394 | 0.0273 |
| AC005387.2 | 4.8803 | 0.0498 | AC006372.6 | −8.8879 | 0.0163 |
| AC005519.4 | 1.5689 | 0.0168 | AC007036.5 | −5.1625 | 0.0448 |
| AC005592.2 | 5.7244 | 0.0365 | AC007163.6 | −4.197 | 0.0261 |
| AC007041.2 | 3.4552 | 0.0342 | AC008132.15 | −1.6706 | 0.0258 |
| AC008074.3 | 2.6772 | 0.0172 | AC009133.17 | −2.8047 | 0.0125 |
| AC009495.3 | 5.0566 | 0.0338 | AC009487.6 | −2.6827 | 0.0038 |
| AC009501.4 | 1.2817 | 0.0361 | AC010733.5 | −1.9765 | 0.0302 |
| AC009542.2 | 2.3156 | 0.0468 | AC013268.4 | −2.821 | 0.0263 |
| AC012146.7 | 1.9247 | 0.0132 | AC068492.1 | −3.239 | 0.0242 |
| AC012358.8 | 2.2389 | 0.05 | AC069155.1 | −3.2661 | 0.0248 |
| AC017002.2 | 2.8863 | 0.0421 | AC073254.1 | −1.743 | 0.0458 |
| AC022819.3 | 1.9352 | 0.0108 | AC079753.4 | −2.417 | 0.0303 |
| AC025918.2 | 6.381 | 0.0299 | AC098820.2 | −2.4383 | 0.0267 |
| AC058791.1 | 2.4451 | 0.0022 | AC105760.3 | −1.4717 | 0.0259 |
| AC064836.3 | 4.5073 | 0.0016 | AC108463.2 | −6.0749 | 0.0295 |
| AC068831.15 | 33.7466 | 0.0189 | AC110299.5 | −5.3452 | 0.0476 |
| AC078852.2 | 4.2153 | 0.0427 | AC113607.2 | −2.0512 | 0.0242 |
| AC084809.3 | 5.1227 | 0.0301 | AC114765.1 | −2.1064 | 0.0252 |
| AC091133.1 | 4.187 | 0.03 | AC140542.2 | −1.7625 | 0.0256 |
| AC091729.9 | 1.653 | 0.0113 | AC144831.3 | −1.8391 | 0.0066 |
| AC092301.3 | 1.9812 | 0.0449 | ACAD9 | −1.3497 | 0.0173 |
| AC093690.1 | 2.5423 | 0.037 | ACKR4 | −2.0068 | 0.0185 |
| AC115617.2 | 10.7038 | 0.0026 | ACTL6B | −2.2165 | 0.0354 |
| AC131097.4 | 2.4606 | 0.0306 | AGAP2 | −1.6615 | 0.0086 |
| AC132217.4 | 4.4803 | 0.0457 | AGGF1P6 | −2.5434 | 0.0247 |
| AC137932.6 | 2.2344 | 0.022 | ANAPC1P1 | −2.3043 | 0.0318 |
| AC138969.4 | 11.6305 | 0.0014 | ANKRD52 | −1.1669 | 0.043 |
| AC144449.1 | 2.1057 | 0.0237 | ANKRD61 | −1.7977 | 0.027 |
| AC241585.2 | 1.5797 | 0.0356 | AP001059.5 | −4.39 | 0.0012 |
| ACSM1 | 3.48 | 0.0144 | AP1S3 | −2.4306 | 0.0442 |
| ACTN3 | 2.3326 | 0.0488 | APOBEC2 | −3.5305 | 0.0309 |
| ADAM21 | 2.9617 | 0.0132 | APOBEC3A | −3.4965 | 0.0403 |
| ADGRL4 | 1.3932 | 0.0221 | APOBR | −1.2607 | 0.0478 |
| AF131215.9 | 2.1281 | 0.0179 | AQP3 | −1.7706 | 0.0241 |
| AIFM3 | 2.4232 | 0.0128 | ARC | −1.9639 | 0.0321 |
| AKNAD1 | 2.6939 | 0.0452 | ARHGAP26-AS1 | −2.0671 | 0.0287 |
| AL109761.5 | 5.2843 | 0.0214 | ARHGEF35 | −2.6708 | 0.0009 |
| AL135745.1 | 69.3807 | 0.0008 | ARHGEF5 | −1.4877 | 0.026 |
| AMTN | 7.4489 | 0.0361 | ARL4D | −1.5663 | 0.0248 |
| AMY2A | 2.9016 | 0.0483 | ARMC10P1 | −2.9753 | 0.0386 |
| ANAPC16 | 1.1272 | 0.007 | ASPHD2 | −1.8431 | 0.0219 |
| ANKRD1 | 2.2529 | 0.0172 | BCL3 | −1.54 | 0.0267 |
| ANO4 | 2.7146 | 0.0381 | BEND3P1 | −3.3631 | 0.0464 |
| AP000254.8 | 2.6366 | 0.0156 | BICC1 | −1.168 | 0.0445 |
| AP000347.4 | 2.5589 | 0.0426 | BISPR | −2.193 | 0.0455 |
| AP000560.3 | 5.9583 | 0.0002 | BMPER | −2.5414 | 0.0488 |
| AP000577.2 | 3.7727 | 0.0358 | BNIP3P5 | −8.8373 | 0.008 |
| AQP11 | 2.3888 | 0.0226 | BRCC3P1 | −3.7509 | 0.023 |
| ARL5AP3 | 4.0039 | 0.0451 | BZW1P2 | −2.4089 | 0.0089 |
| ASB10 | 2.6619 | 0.0145 | C16orf52 | −1.1769 | 0.0297 |
| ASIC4 | 3.1041 | 0.0077 | C17orf96 | −1.9207 | 0.0452 |
| AUTS2 | 1.22 | 0.0318 | C1orf143 | −2.4194 | 0.0309 |
| AZIN2 | 1.3707 | 0.0149 | C1orf220 | −1.6634 | 0.0458 |
| BCAT2 | 1.3471 | 0.0036 | C1QTNF3-AMACR | −7.6974 | 0.0068 |
| C10orf35 | 1.7202 | 0.0075 | C2orf69P1 | −2.3033 | 0.0271 |
| C11orf74 | 1.3773 | 0.0317 | C9orf135 | −2.7881 | 0.0254 |
| C16orf58 | 1.1412 | 0.0431 | CA1 | −2.4175 | 0.0247 |
| C19orf84 | 3.0568 | 0.0471 | CAMK4 | −2.8075 | 0.0025 |
| C1GALT1C1L | 2.2032 | 0.0188 | CBARP | −1.4458 | 0.0167 |
| C21orf62 | 1.9436 | 0.0393 | CBLL1 | −1.234 | 0.0339 |
| C2-AS1 | 3.6958 | 0.049 | CCDC150P1 | −2.0923 | 0.0281 |
| C5AR1 | 1.6161 | 0.0228 | CCL18 | −4.4125 | 0.0092 |
| C6orf163 | 2.6955 | 0.0138 | CD4 | −1.3528 | 0.0321 |
| C6orf48 | 1.2568 | 0.0485 | CDC42EP2 | −1.4702 | 0.0264 |

TABLE 5-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| C6orf52 | 5.9699 | 0.0143 | CDH4 | −1.6458 | 0.0384 |
| C6orf58 | 4.3935 | 0.009 | CDKN1A | −1.937 | 0.0324 |
| C9orf173-AS1 | 2.2615 | 0.0388 | CEBPB | −1.7354 | 0.0211 |
| C9orf43 | 1.7597 | 0.0418 | CENPVP3 | −2.0229 | 0.0249 |
| CAPN12 | 1.9086 | 0.0415 | CH507-216K13.2 | −1.6685 | 0.0321 |
| CASP6 | 1.2754 | 0.0205 | CIB2 | −1.4764 | 0.0211 |
| CBR3-AS1 | 1.4782 | 0.036 | CISH | −1.2926 | 0.029 |
| CBY1 | 1.2118 | 0.0489 | CLEC10A | −1.9121 | 0.0232 |
| CCBL1 | 1.5551 | 0.0239 | CRCP | −1.2828 | 0.0492 |
| CCDC184 | 1.8853 | 0.0363 | CRHR1-IT1 | −1.6158 | 0.0117 |
| CCDC34 | 1.3229 | 0.0084 | CSF1 | −1.3693 | 0.0139 |
| CCDC73 | 1.7066 | 0.0001 | CSGALNACT2 | −1.2265 | 0.0078 |
| CCDC92 | 1.2989 | 0.0316 | CTA-373H7.7 | −2.8876 | 0.0253 |
| CCL16 | 3.2532 | 0.038 | CTB-131K11.1 | −1.09 | 0.0451 |
| CCNB1IP1 | 1.2334 | 0.0359 | CTB-60E11.9 | −8.5092 | 1.67E-11 |
| CCR10 | 2.3295 | 0.0319 | CTC-421K24.1 | −5.0303 | 0.0247 |
| CD19 | 2.9729 | 0.0281 | CTC-459M5.2 | −3.9674 | 0.0426 |
| CDCA7L | 1.2438 | 0.048 | CTC-499J9.1 | −3.223 | 0.0249 |
| CDH15 | 3.2475 | 0.0067 | CTC-518P12.6 | −3.2359 | 0.0283 |
| CDKN2AIPNL | 1.26 | 0.0352 | CTD-2017C7.1 | −2.7121 | 0.0245 |
| CEP120 | 1.2635 | 0.0226 | CTD-2129N1.1 | −5.8702 | 0.0244 |
| CEP164P1 | 2.9968 | 0.0259 | CTD-2199O4.7 | −2.0034 | 0.0221 |
| CEP290 | 1.5648 | 0.0254 | CTD-2503O16.4 | −5.5014 | 0.0114 |
| CFAP74 | 1.8202 | 0.0492 | CTD-2547E10.3 | −5.2914 | 0.0411 |
| CH17-132F21.5 | 3.1554 | 0.0202 | CTD-2583A14.9 | −5.435 | 0.0265 |
| CH17-264B6.3 | 7.9081 | 0.0116 | CTD-3032H12.1 | −4.5129 | 0.0377 |
| CHRNA1 | 3.561 | 0.0104 | CTD-3137H5.5 | −6.2947 | 0.0078 |
| CHRNA7 | 2.6535 | 0.0356 | CTD-3157E16.1 | −8.128 | 0.0147 |
| CHST9 | 2.552 | 0.0351 | CTD-3199J23.6 | −2.4948 | 0.045 |
| CILP2 | 1.6472 | 0.0216 | CTD-3222D19.5 | −2.1438 | 0.0393 |
| CKMT2-AS1 | 1.2625 | 0.0395 | CTSL | −1.7327 | 0.0155 |
| CLHC1 | 1.6886 | 0.007 | CXorf21 | −1.9728 | 0.0414 |
| CNKSR1 | 1.3612 | 0.038 | CYP27B1 | −1.4858 | 0.0267 |
| CRB1 | 1.8265 | 0.0334 | CYP2AB1P | −2.1353 | 0.0251 |
| CREB3L4 | 1.5156 | 0.0418 | CYP51A1 | −1.5573 | 0.0478 |
| CRLS1 | 1.2417 | 0.0323 | CYTH4 | −1.6175 | 0.0023 |
| CSMD3 | 1.2117 | 0.0249 | DEFA6 | −3.806 | 0.0242 |
| CTA-250D13.1 | 6.2334 | 0.0013 | DGCR11 | −1.797 | 0.0212 |
| CTA-276F8.1 | 2.0056 | 0.0478 | DLX2-AS1 | −3.3104 | 0.0328 |
| CTA-963H5.5 | 1.6638 | 0.0125 | DNAJC15 | −1.2656 | 0.0348 |
| CTB-107G13.1 | 3.2902 | 0.0135 | DOC2B | −2.1241 | 0.0187 |
| CTB-113I20.2 | 2.0747 | 0.0047 | DPY19L2P3 | −2.9846 | 0.0216 |
| CTB-50L17.10 | 1.2337 | 0.0094 | DUOXA2 | −2.2844 | 0.0469 |
| CTB-92J24.2 | 2.8825 | 0.0339 | DUSP2 | −1.5362 | 0.0494 |
| CTC-260E6.2 | 4.3267 | 0.0122 | EEF1DP3 | −3.324 | 0.0156 |
| CTC-338M12.4 | 1.3389 | 0.0175 | EIF1 | −1.2581 | 0.0487 |
| CTC-338M12.5 | 12.0104 | 0.0003 | EIF1AD | −1.2163 | 0.0296 |
| CTC-398G3.1 | 6.9931 | 0.0205 | EIF4A2P4 | −1.7987 | 0.025 |
| CTC-429P9.2 | 2.1848 | 0.012 | EIF5AL1 | −2.6 | 0.0359 |
| CTC-471J1.11 | 2.2648 | 0.0275 | EPGN | −4.0759 | 0.0187 |
| CTC-487M23.7 | 6.2605 | 0.0371 | ERN1 | −1.3774 | 0.0266 |
| CTC-510F12.7 | 6.5198 | 0.0029 | F13A1 | −1.6901 | 0.0154 |
| CTD-2001J20.1 | 2.0328 | 0.0309 | FABP5P11 | −5.3789 | 0.0438 |
| CTD-2006C1.2 | 1.618 | 0.0204 | FAM106CP | −4.8033 | 0.0427 |
| CTD-2012K14.8 | 2.4699 | 0.0376 | FAM110A | −1.2517 | 0.029 |
| CTD-2014D20.1 | 2.8226 | 0.0436 | FAM133CP | −3.6491 | 0.032 |
| CTD-2020K17.3 | 1.7116 | 0.0434 | FAM222B | −1.2692 | 0.0281 |
| CTD-2024I7.13 | 1.8966 | 0.036 | FAM25C | −3.03 | 0.0126 |
| CTD-2035E11.5 | 4.1215 | 0.0079 | FAS | −1.2048 | 0.0294 |
| CTD-2135D7.2 | 2.0603 | 0.0088 | FCER1A | −1.637 | 0.041 |
| CTD-2228K2.7 | 1.6596 | 0.0298 | FDFT1 | −1.2944 | 0.0494 |
| CTD-2270N23.1 | 3.0982 | 0.0129 | FOSL1 | −2.6253 | 0.0435 |
| CTD-2287O16.5 | 1.4796 | 0.0135 | FRMD8 | −1.4727 | 0.0491 |
| CTD-2331H12.7 | 5.6323 | 0.0111 | GAPDHP1 | −2.547 | 0.0458 |
| CTD-2349P21.12 | 8.9098 | 0.0084 | GAPDHP27 | −1.9115 | 0.0259 |
| CTD-2506P8.6 | 2.4764 | 0.0019 | GDE1 | −1.3859 | 0.039 |
| CTD-2525I3.2 | 3.9317 | 0.0093 | GDPD3 | −1.8155 | 0.045 |
| CTD-2527I21.15 | 1.8261 | 0.0054 | GGCT | −1.3699 | 0.0251 |
| CTD-2540B15.13 | 3.6886 | 0.004 | GJD3 | −3.0081 | 0.0438 |
| CTD-2547G23.4 | 1.5106 | 0.0076 | GNB4 | −1.4989 | 0.0437 |
| CTD-2587H24.10 | 4.0891 | 0.0168 | GNG2 | −1.2776 | 0.0163 |
| CTD-2639E6.4 | 5.8394 | 0.0474 | GPR158 | −2.602 | 0.0328 |

TABLE 5-continued

Differentially Expressed Genes in the Skin Biopsies of Responders Compared to Non-Responders

| Up-regulated in Responders vs. Non-Responders | | | Down-regulated in Responders vs. Non-Responders | | |
| --- | --- | --- | --- | --- | --- |
| Gene Symbol | Fold Change | Raw P-value | Gene Symbol | Fold Change | Raw P-value |
| CTD-2649C14.3 | 6.5391 | 0.0063 | GPR79 | −3.0097 | 0.0335 |
| CTD-3051D23.1 | 2.4294 | 0.0078 | GPRIN3 | −1.3375 | 0.046 |
| CTD-3065J16.9 | 1.6289 | 0.0493 | GREM1 | −1.7682 | 0.016 |
| CTD-3074O7.11 | 10.5596 | 0.0102 | GXYLT1 | −1.4345 | 0.0474 |
| CTD-3162L10.1 | 5.6905 | 0.0116 | HAS2-AS1 | −1.9401 | 0.0454 |
| CTD-3220F14.3 | 2.0572 | 0.0301 | HCFC2 | −1.2044 | 0.0304 |
| CYR61 | 2.3649 | 0.0459 | HCG9P5 | −3.3003 | 0.0242 |
| DAB1 | 2.0248 | 0.0241 | HIATL2 | −1.3945 | 0.0148 |
| DANCR | 1.4654 | 0.0081 | HIRA | −1.207 | 0.0392 |
| DANT2 | 2.2875 | 0.0088 | HIST1H2BF | −3.3669 | 0.0484 |
| DCBLD2 | 1.1272 | 0.0481 | HLA-H | −3.4302 | 0.0438 |
| DDX11 | 1.4888 | 0.0304 | HS6ST1 | −1.3551 | 0.0426 |
| DGCR6 | 1.6421 | 0.0364 | IER2 | −1.4929 | 0.0466 |
| DIAPH2-AS1 | 2.1391 | 0.0343 | IGBP1P3 | −2.193 | 0.0246 |
| DKFZp434J0226 | 2.2245 | 0.0459 | IGKV2-40 | −3.9951 | 0.0154 |
| DMXL2 | 1.1451 | 0.0488 | IGKV2D-40 | −3.9951 | 0.0154 |
| DNAH5 | 1.8002 | 0.0433 | IGSF21 | −1.4287 | 0.0495 |
| DPY19L1 | 1.2872 | 0.0444 | IL17C | −7.7601 | 0.0078 |
| DPY19L1P1 | 2.5398 | 0.0188 | IL17REL | −2.3431 | 0.0153 |
| DRAM2 | 1.3326 | 0.0269 | IL1F10 | −2.034 | 0.0336 |
| DRD1 | 2.7155 | 0.0227 | IL1R1 | −1.272 | 0.0326 |
| DTWD1 | 1.1438 | 0.0389 | IL1RL1 | −2.3738 | 0.0039 |
| DXO | 1.3173 | 0.0431 | IL22 | −4.6849 | 0.0485 |
| DZIP1 | 1.6755 | 0.0033 | IL6R | −1.4486 | 0.0356 |
| EDN1 | 2.3445 | 0.0078 | ING1 | −1.1055 | 0.0326 |
| EEF1A1P30 | 3.7184 | 0.0307 | ISY1-RAB43 | −1.223 | 0.0397 |
| EEF1DP4 | 8.1437 | 0.0009 | ITGAM | −1.3865 | 0.0287 |
| EFCAB10 | 2.6386 | 0.005 | KB-1732A1.1 | −2.4326 | 0.0073 |
| EID2B | 1.5072 | 0.0158 | KCNQ1DN | −1.3184 | 0.0362 |
| EXOC3L1 | 1.4119 | 0.034 | KHNYN | −1.2866 | 0.0233 |
| FABP7 | 5.3437 | 0.0133 | KHSRPP1 | −1.9608 | 0.0012 |
| FAH | 1.3287 | 0.0348 | KLF16 | −1.3231 | 0.0341 |
| FAM118A | 2.1764 | 0.0402 | KRT18P12 | −1.8964 | 0.0044 |
| FAM127B | 1.2301 | 0.0343 | KRT8P26 | −2.546 | 0.0253 |
| FAM195A | 1.4075 | 0.0244 | KRT8P31 | −2.9922 | 0.0127 |
| FAM201A | 3.0558 | 0.0205 | LA16c-325D7.1 | −5.7855 | 0.0196 |
| FAM66A | 5.7705 | 0.0331 | LINC00391 | −1.753 | 0.0356 |
| FAM86B1 | 2.1004 | 0.0454 | LINC00427 | −2.8954 | 0.0269 |
| FAM86B3P | 2.2458 | 0.0395 | LINC00473 | −3.7662 | 0.0185 |
| FAM90A25P | 4.4973 | 0.0359 | LINC00636 | −3.1979 | 0.0391 |
| FCN3 | 1.8711 | 0.0431 | LINC00691 | −2.2011 | 0.0155 |
| FDPSP7 | 8.3565 | 0.0061 | LINC01123 | −1.5817 | 0.0296 |
| FIGF | 2.2665 | 0.0163 | LINC01124 | −2.4742 | 0.0287 |
| FN3KRP | 1.3429 | 0.0121 | LINC01128 | −1.3974 | 0.0303 |
| FRA10AC1 | 1.2076 | 0.0395 | LINC01314 | −2.394 | 0.0331 |
| FSIP2 | 2.0047 | 0.0093 | LIPE-AS1 | −2.1211 | 0.0086 |
| FUCA1P | 3.1216 | 0.0293 | LMAN1L | −3.2538 | 0.0417 |
| G6PC3 | 1.2228 | 0.0461 | LRPAP1 | −1.162 | 0.0407 |
| GAPDHP2 | 3.0393 | 0.0264 | LY6G6C | −1.9073 | 0.0462 |
| GCAT | 1.4044 | 0.0201 | LYNX1 | −2.0703 | 0.0295 |
| GDF9 | 1.9615 | 0.0057 | LYPD2 | −2.6025 | 0.0173 |
| GFI1B | 2.4408 | 0.0349 | MAFB | −1.8596 | 0.0398 |
| GNG12-AS1 | 2.3297 | 0.0403 | MAFG | −1.3478 | 0.0209 |
| GNMT | 2.1451 | 0.0233 | MARK2P9 | −2.6356 | 0.0163 |
| GPHA2 | 3.5075 | 0.0465 | MBL2 | −1.3361 | 0.0265 |
| GPR161 | 1.2867 | 0.0466 | MESDC1 | −1.3281 | 0.0449 |
| GRAPL | 2.9604 | 0.0187 | MGRN1 | −1.153 | 0.0463 |
| GRIK1-AS1 | 2.7962 | 0.0462 | MIDN | −1.371 | 0.0317 |
| GRM6 | 2.4779 | 0.0416 | MLEC | −1.2056 | 0.0398 |
| H1FNT | 5.6038 | 0.0052 | MLK7-AS1 | −2.5552 | 0.0227 |
| HAGH | 1.307 | 0.03 | MLX | −1.1929 | 0.0291 |
| HAPLN4 | 3.0866 | 0.0323 | MMP19 | −1.3527 | 0.0249 |
| HERC2P7 | 8.5535 | 0.0425 | MMP23B | −1.4831 | 0.0261 |
| HES7 | 3.0272 | 0.0226 | MS4A3 | −3.1586 | 0.0012 |
| HIRIP3 | 1.2126 | 0.0111 | MTHFR | −1.5262 | 0.0411 |
| HIST1H1B | 6.4608 | 0.0009 | MTND4P9 | −3.0175 | 0.0014 |
| HIST1H4C | 4.4204 | 0.0445 | MTND6P21 | −4.0358 | 0.0206 |
| HMGB1P3 | 13.4261 | 0.0107 | MVB12A | −1.143 | 0.049 |
| HMGB1P31 | 5.4107 | 0.0025 | MYCBP2-AS2 | −12.3355 | 0.0012 |
| HNRNPA3P11 | 2.8939 | 0.0203 | NACC1 | −1.3653 | 0.0395 |
| HOXA10 | 1.6287 | 0.0486 | NAF1 | −1.368 | 0.044 |
| HOXA-A53 | 1.8739 | 0.0395 | NANOGP9 | −2.0082 | 0.0258 |

TABLE 5-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| HOXB9 | 2.1774 | 0.0308 | NCR3 | −2.5296 | 0.04 |
| HOXC5 | 4.3513 | 0.0001 | NDUFA3P1 | −3.4195 | 0.0249 |
| HRAT92 | 1.9864 | 0.0444 | NDUFV3 | −1.3208 | 0.038 |
| HRG | 3.123 | 0.0353 | NOL6 | −1.2691 | 0.0313 |
| HS6ST2 | 2.045 | 0.0034 | NPHS1 | −2.0818 | 0.015 |
| HSPA8P4 | 2.536 | 0.0411 | NPM1P32 | −2.7026 | 0.0245 |
| HSPB2-C11orf52 | 7.0927 | 0.0143 | NRARP | −1.5232 | 0.035 |
| HTR1F | 2.9523 | 0.0043 | NRIP3 | −1.4788 | 0.017 |
| HYDIN | 3.0076 | 0.01 | NUDT4P2 | −2.4478 | 0.0307 |
| IGHG3 | 11.8657 | 0.0082 | OACYLP | −1.4875 | 0.0254 |
| IL12A | 2.6528 | 0.0208 | ODC1 | −1.7616 | 0.0398 |
| IL1RAPL2 | 3.3478 | 0.0023 | OGFRP1 | −2.9204 | 0.0099 |
| INPP5B | 1.1365 | 0.0179 | OR1C1 | −1.9564 | 0.0249 |
| IP6K2 | 1.1199 | 0.0421 | OR1Q1 | −3.0233 | 0.0251 |
| IPO5P1 | 1.5566 | 0.032 | OR7E99P | −2.618 | 0.0253 |
| KATNBL1P6 | 3.3818 | 0.0342 | OSBP2 | −1.4684 | 0.0458 |
| KB-1184D12.1 | 5.0849 | 0.0228 | P2RX5-TAX1BP3 | −1.7444 | 0.0173 |
| KB-1410C5.5 | 2.1517 | 0.0173 | P2RY10 | −1.7976 | 0.0407 |
| KB-1440D3.14 | 3.6143 | 0.047 | PAPPA | −1.8518 | 0.0071 |
| KB-208E9.1 | 3.108 | 0.0338 | PAX8 | −1.9589 | 0.0455 |
| KCNE5 | 3.2942 | 0.0329 | PCDHGA12 | −2.0445 | 0.0426 |
| KCNMB2-AS1 | 4.0783 | 0.0497 | PHLDA2 | −1.927 | 0.0262 |
| KIAA0087 | 2.645 | 0.0419 | PLA2G12A | −1.3108 | 0.0237 |
| KLC4 | 1.38 | 0.0178 | PLA2G2D | −3.4617 | 0.0092 |
| KLHL12 | 1.1627 | 0.0414 | PLA2G2F | −2.0117 | 0.032 |
| KLHL40 | 2.4503 | 0.0209 | PLA2G4A | −1.3079 | 0.0383 |
| KRBOX4 | 1.3829 | 0.0104 | PLEKHM1 | −1.3099 | 0.0475 |
| KRT41P | 4.0539 | 0.0418 | POM121C | −1.221 | 0.0498 |
| KRT8P33 | 1.6224 | 0.019 | POMGNT2 | −1.2388 | 0.0413 |
| LA16c-380F5.3 | 1.7444 | 0.0396 | PPATP1 | −1.6632 | 0.0264 |
| LAMTOR5-AS1 | 2.0718 | 0.015 | PPP4R4 | −2.0785 | 0.0337 |
| LGALS7 | 6.0975 | 0.0408 | PRKCB | −1.5114 | 0.0406 |
| LHFPL3 | 3.9275 | 0.0448 | PSMC1P4 | −2.6735 | 0.0325 |
| LINC00115 | 1.4179 | 0.0051 | PTCHD3P2 | −2.7009 | 0.0026 |
| LINC00158 | 2.6558 | 0.0264 | PTGES | −1.5442 | 0.0225 |
| LINC00294 | 1.3243 | 0.0034 | QPCT | −1.4142 | 0.0494 |
| LINC00323 | 3.0505 | 0.0432 | RAB5CP2 | −3.0938 | 0.0247 |
| LINC00339 | 1.746 | 0.0019 | RAP1A | −1.1756 | 0.0364 |
| LINC00461 | 1.5114 | 0.0422 | RARRES2P1 | −2.6046 | 0.025 |
| LINC00487 | 3.234 | 0.0222 | RDH13 | −1.2786 | 0.041 |
| LINC00623 | 1.869 | 0.0061 | REPIN1 | −1.1941 | 0.0108 |
| LINC00824 | 4.8236 | 0.0173 | RHOF | −1.5768 | 0.0486 |
| LINC00936 | 1.3793 | 0.0415 | RN7SL138P | −1.6428 | 0.0475 |
| LINC01096 | 3.2345 | 0.0383 | RN7SL172P | −4.3607 | 0.0112 |
| LINC01118 | 4.8708 | 0.006 | RN7SL187P | −3.1309 | 0.0246 |
| LINC01127 | 1.993 | 0.0074 | RN7SL444P | −4.696 | 0.0257 |
| LINC01142 | 2.9423 | 0.0436 | RND1 | −3.327 | 0.0427 |
| LINC01226 | 1.9928 | 0.0348 | RNF121 | −1.1721 | 0.0223 |
| LINC01320 | 4.1246 | 0.01 | RNF216 | −1.2086 | 0.0293 |
| LINC01389 | 5.5821 | 0.0415 | RNF8 | −1.3201 | 0.0093 |
| LINC01431 | 7.8181 | 0.005 | RNFT1P2 | −2.9746 | 0.0485 |
| LINC01543 | 3.4788 | 0.0377 | RP11-1036E20.7 | −1.8823 | 0.025 |
| LLNLR-276E7.1 | 2.7993 | 0.0422 | RP11-1042B17.3 | −2.3145 | 0.0252 |
| LMO3 | 2.0837 | 0.0373 | RP11-108P20.2 | −4.355 | 0.0312 |
| LMOD3 | 2.5343 | 0.0127 | RP11-1112J20.1 | −3.7757 | 0.0246 |
| LRRC38 | 2.256 | 0.0218 | RP11-1148O4.1 | −3.2929 | 0.0134 |
| LRRC4C | 3.0078 | 0.0194 | RP11-1149O23.3 | −1.5379 | 0.0363 |
| LRRFIP1P1 | 1.484 | 0.0377 | RP11-114G22.1 | −3.7487 | 0.0133 |
| LRRN4 | 2.1281 | 0.0442 | RP11-11N7.5 | −6.3744 | 0.024 |
| MAMSTR | 1.4182 | 0.0408 | RP11-121P12.1 | −2.6159 | 0.0304 |
| MARC1 | 2.3166 | 0.0263 | RP11-145O15.2 | −2.2397 | 0.0251 |
| MDP1 | 1.1677 | 0.0492 | RP11-156K13.1 | −4.416 | 0.0452 |
| MEF2C-AS1 | 5.8034 | 0.0071 | RP11-158H5.2 | −2.3684 | 0.0075 |
| METTL24 | 2.374 | 0.0206 | RP11-15E18.1 | −3.2407 | 0.0469 |
| METTL25 | 1.2679 | 0.0116 | RP11-163O19.8 | −1.6472 | 0.0256 |
| MIATNB | 1.3709 | 0.0221 | RP11-177H2.2 | −3.3377 | 0.0242 |
| MPV17L | 1.6067 | 0.0042 | RP1-117B12.4 | −7.4681 | 0.0023 |
| MROH8 | 1.9707 | 0.0252 | RP11-17E2.2 | −1.5583 | 0.0253 |
| MRPS36P5 | 5.172 | 0.0407 | RP11-191L9.5 | −2.5297 | 0.0239 |
| MTMR9LP | 1.6857 | 0.0399 | RP11-196G11.3 | −1.4329 | 0.0434 |
| MTUS1 | 1.3157 | 0.0056 | RP11-213H15.1 | −3.4912 | 0.0279 |
| MUM1 | 1.3847 | 0.0309 | RP11-214O1.1 | −1.9583 | 0.0249 |

TABLE 5-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| MYCT1 | 1.7081 | 0.0389 | RP11-219A15.4 | −4.0655 | 0.0452 |
| MYL12BP2 | 5.481 | 0.0145 | RP11-227G15.8 | −5.4911 | 0.0036 |
| MYO15A | 2.7929 | 0.035 | RP11-235G24.3 | −2.6216 | 0.0242 |
| MYO5BP1 | 2.1272 | 0.049 | RP11-259G18.3 | −31.7282 | 0.0251 |
| NDUFAF4P3 | 4.345 | 0.0497 | RP11-259K15.2 | −2.1494 | 0.0271 |
| NEDD9 | 1.7313 | 0.0361 | RP11-275F13.3 | −4.0652 | 0.0141 |
| NKAIN2 | 3.1616 | 0.0102 | RP1-127L4.7 | −3.0205 | 0.0242 |
| NKAPP1 | 1.8886 | 0.0053 | RP11-285E9.6 | −2.785 | 0.0088 |
| NPHP3-ACAD11 | 4.1917 | 0.0318 | RP11-290C10.1 | −2.7434 | 0.0333 |
| NPHP3-AS1 | 2.1654 | 0.0284 | RP11-2N1.2 | −3.1651 | 0.016 |
| NPIPA5 | 1.8834 | 0.0217 | RP11-314A20.5 | −7.8785 | 0.0153 |
| NPIPB7 | 6.3458 | 0.0296 | RP11-317B17.3 | −6.489 | 0.0018 |
| NPPA | 5.6231 | 0.0268 | RP11-320N7.2 | −4.8109 | 0.0406 |
| NPPA-AS1 | 4.0336 | 0.0381 | RP11-326C3.16 | −1.825 | 0.046 |
| NPY6R | 2.6218 | 0.0172 | RP11-338K17.10 | −1.6645 | 0.0275 |
| NUBPL | 1.2039 | 0.0343 | RP11-339F13.2 | −1.7966 | 0.0281 |
| NUDT11 | 1.5549 | 0.041 | RP11-342L8.2 | −2.658 | 0.0242 |
| NUTF2P6 | 11.9917 | 0.0214 | RP11-349G13.3 | −5.0508 | 0.0014 |
| NUTM2D | 1.4852 | 0.0167 | RP1-134E15.3 | −6.8144 | 0.0392 |
| OCM2 | 5.4227 | 0.0386 | RP11-356C4.5 | −2.7754 | 0.0243 |
| OFD1 | 1.3299 | 0.0105 | RP11-359I18.1 | −4.3154 | 0.0179 |
| OGDHL | 3.0007 | 0.0475 | RP11-359P5.1 | −4.7063 | 0.0425 |
| OLFM5P | 2.5991 | 0.0184 | RP11-367J7.3 | −2.7811 | 0.0112 |
| OR13A1 | 2.5334 | 0.0116 | RP11-380I10.2 | −3.0187 | 0.0481 |
| OXCT1-AS1 | 3.2596 | 0.0289 | RP11-395C3.1 | −7.5973 | 0.0016 |
| PC | 1.6565 | 0.0275 | RP11-399B17.1 | −1.6266 | 0.023 |
| PCDHA3 | 2.2364 | 0.0387 | RP11-417F21.2 | −3.831 | 0.0246 |
| PCDHB2 | 1.7292 | 0.0125 | RP11-426L16.9 | −1.4309 | 0.0243 |
| PCNT | 1.1166 | 0.0268 | RP11-428P16.3 | −2.4204 | 0.0311 |
| PDE7B | 1.3523 | 0.0297 | RP11-430L17.1 | −3.2729 | 0.0288 |
| PLCL1 | 1.4095 | 0.0432 | RP11-432J22.2 | −7.2806 | 0.0011 |
| PLCZ1 | 3.0739 | 0.0073 | RP11-460N20.4 | −4.2125 | 0.0274 |
| PLXNA3 | 1.5513 | 0.0433 | RP11-474C8.7 | −1.8661 | 0.0276 |
| PLXNB3 | 1.5399 | 0.0302 | RP11-476D10.1 | −1.9337 | 0.0249 |
| PNMT | 3.7418 | 0.0226 | RP11-477G18.2 | −3.6808 | 0.0245 |
| POLR1D | 1.1583 | 0.0486 | RP11-483P21.2 | −3.0903 | 0.0325 |
| POT1 | 1.3083 | 0.014 | RP11-484D2.2 | −2.5647 | 0.0444 |
| POU1F1 | 2.1488 | 0.0481 | RP11-512F24.1 | −3.3958 | 0.049 |
| POU3F2 | 1.9745 | 0.0483 | RP11-517P14.2 | −1.979 | 0.0161 |
| PPBP | 7.1474 | 0.0108 | RP11-519G16.5 | −3.6503 | 0.0161 |
| PPEF1 | 1.8898 | 0.0212 | RP11-521M14.2 | −2.078 | 0.0257 |
| PRB1 | 4.3092 | 0.0253 | RP11-523L20.2 | −1.8055 | 0.0059 |
| PRR29-AS1 | 2.0062 | 0.0484 | RP11-565P22.6 | −8.735 | 0.0184 |
| PRSS30P | 4.4472 | 0.0078 | RP11-576N17.3 | −3.6762 | 0.0258 |
| PSIP1 | 1.1945 | 0.0332 | RP11-57B24.1 | −3.2708 | 0.0272 |
| PTCHD4 | 2.7295 | 0.0124 | RP11-588G21.2 | −1.6601 | 0.0086 |
| PTPN5 | 3.5645 | 0.0073 | RP1-15D23.2 | −1.9377 | 0.0242 |
| PWRN1 | 8.4582 | 0.0225 | RP11-618P17.4 | −3.9008 | 0.0286 |
| RAB20 | 1.5835 | 0.0434 | RP11-624J12.1 | −1.4904 | 0.0268 |
| RAB40A | 2.461 | 0.0156 | RP11-631M6.3 | −2.7868 | 0.0301 |
| RAC1P2 | 4.9188 | 0.0409 | RP11-64K12.4 | −4.175 | 0.0129 |
| RAD51C | 1.3297 | 0.0273 | RP11-64K12.9 | −2.7329 | 0.025 |
| RANBP17 | 2.561 | 0.0163 | RP11-651P23.4 | −2.0278 | 0.0097 |
| RBP3 | 2.5509 | 0.007 | RP11-662M24.2 | −7.1912 | 0.0383 |
| RBPMS-AS1 | 1.7816 | 0.0337 | RP11-665C16.9 | −4.3139 | 0.0313 |
| RCOR2 | 1.8101 | 0.0273 | RP11-66D17.5 | −1.9986 | 0.0251 |
| RGPD6 | 2.2919 | 0.0232 | RP11-66N24.7 | −1.8132 | 0.0397 |
| RIBC1 | 1.8431 | 0.0117 | RP11-677M14.2 | −4.9692 | 0.0434 |
| RMDN3 | 1.1394 | 0.0169 | RP11-684B2.3 | −3.2987 | 0.0258 |
| RN7SL145P | 6.4085 | 0.0082 | RP11-685M7.5 | −5.4185 | 0.0326 |
| RN7SL244P | 7.8497 | 0.042 | RP11-687E1.2 | −3.8741 | 0.0254 |
| RN7SL40P | 6.7391 | 0.0105 | RP11-689C9.1 | −2.4187 | 0.0277 |
| RN7SL738P | 7.4784 | 0.0406 | RP11-6O2.2 | −2.1853 | 0.0141 |
| RNASEK-C17orf49 | 42.9147 | 0.001 | RP11-708J19.3 | −6.7589 | 0.001 |
| RNF214 | 1.2124 | 0.0229 | RP11-713M15.1 | −1.4589 | 0.0242 |
| ROBO3 | 1.6024 | 0.0316 | RP11-71L14.4 | −3.8055 | 0.0191 |
| RP1-102E24.10 | 1.9297 | 0.0315 | RP11-733O18.1 | −5.3071 | 0.0173 |
| RP11-101E7.2 | 5.3644 | 0.0165 | RP11-75C10.9 | −1.9538 | 0.0276 |
| RP11-1096G20.5 | 5.4178 | 0.0074 | RP11-7K24.3 | −1.5473 | 0.0272 |
| RP11-109N23.4 | 1.9309 | 0.0357 | RP11-809O17.1 | −2.1246 | 0.0495 |
| RP11-109P11.1 | 1.9931 | 0.0399 | RP11-815N9.2 | −2.7184 | 0.0261 |

TABLE 5-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| RP11-111M22.3 | 1.6899 | 0.0282 | RP11-83B20.9 | −5.2157 | 1.07E−05 |
| RP11-112J3.15 | 11.5744 | 0.0104 | RP11-843P14.1 | −3.7173 | 0.0498 |
| RP11-114H24.2 | 4.1638 | 0.0144 | RP11-85G18.6 | −6.1264 | 0.0058 |
| RP11-1180F24.1 | 5.2683 | 0.0036 | RP11-874G11.1 | −6.1241 | 0.0072 |
| RP11-118K6.3 | 9.8058 | 0.0071 | RP11-876N24.1 | −2.2484 | 0.0272 |
| RP11-126K1.2 | 2.1135 | 0.041 | RP11-8P13.5 | −3.4506 | 0.0267 |
| RP11-1280N14.3 | 3.2111 | 0.0347 | RP11-91J19.3 | −2.1462 | 0.0425 |
| RP11-12D24.10 | 4.8406 | 0.0465 | RP11-93B14.4 | −2.3021 | 0.0268 |
| RP11-133N21.7 | 5.5979 | 0.0251 | RP11-95C14.1 | −1.8446 | 0.0442 |
| RP11-134K13.4 | 6.7984 | 0.0074 | RP11-96D1.8 | −1.4593 | 0.0334 |
| RP11-138A9.2 | 2.1404 | 0.0051 | RP11-96K19.2 | −1.4724 | 0.0443 |
| RP11-13A1.1 | 2.231 | 0.0162 | RP1-212P9.3 | −1.9244 | 0.0434 |
| RP11-141B14.2 | 3.0046 | 0.0485 | RP1-257C22.2 | −2.275 | 0.0474 |
| RP11-143E21.3 | 3.2484 | 0.0364 | RP1-266L20.2 | −10.5717 | 0.0044 |
| RP11-147L13.11 | 1.2068 | 0.0207 | RP13-46H24.1 | −3.7417 | 0.0392 |
| RP11-148B6.1 | 3.8885 | 0.0467 | RP1-39J2.1 | −3.4299 | 0.027 |
| RP11-14K3.7 | 4.4475 | 0.0496 | RP1-63G5.8 | −1.9269 | 0.0404 |
| RP11-155D18.13 | 2.2753 | 0.003 | RP1-63M2.5 | −2.4614 | 0.0242 |
| RP11-159N11.4 | 1.603 | 0.0368 | RP3-332B22.1 | −1.7707 | 0.0251 |
| RP11-15L13.4 | 7.0114 | 0.0074 | RP3-375P9.2 | −2.3387 | 0.0242 |
| RP11-166B2.3 | 1.3902 | 0.0367 | RP4-595K12.2 | −2 | 0.0242 |
| RP11-168F9.2 | 5.4946 | 0.0442 | RP4-673M15.1 | −1.5304 | 0.0367 |
| RP11-176H8.1 | 9.9938 | 0.0099 | RP4-785G19.2 | −3.3209 | 0.0197 |
| RP11-178L8.7 | 4.5636 | 0.0321 | RP5-1055C14.6 | −3.6436 | 0.032 |
| RP11-17E13.2 | 7.3555 | 0.0031 | RP5-1142J19.1 | −4.1907 | 0.005 |
| RP11-180M15.6 | 5.2372 | 0.0204 | RP5-1172N10.2 | −2.7433 | 0.0206 |
| RP11-187C18.3 | 2.1821 | 0.0331 | RP5-1184F4.7 | −3.5888 | 0.0011 |
| RP11-18C24.8 | 9.5163 | 0.0017 | RP5-1185H19.2 | −2.4941 | 0.0433 |
| RP11-190A12.8 | 2.1295 | 0.0486 | RP5-827C21.1 | −4.2057 | 0.0245 |
| RP11-196G11.2 | 10.4886 | 0.0154 | RP5-884C9.2 | −1.6597 | 0.048 |
| RP11-20G6.1 | 9.1202 | 0.0058 | RP5-940F7.2 | −2.9181 | 0.0249 |
| RP11-20I23.7 | 6.2813 | 0.0481 | RP5-940J5.3 | −3.9466 | 0.0213 |
| RP11-217B7.2 | 7.4148 | 0.0188 | RPL21P123 | −3.2173 | 0.0244 |
| RP11-227G15.11 | 5.5171 | 0.0445 | RPL7L1P3 | −6.0251 | 0.0007 |
| RP11-22C11.2 | 1.6044 | 0.0008 | RPS4XP17 | −4.3313 | 0.0344 |
| RP11-230F18.5 | 1.4771 | 0.0479 | RPTOR | −1.287 | 0.0316 |
| RP11-247L20.3 | 4.622 | 0.0458 | S1PR2 | −1.2239 | 0.0353 |
| RP1-124C6.1 | 3.0846 | 0.011 | SENP3-EIF4A1 | −2.0946 | 0.0337 |
| RP11-250B2.5 | 4.5445 | 0.0224 | SERPINA6 | −1.6794 | 0.0257 |
| RP11-251G23.2 | 5.7378 | 0.0222 | SESN2 | −1.4602 | 0.0381 |
| RP11-263K19.4 | 2.4224 | 0.0237 | SFTPA1 | −1.5065 | 0.0267 |
| RP11-276H1.3 | 2.1979 | 0.039 | SLA2 | −1.4884 | 0.0439 |
| RP11-278C7.5 | 1.48 | 0.0366 | SLC23A1 | −1.6532 | 0.0322 |
| RP11-285J16.1 | 1.881 | 0.0152 | SLC25A24P2 | −1.8558 | 0.0378 |
| RP11-286E11.2 | 2.325 | 0.0326 | SLC25A25 | −1.6949 | 0.0218 |
| RP11-286O18.1 | 3.5573 | 0.0393 | SLC25A30 | −1.3295 | 0.0286 |
| RP11-295H24.4 | 2.2466 | 0.0316 | SLC25A44 | −1.3579 | 0.0182 |
| RP11-296O14.3 | 2.6649 | 0.0036 | SLC25A51 | −1.3682 | 0.0453 |
| RP11-297D21.4 | 1.9489 | 0.033 | SLC2A13 | −1.3649 | 0.0079 |
| RP11-303E16.5 | 7.1745 | 0.0007 | SLC52A3 | −1.853 | 0.0295 |
| RP11-303E16.9 | 1.7089 | 0.0319 | SLURP1 | −2.1615 | 0.0222 |
| RP11-305O6.4 | 6.6109 | 0.0092 | SMAP2 | −1.6827 | 0.031 |
| RP11-323F24.4 | 4.7055 | 0.0452 | SMOX | −2.2085 | 0.0392 |
| RP11-325L12.6 | 3.7196 | 0.0349 | SNHG25 | −8.2233 | 0.0292 |
| RP11-325N19.3 | 2.0618 | 0.0138 | SNORA27 | −1.34 | 0.0242 |
| RP11-327J1.9 | 6.8589 | 0.0154 | SNX11 | −1.277 | 0.022 |
| RP11-328C8.4 | 5.0615 | 0.0284 | SOCS3 | −2.1253 | 0.0423 |
| RP11-330M2.4 | 4.1025 | 0.0402 | SORD2P | −2.6253 | 0.0498 |
| RP11-331F9.3 | 3.736 | 0.0436 | SOST | −3.7175 | 0.0492 |
| RP11-33B1.1 | 1.33 | 0.027 | SP5 | −2.8837 | 0.0069 |
| RP11-342A23.2 | 3.9561 | 0.0418 | SPECC1L | −1.237 | 0.0138 |
| RP11-345J4.5 | 1.7509 | 0.0007 | SPRY4-IT1 | −3.9937 | 0.0437 |
| RP11-347C18.5 | 6.6505 | 0.0034 | SPSB2 | −1.2973 | 0.0243 |
| RP11-351I21.11 | 6.192 | 0.0404 | SRP72P1 | −1.7828 | 0.0248 |
| RP11-363N22.3 | 2.9814 | 0.02 | SRSF12 | −1.4387 | 0.044 |
| RP11-374M1.11 | 5.7415 | 0.0448 | SSH1 | −1.3209 | 0.0127 |
| RP11-379F4.7 | 2.3663 | 0.018 | SSX1 | −1.8602 | 0.0279 |
| RP1-137D17.2 | 4.0142 | 0.0479 | ST20-AS1 | −1.2811 | 0.0256 |
| RP11-383C5.8 | 2.6993 | 6.08E−05 | STH | −2.8696 | 0.0242 |
| RP11-386B13.4 | 1.5468 | 0.0473 | STK40 | −1.5894 | 0.0159 |
| RP11-38M8.1 | 3.9112 | 0.0229 | SVILP1 | −1.8331 | 0.0228 |
| RP11-390P2.4 | 1.6343 | 0.0423 | SYT2 | −1.6243 | 0.0188 |

TABLE 5-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| RP11-396C23.2 | 1.7287 | 0.0116 | TAF2 | −1.219 | 0.0303 |
| RP1-13D10.3 | 4.2414 | 0.0491 | TAF5L | −1.2063 | 0.0122 |
| RP11-401P9.7 | 4.0314 | 0.0231 | TCF7 | −1.2109 | 0.0234 |
| RP11-403I13.5 | 3.2776 | 0.0115 | TDRD1 | −4.1139 | 0.0061 |
| RP11-404P21.3 | 4.2608 | 0.0014 | TECPR2 | −1.3235 | 0.0127 |
| RP11-404P21.5 | 4.4422 | 0.0385 | TERF2 | −1.2082 | 0.0429 |
| RP11-407G23.2 | 1.8127 | 0.0439 | THBD | −1.701 | 0.0257 |
| RP11-407N8.5 | 4.6344 | 0.0404 | THEM5 | −1.9478 | 0.0403 |
| RP11-425D17.1 | 8.0478 | 0.0003 | TIMM23B | −1.3644 | 0.0457 |
| RP11-426C22.8 | 4.3509 | 0.0213 | TMED7-TICAM2 | −19.0096 | 0.0044 |
| RP11-443B7.3 | 2.6706 | 0.0391 | TMEM2 | −1.2709 | 0.0458 |
| RP11-448G15.3 | 1.4913 | 0.0405 | TMEM41A | −1.3651 | 0.0358 |
| RP11-464D20.2 | 4.7416 | 0.0451 | TMPPE | −1.8408 | 0.022 |
| RP11-466F5.6 | 2.7968 | 0.0419 | TMPRSS4 | −2.6709 | 0.0427 |
| RP11-467J12.4 | 4.2429 | 0.0455 | TNFRSF10A | −1.6348 | 0.0359 |
| RP11-481J2.4 | 1.8168 | 0.0458 | TNFRSF11B | −1.8224 | 0.0053 |
| RP11-48B3.4 | 2.4459 | 0.045 | TNFSF14 | −2.3802 | 0.0086 |
| RP11-492M23.2 | 4.7089 | 0.0474 | TNFSF8 | −1.9837 | 0.0261 |
| RP11-497H16.9 | 1.7581 | 0.0135 | TOR1A | −1.175 | 0.036 |
| RP11-498C9.15 | 1.6255 | 0.032 | TPM3P6 | −5.2015 | 0.0287 |
| RP11-509A17.3 | 5.3732 | 0.0429 | TPT1P10 | −2.5381 | 0.0253 |
| RP11-511B23.2 | 4.4876 | 0.0388 | TPTE2P2 | −1.5887 | 0.0243 |
| RP11-511H23.2 | 1.4107 | 0.0198 | TRAV12-2 | −4.9822 | 0.0323 |
| RP11-511H9.3 | 4.2438 | 0.0269 | TRAV13-1 | −6.2522 | 0.0488 |
| RP11-51B23.3 | 8.3339 | 0.0108 | TRAV30 | −13.0836 | 0.0005 |
| RP1-151F17.2 | 1.5252 | 0.047 | TRBV12-3 | −12.3315 | 0.0119 |
| RP11-522B15.3 | 3.4675 | 0.0037 | TRBV19 | −2.9847 | 0.0335 |
| RP11-523H24.3 | 9.4036 | 0.0182 | TRBV29-1 | −2.3759 | 0.0222 |
| RP11-525A16.4 | 5.7535 | 0.0487 | TRBV4-1 | −8.0389 | 0.0176 |
| RP11-531F16.4 | 1.7727 | 0.036 | TRBV5-6 | −11.0477 | 0.0055 |
| RP11-543P15.1 | 5.6052 | 0.0279 | TRBV6-5 | −2.8496 | 0.0441 |
| RP11-552F3.12 | 3.2706 | 0.0205 | TRBV6-6 | −7.458 | 0.0353 |
| RP11-553D4.2 | 4.1772 | 0.0486 | TRDV2 | −8.1209 | 0.0081 |
| RP11-556H2.1 | 4.1262 | 0.0472 | TRGV5 | −3.4671 | 0.0465 |
| RP11-55K22.2 | 4.8139 | 0.0243 | TRIM6-TRIM34 | −2.9792 | 0.0258 |
| RP11-562A8.4 | 1.9845 | 0.043 | TTC39A-AS1 | −4.089 | 0.0067 |
| RP11-568J23.5 | 1.4635 | 0.0296 | TTC3-AS1 | −2.6363 | 0.0242 |
| RP11-571M6.18 | 9.1215 | 0.0033 | TTYH3 | −1.2249 | 0.0238 |
| RP11-579D7.8 | 3.5469 | 0.0455 | TUBB2B | −2.1249 | 0.0312 |
| RP11-584P21.2 | 2.9407 | 0.0415 | TUNAR | −1.6423 | 0.0362 |
| RP11-620J15.2 | 1.9119 | 0.0482 | TXLNA | −1.2183 | 0.0435 |
| RP11-624L12.1 | 4.1669 | 0.0392 | UBE2M | −1.2959 | 0.046 |
| RP11-626G11.1 | 3.9771 | 0.0479 | UBQLN4P1 | −2.7562 | 0.0249 |
| RP11-652L8.4 | 4.0692 | 0.019 | UGT1A6 | −1.9308 | 0.0133 |
| RP11-666A8.7 | 3.5804 | 0.016 | USP17L4 | −6.6061 | 0.0165 |
| RP11-667K14.3 | 4.0581 | 0.0267 | VAT1 | −1.6088 | 0.0272 |
| RP11-667M19.5 | 4.3878 | 0.0479 | VCAM1 | −1.6069 | 0.0494 |
| RP11-69L16.6 | 3.3786 | 0.0475 | VDAC1P1 | −3.9387 | 0.045 |
| RP11-70L8.4 | 1.4505 | 0.0281 | VDAC1P13 | −2.331 | 0.0246 |
| RP11-715J22.6 | 1.6678 | 0.0364 | VDR | −1.2612 | 0.0364 |
| RP11-71H17.7 | 4.3099 | 0.0227 | VIPR1-AS1 | −1.8824 | 0.0341 |
| RP11-734K2.4 | 1.3543 | 0.0093 | VLDLR-AS1 | −2.0453 | 0.0344 |
| RP11-767N6.7 | 2.1918 | 0.0004 | VN1R21P | −4.6083 | 0.0385 |
| RP11-777F6.3 | 1.7498 | 0.0239 | VPS26BP1 | −2.1655 | 0.0252 |
| RP11-781P6.1 | 2.6188 | 6.09E−05 | WAPL | −1.336 | 0.0134 |
| RP11-794G24.1 | 3.0232 | 0.0065 | WDR11-AS1 | −2.768 | 0.0009 |
| RP11-795F19.5 | 2.9211 | 0.0083 | WDR20 | −1.1337 | 0.0273 |
| RP11-798G7.5 | 2.8552 | 0.0477 | WFDC12 | −2.7454 | 0.0393 |
| RP11-84C13.2 | 6.5123 | 0.0021 | XCR1 | −2.003 | 0.031 |
| RP11-85O21.2 | 2.1929 | 0.0478 | XKR8 | −1.2512 | 0.0291 |
| RP11-900F13.2 | 3.5841 | 0.0409 | XKRYP1 | −2.7846 | 0.0497 |
| RP11-92C4.6 | 1.9904 | 0.045 | XKRYP2 | −2.7846 | 0.0497 |
| RP1-193H18.2 | 1.5785 | 0.0046 | ZBED6CL | −2.0984 | 0.0112 |
| RP1-193H18.3 | 4.4066 | 0.0138 | ZFP36L2 | −1.2583 | 0.003 |
| RP11-95P13.1 | 7.2306 | 0.0413 | ZNF304 | −1.2591 | 0.0449 |
| RP11-973H7.3 | 1.9268 | 0.0355 | ZNF324 | −1.3607 | 0.0155 |
| RP11-981P6.1 | 2.2707 | 0.0007 | ZNF425 | −1.5692 | 0.0406 |
| RP11-989E6.10 | 1.55 | 0.0428 | ZNF442 | −1.6631 | 0.0178 |
| RP1-20C7.6 | 2.1148 | 0.0455 | ZNF490 | −1.8719 | 0.0429 |
| RP1-278O22.2 | 3.5249 | 0.0488 | ZNF516 | −1.2065 | 0.0494 |
| RP1-30M3.5 | 1.7974 | 0.0264 | ZNF526 | −1.283 | 0.0451 |
| RP13-20L14.4 | 5.2305 | 0.0195 | ZNF623 | −1.3667 | 0.048 |

TABLE 5-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| RP1-39G22.7 | 1.2386 | 0.0273 | ZNF646 | −1.4716 | 0.0201 |
| RP3-331H24.7 | 2.3581 | 0.0435 | ZNF740 | −1.134 | 0.0253 |
| RP3-414A15.10 | 4.0471 | 0.0438 | ZNF80 | −2.3511 | 0.0461 |
| RP3-414A15.11 | 4.578 | 0.01 | ZSCAN32 | −1.2069 | 0.0217 |
| RP3-467K16.7 | 3.2576 | 0.0405 | ZSWIM4 | −1.7451 | 0.0433 |
| RP3-467N11.1 | 1.5738 | 0.0475 | | | |
| RP3-467N11.2 | 4.72 | 0.0123 | | | |
| RP4-568B10.1 | 9.0453 | 0.0011 | | | |
| RP4-635A23.4 | 3.7933 | 0.0194 | | | |
| RP4-635E18.6 | 2.8507 | 0.0277 | | | |
| RP4-651E10.4 | 3.8207 | 0.0408 | | | |
| RP4-668J24.2 | 3.0464 | 0.0025 | | | |
| RP4-669P10.16 | 2.4244 | 0.021 | | | |
| RP4-669P10.20 | 2.8915 | 0.0416 | | | |
| RP4-751H13.5 | 2.0457 | 0.0269 | | | |
| RP5-1007F24.1 | 3.7999 | 0.0247 | | | |
| RP5-1024G6.7 | 1.9638 | 0.0044 | | | |
| RP5-1027G4.3 | 4.2552 | 0.0008 | | | |
| RP5-827C21.4 | 2.2579 | 0.0281 | | | |
| RP5-884M6.1 | 6.0112 | 0.0075 | | | |
| RP5-915N17.11 | 3.6441 | 0.0282 | | | |
| RP5-981O7.2 | 4.5768 | 0.0447 | | | |
| RP5-997D16.2 | 1.325 | 0.0172 | | | |
| RPE65 | 3.0386 | 0.0463 | | | |
| RPL10P15 | 4.9933 | 0.042 | | | |
| RPL31P52 | 7.9006 | 0.0233 | | | |
| RPL35P5 | 5.1446 | 0.0214 | | | |
| RPL36AP43 | 4.8158 | 0.0453 | | | |
| RPLP1P6 | 1.8181 | 0.045 | | | |
| RPS13P2 | 6.3687 | 0.0372 | | | |
| RPS16 | 1.2108 | 0.0411 | | | |
| RPS19P3 | 5.7719 | 0.0207 | | | |
| RPS26P15 | 14.6538 | 0.0038 | | | |
| RUNDC3A-AS1 | 1.8746 | 0.0335 | | | |
| SAA4 | 4.706 | 0.0419 | | | |
| SAMD13 | 1.6762 | 0.0116 | | | |
| SAP30L-AS1 | 5.774 | 0.0219 | | | |
| SCN2B | 1.6992 | 0.0363 | | | |
| SDCCAG8 | 1.2299 | 0.0384 | | | |
| SENCR | 1.9548 | 0.0173 | | | |
| SETP5 | 3.8239 | 0.043 | | | |
| SEZ6 | 1.8238 | 0.0332 | | | |
| SH3RF3 | 1.3671 | 0.0289 | | | |
| SH3YL1 | 1.2804 | 0.0344 | | | |
| SHBG | 3.1944 | 0.0128 | | | |
| SHROOM1 | 1.5507 | 0.0467 | | | |
| SIRT5 | 1.3105 | 0.0246 | | | |
| SLC16A12 | 2.4847 | 0.048 | | | |
| SLC22A15 | 1.3689 | 0.0103 | | | |
| SLC22A5 | 1.4575 | 0.0276 | | | |
| SLC7A9 | 4.5409 | 0.0383 | | | |
| SMAD9 | 1.491 | 0.0027 | | | |
| SMG1P4 | 2.4814 | 0.0226 | | | |
| SNHG24 | 3.3588 | 0.0134 | | | |
| SNX29P1 | 2.5938 | 0.0065 | | | |
| SPAG16 | 1.2969 | 0.0494 | | | |
| SPAG17 | 2.1873 | 0.0466 | | | |
| SPATA31C2 | 1.9712 | 0.019 | | | |
| SPDYE10P | 2.2877 | 0.0116 | | | |
| SPDYE2 | 2.7532 | 0.0213 | | | |
| SPG20-AS1 | 3.4268 | 0.0174 | | | |
| SPICE1 | 1.2244 | 0.0178 | | | |
| SPR | 1.2989 | 0.038 | | | |
| SPX | 6.4913 | 0.0002 | | | |
| SRD5A2 | 2.8112 | 0.0325 | | | |
| SRL | 1.7383 | 0.0157 | | | |
| SRP54-AS1 | 2.0161 | 0.0288 | | | |
| ST20 | 2.0909 | 0.0305 | | | |
| SULT1A2 | 3.7455 | 0.0206 | | | |
| SYCP1 | 2.7 | 0.0288 | | | |
| SYCP2L | 2.7947 | 0.0308 | | | |
| SYDE2 | 2.1356 | 0.0006 | | | |

TABLE 5-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P-value | Gene Symbol | Fold Change | Raw P-value |
| SYN3 | 2.3927 | 0.023 | | | |
| SYNDIG1L | 3.314 | 0.0209 | | | |
| TAL2 | 5.2463 | 0.017 | | | |
| TATDN1 | 1.1392 | 0.0409 | | | |
| TBC1D3C | 4.2921 | 0.0251 | | | |
| TBX18 | 1.5507 | 0.03 | | | |
| Telomerase-vert | 4.4789 | 0.0474 | | | |
| TEX9 | 1.2308 | 0.0312 | | | |
| TGM7 | 2.352 | 0.031 | | | |
| THYN1 | 1.4252 | 0.0267 | | | |
| TIMD4 | 4.6771 | 0.0015 | | | |
| TMC2 | 1.8816 | 0.0437 | | | |
| TMEM133 | 1.4036 | 0.0387 | | | |
| TMEM143 | 1.4661 | 0.0287 | | | |
| TMEM230 | 1.3314 | 0.0289 | | | |
| TMEM42 | 1.2563 | 0.0064 | | | |
| TMPRSS12 | 1.9029 | 0.0192 | | | |
| TNFRSF17 | 3.7755 | 0.0431 | | | |
| TRBV14 | 5.598 | 0.0457 | | | |
| TRIM54 | 3.4453 | 0.0118 | | | |
| TRPC2 | 4.3353 | 0.0089 | | | |
| TSSK5P | 4.9387 | 0.0015 | | | |
| TTC41P | 2.4712 | 0.0114 | | | |
| TTC8 | 1.2761 | 0.0255 | | | |
| TXNP4 | 3.8263 | 0.0424 | | | |
| UAP1L1 | 1.3723 | 0.0217 | | | |
| UBOX5-AS1 | 1.9713 | 0.0445 | | | |
| UGT2B15 | 2.2588 | 0.0493 | | | |
| UPK3BL | 2.0538 | 0.003 | | | |
| UPK3BP1 | 6.7393 | 0.0463 | | | |
| USH2A | 1.3845 | 0.0426 | | | |
| VGLL1 | 2.9219 | 0.0416 | | | |
| VSTM2A | 3.4925 | 0.0389 | | | |
| WDR88 | 2.4767 | 0.0053 | | | |
| WDR93 | 2.2256 | 0.0212 | | | |
| WNT11 | 1.9609 | 0.0337 | | | |
| XRRA1 | 2.2376 | 0.0331 | | | |
| XXbac-BPG299F13.17 | 1.4813 | 0.0046 | | | |
| XXbac-BPGBPG55C20.1 | 7.3854 | 0.0418 | | | |
| ZDHHC8P1 | 1.9753 | 0.0387 | | | |
| ZFYVE19 | 1.291 | 0.0329 | | | |
| ZMYM3 | 1.1954 | 0.0481 | | | |
| ZNF197-AS1 | 6.9865 | 0.0138 | | | |
| ZNF223 | 1.3904 | 0.0146 | | | |
| ZNF230 | 1.2383 | 0.0287 | | | |
| ZNF286B | 1.4222 | 0.0343 | | | |
| ZNF337-AS1 | 1.9462 | 0.0346 | | | |
| ZNF418 | 1.551 | 0.0248 | | | |
| ZNF519 | 1.5835 | 0.0376 | | | |
| ZNF738 | 1.7323 | 0.0066 | | | |
| ZNF76 | 1.1402 | 0.0365 | | | |
| ZNF781 | 2.3146 | 0.0107 | | | |
| ZNF833P | 4.201 | 0.0304 | | | |
| ZSCAN4 | 2.3853 | 0.0177 | | | |
| ZSCAN9 | 1.2702 | 0.0217 | | | |

Example 2: Characterization of Gene Expression During the Course of Treatment

Biopsy and corresponding RNA samples were collected from individuals enrolled in the clinical study of Example 1 at baseline and at day 28. Table 6 lists differentially expressed genes that were significantly modulated (P<0.05) in responders by treatment between baseline and day 28, and therefore represent genomic biomarkers correlative of therapeutic response. Table 7 lists differentially expressed genes that were stably expressed in responders throughout the study and were not significantly modulated by treatment between baseline and day 28.

TABLE 6

Differentially Expressed Genes Significantly Modulated Between Baseline and Day 28

| Increased Expression from Baseline to Day 28 | | | Decreased Expression from Baseline to Day 28 | | |
|---|---|---|---|---|---|
| Gene Symbol | Fold Change | Raw P Value | Gene Symbol | Fold Change | Raw P Value |
| AADACL4 | 1.847 | 0.0382 | AC005224.2 | −1.8311 | 0.0353 |
| ABCA10 | 1.8294 | 0.0092 | AC008074.3 | −3.0438 | 0.0472 |
| ABCC6 | 1.5198 | 0.0157 | AC010733.5 | −1.9037 | 0.0328 |
| AC005519.4 | 1.2799 | 0.0434 | AC092301.3 | −1.8774 | 0.0242 |
| AC009501.4 | 1.4389 | 0.005 | ACAD9 | −1.4261 | 0.0072 |
| AC068831.15 | 3.7149 | 0.0168 | AGAP2 | −1.7002 | 0.0019 |
| AC098820.2 | 2.8328 | 0.0161 | AP000560.3 | −1.8457 | 0.0259 |
| AC144831.3 | 1.7142 | 0.0055 | APOBEC3A | −2.3282 | 0.0125 |
| ANAPC16 | 1.0792 | 0.0253 | AQP3 | −1.9273 | 0.001 |
| APOBEC2 | 3.6603 | 0.0014 | ARC | −2.0896 | 0.0035 |
| AZIN2 | 1.5862 | 0.0033 | ARHGEF5 | −1.3806 | 0.0534 |
| BEND3P1 | 1.7653 | 0.0279 | ARL4D | −1.3901 | 0.0005 |
| BICC1 | 1.6764 | 0.0037 | ASB10 | −2.6299 | 0.0017 |
| BISPR | 1.5644 | 0.0243 | ASPHD2 | −1.4877 | 0.0326 |
| BMPER | 1.4905 | 0.0496 | BCL3 | −1.5504 | 0.005 |
| C16orf58 | 1.1566 | 0.0347 | BZW1P2 | −1.7089 | 0.0244 |
| C1GALT1C1L | 1.6358 | 0.0549 | C17orf96 | −2.6418 | 0.0009 |
| C6orf48 | 1.2615 | 0.0292 | C19orf84 | −2.9833 | 0.0043 |
| CA1 | 2.1701 | 0.0486 | CBARP | −1.9941 | 0.0046 |
| CCBL1 | 1.2099 | 0.0522 | CBLL1 | −1.2184 | 0.0309 |
| CCDC92 | 1.247 | 0.0085 | CCDC34 | −1.4098 | 0.0181 |
| CCNB1IP1 | 1.2034 | 0.0384 | CCL18 | −2.1759 | 0.0284 |
| CCR10 | 1.8624 | 0.0096 | CDKN1A | −1.8699 | 0.0041 |
| CD4 | 1.186 | 0.0035 | CEBPB | −1.6942 | 0.008 |
| CENPVP3 | 2.1182 | 0.0288 | CH17-264B6.3 | −5.1881 | 0.0466 |
| CEP120 | 1.1776 | 0.0432 | CHRNA1 | −2.0721 | 0.0459 |
| CEP290 | 1.4101 | 0.0154 | CIB2 | −1.3691 | 0.0105 |
| CILP2 | 1.8946 | 0.007 | CISH | −1.3571 | 0.0113 |
| CREB3L4 | 1.3377 | 0.053 | CSMD3 | −1.1027 | 0.0152 |
| CTB-107G13.1 | 2.2326 | 0.0119 | CTD-3065J16.9 | −1.3709 | 0.0431 |
| CTD-2014D20.1 | 2.4931 | 0.0166 | CTSL | −1.354 | 0.0117 |
| CTD-2020K17.3 | 1.7191 | 0.0233 | CYP51A1 | −1.4208 | 0.0254 |
| CTD-2287O16.5 | 1.6217 | 0.0004 | DANCR | −1.4176 | 0.007 |
| CTD-2547G23.4 | 1.3388 | 0.0057 | DGCR11 | −1.633 | 0.0042 |
| CTD-3157E16.1 | 10.0328 | 0.0016 | DIAPH2-AS1 | −1.6913 | 0.0355 |
| CTD-3199J23.6 | 2.3137 | 0.0032 | DUSP2 | −1.8263 | 0.0046 |
| RP11-147L13.11 | 1.196 | 0.0053 | MTHFR | −1.3276 | 0.0444 |
| RP11-156K13.1 | 3.9388 | 0.0291 | MVB12A | −1.3029 | 0.0002 |
| RP11-190A12.8 | 1.889 | 0.0451 | MYO5BP1 | −2.1272 | 0.0047 |
| RP11-196G11.2 | 3.1107 | 0.0448 | NACC1 | −1.6559 | 0.0007 |
| RP11-219A15.4 | 1.8983 | 0.0039 | NAF1 | −1.4442 | 0.0055 |
| RP11-227G15.11 | 2.667 | 0.0489 | NDUFV3 | −1.3277 | 0.0049 |
| RP11-230F18.5 | 1.3421 | 0.03 | NOL6 | −1.3677 | 0.000065542 |
| RP11-259K15.2 | 2.5924 | 0.029 | NRARP | −1.4083 | 0.0029 |
| RP11-275F13.3 | 1.8802 | 0.0466 | NUDT4P2 | −1.6877 | 0.0044 |
| RP11-285J16.1 | 1.6276 | 0.0053 | OCM2 | −4.2355 | 0.0138 |
| RP11-295H24.4 | 1.9304 | 0.037 | OSBP2 | −1.6004 | 0.005 |
| RP11-399B17.1 | 1.6218 | 0.0299 | PCNT | −1.2018 | 0.0032 |
| RP11-448G15.3 | 1.7529 | 0.0023 | PHLDA2 | −2.5401 | 0.003 |
| RP11-481J2.4 | 1.6621 | 0.0111 | PLA2G2F | −3.6103 | 0.001 |
| RP11-497H16.9 | 1.4045 | 0.0016 | POM121C | −1.2706 | 0.0058 |
| RP11-522B15.3 | 2.1374 | 0.0162 | PPBP | −2.9756 | 0.0451 |
| RP11-57B24.1 | 2.0972 | 0.0445 | PTGES | −1.3188 | 0.0171 |
| RP11-715J22.6 | 1.698 | 0.0331 | RAC1P2 | −4.0674 | 0.0075 |
| RP11-733O18.1 | 4.8767 | 0.0159 | RAD51C | −1.3688 | 0.017 |
| RP11-734K2.4 | 1.465 | 0.0014 | RBPMS-AS1 | −2.0291 | 0.0149 |
| RP11-85O21.2 | 1.7349 | 0.018 | RDH13 | −1.4715 | 0.0184 |
| RP11-91J19.3 | 2.9601 | 0.0008 | RHOF | −1.6316 | 0.0466 |
| RP11-96D1.8 | 1.8406 | 0.001 | RN7SL138P | −2.8411 | 0.0001 |
| RP11-981P6.1 | 1.4302 | 0.0484 | RND1 | −3.9809 | 0.0012 |
| RP1-212P9.3 | 2.8896 | 0.0185 | RNF8 | −1.2294 | 0.0188 |
| RP1-266L20.2 | 3.5402 | 0.0452 | RP11-109P11.1 | −1.9585 | 0.0356 |

TABLE 6-continued

Differentially Expressed Genes Significantly Modulated Between Baseline and Day 28

| Increased Expression from Baseline to Day 28 | | | Decreased Expression from Baseline to Day 28 | | |
|---|---|---|---|---|---|
| Gene Symbol | Fold Change | Raw P Value | Gene Symbol | Fold Change | Raw P Value |
| RP1-39G22.7 | 1.3084 | 0.0011 | RP11-1149O23.3 | −1.8392 | 0.0029 |
| RP3-331H24.7 | 2.2302 | 0.0189 | RP11-141B14.2 | −3.0046 | 0.0046 |
| RP4-751H13.5 | 1.5051 | 0.0449 | RP11-176H8.1 | −5.6704 | 0.0326 |
| SAMD13 | 1.73 | 0.0115 | RP11-196G11.3 | −1.5647 | 0.0039 |
| SH3RF3 | 1.1691 | 0.0442 | RP11-217B7.2 | −3.5864 | 0.0254 |
| SLC22A15 | 1.203 | 0.0161 | RP1-124C6.1 | −2.1724 | 0.0327 |
| SLC22A5 | 1.4318 | 0.011 | RP11-303E16.5 | −5.8454 | 0.0004 |
| SPRY4-IT1 | 3.5593 | 0.0051 | RP11-305O6.4 | −4.9462 | 0.0015 |
| SULT1A2 | 2.044 | 0.0365 | RP11-345J4.5 | −1.4557 | 0.0109 |
| SYCP1 | 2.1163 | 0.0043 | RP11-407N8.5 | −4.6344 | 0.0056 |
| SYDE2 | 1.4751 | 0.0226 | RP11-519G16.5 | −3.1841 | 0.0209 |
| TBX18 | 2.3262 | 0.0003 | RP11-568J23.5 | −1.9379 | 0.0349 |
| TDRD1 | 1.8034 | 0.0322 | RP11-667M19.5 | −3.3611 | 0.0284 |
| TMEM133 | 1.6074 | 0.0007 | RP11-7K24.3 | −2.035 | 0.0022 |
| TMEM2 | 1.3046 | 0.0039 | RP11-809O17.1 | −2.1102 | 0.0548 |
| TMEM230 | 1.1565 | 0.0448 | RP1-257C22.2 | −2.1079 | 0.0109 |
| TTC3-AS1 | 2.1944 | 0.0434 | RP4-673M15.1 | −1.8988 | 0.0013 |
| UAP1L1 | 1.2247 | 0.0521 | RP5-1027G4.3 | −2.9196 | 0.0003 |
| WDR11-AS1 | 2.3813 | 0.0307 | RP5-1142J19.1 | −2.9841 | 0.0007 |
| XRRA1 | 1.2318 | 0.0518 | RP5-915N17.11 | −3.7412 | 0.0308 |
| XXbac-BPG299F13.17 | 1.8948 | 0.0021 | RP5-997D16.2 | −1.2217 | 0.0278 |
| XXbac-BPGBPG55C20.1 | 3.6482 | 0.0329 | RPS16 | −1.2493 | 0.0164 |
| ZDHHC8P1 | 2.2865 | 0.0019 | SENP3-EIF4A1 | −3.1044 | 0.0192 |
| ZNF223 | 1.3489 | 0.0093 | SESN2 | −1.6613 | 0.00004812 |
| ZNF286B | 1.2651 | 0.0079 | SETP5 | −2.5155 | 0.0295 |
| ZNF418 | 1.5126 | 0.0011 | SLC23A1 | −1.7451 | 0.0022 |
| ZSCAN9 | 1.2496 | 0.037 | SLC25A25 | −1.872 | 0.001 |
| | | | SLC25A44 | −1.4266 | 0.0008 |
| | | | SLC52A3 | −1.823 | 0.001 |
| | | | SLURP1 | −3.2891 | 0.0113 |
| | | | SMAP2 | −1.5274 | 0.0075 |
| | | | SMOX | −2.4418 | 0.0013 |
| | | | SNX11 | −1.3664 | 0.0011 |
| | | | SOCS3 | −2.2831 | 0.0011 |
| | | | SOST | −3.8341 | 0.0301 |
| | | | SPATA31C2 | −1.7457 | 0.03 |
| | | | SPICE1 | −1.1479 | 0.0177 |
| | | | SPR | −1.2808 | 0.0363 |
| | | | STK40 | −1.3136 | 0.0439 |
| | | | TAF2 | −1.1592 | 0.0386 |
| | | | TAF5L | −1.1458 | 0.0054 |
| | | | Telomerase-vert | −3.6394 | 0.0149 |
| | | | TERF2 | −1.2373 | 0.0052 |
| | | | TGM7 | −2.0362 | 0.0387 |
| | | | THBD | −1.9286 | 0.0005 |
| | | | THEM5 | −2.4438 | 0.0086 |
| | | | TMEM41A | −1.414 | 0.0039 |
| | | | TMPRSS4 | −3.5988 | 0.0003 |
| | | | TNFRSF10A | −1.6766 | 0.0009 |
| | | | TOR1A | −1.2186 | 0.0006 |
| | | | TRGV5 | −1.99 | 0.0034 |
| | | | TUBB2B | −1.4424 | 0.011 |
| | | | TXLNA | −1.2848 | 0.0176 |
| | | | TXNP4 | −3.8263 | 0.0038 |
| | | | UBE2M | −1.4611 | 0.0023 |
| | | | UGT1A6 | −1.6266 | 0.0359 |
| | | | VDR | −1.2438 | 0.0363 |
| | | | WAPL | −1.4494 | 0.0017 |
| | | | WDR20 | −1.1131 | 0.0305 |
| | | | WFDC12 | −2.9308 | 0.043 |
| | | | XKR8 | −1.1639 | 0.0374 |
| | | | ZBED6CL | −1.4694 | 0.0088 |
| | | | ZNF324 | −1.3081 | 0.0374 |
| | | | ZNF646 | −1.536 | 0.0017 |
| | | | ZSWIM4 | −1.7802 | 0.0043 |

TABLE 7

Genes Stably Expressed Between Day 1 and Day 28

| Genes Increased But Not Significant | | | Genes Decreased But Not Significant | | |
|---|---|---|---|---|---|
| Gene Symbol | Fold Change | Raw P Value | Gene Symbol | Fold Change | Raw P Value |
| ABCC5 | 1.1102 | 0.4102 | AADAC | −1.6425 | 0.2732 |
| ABHD10 | 1.074 | 0.2229 | AC005083.1 | −1.0553 | 0.6816 |
| AC002480.4 | 1.4069 | 0.3975 | AC005363.9 | −1.0864 | 0.6863 |
| AC003991.3 | 1.5749 | 0.1428 | AC005592.2 | −1.5534 | 0.4649 |
| AC005253.2 | 1.1225 | 0.4333 | AC007041.2 | −1.0369 | 0.944 |
| AC005387.2 | 1.6232 | 0.4957 | AC007163.6 | −1.4368 | 0.5197 |
| AC005481.5 | 1.6957 | 0.0898 | AC009487.6 | −1.3731 | 0.1301 |
| AC006129.3 | 1.4442 | 0.2314 | AC017002.2 | −1.2893 | 0.5094 |
| AC006372.6 | 2.1941 | 0.2937 | AC022819.3 | −1.1234 | 0.7543 |
| AC007036.5 | 2.0339 | 0.1812 | AC025918.2 | −1.4544 | 0.675 |
| AC008132.15 | 1.2439 | 0.5188 | AC058791.1 | −1.0917 | 0.6272 |
| AC009133.17 | 1.2521 | 0.5565 | AC064836.3 | −1.3943 | 0.2694 |
| AC009495.3 | 1.6108 | 0.3517 | AC078852.2 | −2.257 | 0.1583 |
| AC009542.2 | 1.5593 | 0.1434 | AC084809.3 | −1.0473 | 0.9181 |
| AC012146.7 | 1.0934 | 0.5419 | AC091133.1 | −1.5205 | 0.3511 |
| AC012358.8 | 1.1794 | 0.5366 | AC091729.9 | −1.0146 | 0.8696 |
| AC013268.4 | 2.3608 | 0.144 | AC138969.4 | −1.4727 | 0.4034 |
| AC068492.1 | 1.8205 | 0.1716 | AC144449.1 | −1.3365 | 0.3952 |
| AC069155.1 | 1.3161 | 0.5018 | ACKR4 | −1.0339 | 0.833 |
| AC073254.1 | 1.3297 | 0.0821 | ACTN3 | −1.0998 | 0.6046 |
| AC079753.4 | 1.4444 | 0.2573 | AL135745.1 | −4.0862 | 0.1225 |
| AC093690.1 | 1.0968 | 0.794 | ANKRD1 | −1.0487 | 0.8612 |
| AC105760.3 | 1.0974 | 0.4364 | ANKRD52 | −1.1115 | 0.1432 |
| AC108463.2 | 1.3669 | 0.2922 | AP000577.2 | −1.9192 | 0.0899 |
| AC110299.5 | 1.3208 | 0.6427 | AP1S3 | −1.4587 | 0.1688 |
| AC113607.2 | 1 | 1 | APOBR | −1.1631 | 0.1676 |
| AC114765.1 | 1 | 1 | ARHGEF35 | −1.3648 | 0.0567 |
| AC115617.2 | 1.3593 | 0.3187 | ARL5AP3 | −2.2697 | 0.1351 |
| AC131097.4 | 1.1568 | 0.4813 | AUTS2 | −1.0227 | 0.7406 |
| AC132217.4 | 1.268 | 0.7706 | C11orf74 | −1.135 | 0.2485 |
| AC137932.6 | 1.3151 | 0.1959 | C21orf62 | −1.1271 | 0.7289 |
| AC140542.2 | 1.1456 | 0.4154 | C2-AS1 | −2.4274 | 0.0603 |
| AC241585.2 | 1.0089 | 0.9532 | C6orf58 | −1.2865 | 0.4529 |
| ACSM1 | 1.5305 | 0.0764 | C9orf43 | −1.0273 | 0.8065 |
| ACTL6B | 1.2617 | 0.1959 | CASP6 | −1.0894 | 0.1143 |
| ADAM21 | 1.0653 | 0.8518 | CBR3-AS1 | −1.0352 | 0.7172 |
| ADGRL4 | 1.3045 | 0.0807 | CBY1 | −1.0244 | 0.7398 |
| AF131215.9 | 1.2299 | 0.1922 | CCDC150P1 | −1.9823 | 0.1075 |
| AGGF1P6 | 1.8666 | 0.1453 | CCDC184 | −1.0604 | 0.6533 |
| AIFM3 | 1.0846 | 0.6325 | CCDC73 | −1.336 | 0.1599 |
| AKNAD1 | 1.266 | 0.4173 | CD19 | −1.0427 | 0.9258 |
| AL109761.5 | 1.1164 | 0.7544 | CDCA7L | −1.0994 | 0.2068 |
| AMTN | 1.3531 | 0.5963 | CDKN2AIPNL | −1.1501 | 0.1065 |
| AMY2A | 1.6704 | 0.2674 | CHST9 | −1.2512 | 0.461 |
| ANAPC1P1 | 1.4164 | 0.1672 | CRCP | −1.1003 | 0.3419 |
| ANKRD61 | 1.1572 | 0.4989 | CRHR1-IT1 | −1.1934 | 0.0553 |
| ANO4 | 1.2504 | 0.5221 | CRLS1 | −1.0185 | 0.7625 |
| AP000254.8 | 1.4766 | 0.068 | CTA-250D13.1 | −1.3683 | 0.4589 |
| AP000347.4 | 1.1821 | 0.6475 | CTA-373H7.7 | −1.2563 | 0.5695 |
| AP001059.5 | 1.5603 | 0.2175 | CTB-131K11.1 | −1.0889 | 0.1966 |
| AQP11 | 1.1928 | 0.432 | CTB-50L17.10 | −1.0962 | 0.0928 |
| ARHGAP26-AS1 | 1.1428 | 0.5201 | CTC-338M12.5 | −3.059 | 0.0583 |
| ARMC10P1 | 1.1815 | 0.676 | CTC-398G3.1 | −1.5471 | 0.4759 |
| ASIC4 | 1.244 | 0.3772 | CTC-487M23.7 | −2.3371 | 0.2188 |
| BCAT2 | 1.0337 | 0.6996 | CTC-518P12.6 | −1 | 1 |
| BNIP3P5 | 1.9886 | 0.3018 | CTD-2024I7.13 | −1.2277 | 0.4005 |
| BRCC3P1 | 1.4017 | 0.4879 | CTD-2135D7.2 | −1.497 | 0.2205 |
| C10orf35 | 1.0831 | 0.5545 | CTD-2270N23.1 | −2.2968 | 0.0626 |
| C16orf52 | 1.0842 | 0.2359 | CTD-2331H12.7 | −1.0635 | 0.9113 |
| C1orf143 | 1.4633 | 0.1773 | CTD-2349P21.12 | −1.2408 | 0.7232 |
| C1orf220 | 1.171 | 0.6031 | CTD-2503O16.4 | −1.7928 | 0.1386 |
| C1QTNF3-AMACR | 3.3101 | 0.0671 | CTD-2525I3.2 | −1.304 | 0.534 |
| C2orf69P1 | 1.3991 | 0.1653 | CTD-2527I21.15 | −1.0616 | 0.8128 |
| C5AR1 | 1.0692 | 0.7813 | CTD-2540B15.13 | −1.0029 | 0.992 |
| C6orf163 | 1.7096 | 0.1023 | CTD-2583A14.9 | −1.0712 | 0.9137 |
| C6orf52 | 1.0929 | 0.6656 | CTD-2639E6.4 | −1.9413 | 0.4608 |
| C9orf135 | 1 | 1 | CTD-3074O7.11 | −2.7199 | 0.0868 |
| C9orf173-AS1 | 1.4418 | 0.0977 | CTD-3222D19.5 | −1.0541 | 0.8089 |
| CAMK4 | 1.0381 | 0.8387 | CXorf21 | −1.2469 | 0.2774 |
| CAPN12 | 1.1243 | 0.6409 | CYP27B1 | −1.2943 | 0.1033 |
| CCL16 | 2.137 | 0.1212 | DANT2 | −1.4578 | 0.1844 |
| CDC42EP2 | 1.0722 | 0.4941 | DDX11 | −1.0121 | 0.8205 |
| CDH15 | 1.0211 | 0.9155 | DGCR6 | −1.0108 | 0.9264 |
| CDH4 | 1.3484 | 0.1116 | DMXL2 | −1.0308 | 0.6992 |
| CEP164P1 | 1.7341 | 0.0954 | DNAJC15 | −1.0936 | 0.0901 |
| CFAP74 | 1.637 | 0.0934 | DOC2B | −1.2514 | 0.1281 |
| CH17-132F21.5 | 1.2799 | 0.5674 | DPY19L1 | −1.0581 | 0.2912 |
| CH507-216K13.2 | 1.1611 | 0.5694 | DRAM2 | −1.0258 | 0.6446 |
| CHRNA7 | 1.2765 | 0.2348 | DUOXA2 | −1.526 | 0.25 |
| CKMT2-AS1 | 1.173 | 0.1153 | EFCAB10 | −1.107 | 0.5356 |
| CLEC10A | 1.0955 | 0.5459 | EIF5AL1 | −1.333 | 0.1353 |
| CLHC1 | 1.2782 | 0.1316 | EXOC3L1 | −1.0053 | 0.9678 |
| CNKSR1 | 1.0296 | 0.7526 | FABP5P11 | −1.366 | 0.6453 |
| CRB1 | 1.1406 | 0.5348 | FAM106CP | −2.318 | 0.1824 |
| CSF1 | 1.0356 | 0.687 | FAM127B | −1.0623 | 0.3357 |
| CSGALNACT2 | 1.1232 | 0.1765 | FAM133CP | −1.1675 | 0.5178 |
| CTA-276F8.1 | 1.1989 | 0.5621 | FAM25C | −2.1049 | 0.0957 |
| CTA-963H5.5 | 1.1309 | 0.3312 | FDPSP7 | −1.4496 | 0.5038 |
| CTB-113I20.2 | 1.1722 | 0.3231 | G6PC3 | −1.033 | 0.7154 |
| CTB-60E11.9 | 1 | 1 | GAPDHP1 | −1.2403 | 0.3574 |
| CTB-92J24.2 | 1.294 | 0.496 | GAPDHP2 | −1.5363 | 0.211 |
| CTC-260E6.2 | 1.5101 | 0.2282 | GDE1 | −1.2174 | 0.0709 |
| CTC-338M12.4 | 1.1468 | 0.1023 | GFI1B | −1.0905 | 0.8311 |
| CTC-421K24.1 | 1.2907 | 0.553 | GJD3 | −1.8317 | 0.2531 |
| CTC-429P9.2 | 1.0797 | 0.474 | GPR158 | −1.2218 | 0.4942 |
| CTC-459M5.2 | 2.7581 | 0.1498 | GPRIN3 | −1.1232 | 0.1704 |
| CTC-471J1.11 | 1.2873 | 0.0588 | GXYLT1 | −1.0642 | 0.6128 |
| CTC-499J9.1 | 1.5022 | 0.1317 | HAGH | −1.0575 | 0.3833 |
| CTC-510F12.7 | 1.2226 | 0.6928 | HCFC2 | −1.0264 | 0.6943 |
| CTD-2001J20.1 | 1.3911 | 0.3944 | HCG9P5 | −1 | 1 |
| CTD-2006C1.2 | 1.0575 | 0.5393 | HIATL2 | −1.1925 | 0.2455 |
| CTD-2012K14.8 | 1.3227 | 0.1415 | HMGB1P31 | −1.2213 | 0.6662 |
| CTD-2017C7.1 | 2.5443 | 0.0575 | HNRNPA3P11 | −1.6866 | 0.2598 |
| CTD-2035E11.5 | 1.2613 | 0.5921 | HOXA-AS3 | −1.0789 | 0.5434 |
| CTD-2129N1.1 | 1.4469 | 0.4309 | HRG | −1.0424 | 0.9244 |
| CTD-2199O4.7 | 1.4105 | 0.3885 | HS6ST1 | −1.2293 | 0.0631 |
| CTD-2228K2.7 | 1.0904 | 0.6029 | HSPB2-C11orf52 | −1.8649 | 0.3085 |
| CTD-2506P8.6 | 1.2859 | 0.2134 | IGHG3 | −1.103 | 0.894 |
| CTD-2547E10.3 | 1.2239 | 0.7464 | IL17C | −2.1969 | 0.1374 |
| CTD-2587H24.10 | 1.2905 | 0.5289 | IL1R1 | −1.1149 | 0.1452 |
| CTD-2649C14.3 | 1.2787 | 0.5117 | IL1RAPL2 | −1.1951 | 0.6058 |
| CTD-3032H12.1 | 2.8358 | 0.1805 | IL6R | −1.0151 | 0.7523 |
| CTD-3051D23.1 | 1.127 | 0.5713 | ING1 | −1.0023 | 0.9695 |
| CTD-3137H5.5 | 2.6321 | 0.175 | ISY1-RAB43 | −1.1673 | 0.1724 |
| CTD-3162L10.1 | 1.7441 | 0.0746 | KATNBL1P6 | −1.7702 | 0.3915 |
| CTD-3220F14.3 | 1.3267 | 0.4343 | KB-1184D12.1 | −2.0153 | 0.1725 |
| CYP2AB1P | 1 | 1 | KB-1410C5.5 | −1.591 | 0.1738 |
| CYR61 | 1.2345 | 0.3442 | KB-1440D3.14 | −1.1697 | 0.7243 |
| CYTH4 | 1.2394 | 0.0953 | KCNE5 | −1.0673 | 0.8972 |
| DAB1 | 1.3732 | 0.2318 | KCNMB2-AS1 | −1.8533 | 0.26 |

TABLE 7-continued

Genes Stably Expressed Between Day 1 and Day 28

| Genes Increased But Not Significant | | | Genes Decreased But Not Significant | | |
|---|---|---|---|---|---|
| Gene Symbol | Fold Change | Raw P Value | Gene Symbol | Fold Change | Raw P Value |
| DEFA6 | 1.8744 | 0.1924 | KHNYN | −1.069 | 0.4032 |
| DLX2-AS1 | 1.1684 | 0.7298 | KLHL12 | −1.0115 | 0.831 |
| DPY19L1P1 | 1.4289 | 0.0579 | KRT18P12 | −1.1412 | 0.5425 |
| DPY19L2P3 | 1.5192 | 0.1318 | KRT8P26 | −1.0719 | 0.7816 |
| DRD1 | 1.4165 | 0.2206 | KRT8P31 | −1.5056 | 0.2838 |
| DXO | 1.0818 | 0.2178 | KRT8P33 | −1.2631 | 0.2998 |
| EDN1 | 1.357 | 0.0614 | LGALS7 | −1.3773 | 0.0823 |
| EEF1A1P30 | 1.4941 | 0.2647 | LINC00115 | −1.0671 | 0.439 |
| EEF1DP4 | 1.2516 | 0.5798 | LINC00158 | −1.4855 | 0.2681 |
| EIF4A2P4 | 1 | 1 | LINC00487 | −1.631 | 0.1046 |
| F13A1 | 1.4101 | 0.1437 | LINC00623 | −1.0491 | 0.6857 |
| FABP7 | 1.2469 | 0.4699 | LINC00824 | −1.1046 | 0.7737 |
| FAM118A | 1.1692 | 0.0835 | LINC01118 | −1.4358 | 0.5013 |
| FAM195A | 1.1246 | 0.2779 | LINC01123 | −1.337 | 0.1103 |
| FAM201A | 1.4396 | 0.067 | LINC01124 | −1.3884 | 0.2528 |
| FAM66A | 1.4908 | 0.109 | LINC01389 | −2.4079 | 0.0964 |
| FAM86B1 | 1.1589 | 0.2771 | LINC01543 | −1.689 | 0.2565 |
| FAM86B3P | 1.122 | 0.5907 | LIPE-AS1 | −1.1103 | 0.503 |
| FAM90A25P | 1.9935 | 0.1919 | LLNLR-276E7.1 | −1.1338 | 0.7647 |
| FCER1A | 1.1838 | 0.2456 | LRRN4 | −1.128 | 0.5546 |
| FIGF | 1.6087 | 0.075 | MARK2P9 | −1.5179 | 0.1662 |
| FN3KRP | 1.0129 | 0.8216 | MDP1 | −1.0098 | 0.8757 |
| FSIP2 | 1.2766 | 0.2372 | MEF2C-AS1 | −1.1788 | 0.6835 |
| FUCA1P1 | 1.4159 | 0.4387 | METTL25 | −1.0372 | 0.3893 |
| GAPDHP27 | 1.1783 | 0.4246 | MLEC | −1.1119 | 0.215 |
| GDF9 | 1.2268 | 0.1553 | MRPS36P5 | −1.4774 | 0.6042 |
| GNG12-AS1 | 1.2479 | 0.5323 | NKAPP1 | −1.0931 | 0.653 |
| GPHA2 | 1.1803 | 0.5376 | NPHP3-ACAD11 | −1.0088 | 0.982 |
| GPR161 | 1.1682 | 0.1862 | NPHP3-AS1 | −1.3729 | 0.1604 |
| GPR79 | 1.1543 | 0.6442 | ODC1 | −1.2041 | 0.144 |
| GRAPL | 1.8174 | 0.0706 | OGDHL | −1.5218 | 0.1767 |
| GREM1 | 1.4837 | 0.0575 | OGFRP1 | −1.38 | 0.1825 |
| GRIK1-AS1 | 1.1842 | 0.5958 | OLFM5P | −1.2342 | 0.6178 |
| H1FNT | 1.3112 | 0.5635 | OR13A1 | −1.1151 | 0.5385 |
| HAPLN4 | 1.8839 | 0.1317 | P2RY10 | −1.2977 | 0.3315 |
| HAS2-AS1 | 1.0068 | 0.9849 | PAX8 | −1.2636 | 0.3256 |
| HERC2P7 | 2.4804 | 0.0867 | PC | −1.1778 | 0.2651 |
| HES7 | 1.3174 | 0.4033 | PCDHA3 | −1.0321 | 0.9096 |
| HIRIP3 | 1.0562 | 0.3244 | PLA2G12A | −1.1123 | 0.126 |
| HIST1H2BF | 1.4076 | 0.4859 | PLA2G4A | −1.1484 | 0.1653 |
| HLA-H | 1.1886 | 0.4544 | PLCZ1 | −1.8533 | 0.1677 |
| HMGB1P3 | 1.2901 | 0.7126 | PLEKHM1 | −1.1456 | 0.1266 |
| HOXC5 | 1.1144 | 0.4625 | POLR1D | −1.1446 | 0.1093 |
| HSPA8P4 | 1.4439 | 0.2744 | POMGNT2 | −1.1566 | 0.0719 |
| HTR1F | 1.0119 | 0.966 | POU1F1 | −1.6981 | 0.1086 |
| HYDIN | 1.1976 | 0.3593 | POU3F2 | −1.1748 | 0.4483 |
| IGBP1P3 | 1.3087 | 0.1226 | PPP4R4 | −1.309 | 0.1951 |
| IGKV2-40 | 1.3262 | 0.478 | QPCT | −1.2845 | 0.0766 |
| IGKV2D-40 | 1.3262 | 0.478 | RBP3 | −1.2032 | 0.2829 |
| IGSF21 | 1.0252 | 0.8988 | REPIN1 | −1.0867 | 0.168 |
| IL12A | 1.1098 | 0.6023 | RN7SL145P | −2.1586 | 0.1314 |
| IL17REL | 1.2545 | 0.4436 | RN7SL244P | −1.0544 | 0.9358 |
| IL1RL1 | 1.2016 | 0.3551 | RN7SL738P | −4.4362 | 0.0827 |
| INPP5B | 1.0374 | 0.5104 | RNASEK-C17orf49 | −5.0261 | 0.1172 |
| IP6K2 | 1.0194 | 0.6776 | RNF121 | −1.1391 | 0.058 |
| ITGAM | 1.0981 | 0.329 | RNF214 | −1.1307 | 0.0711 |
| KB-208E9.1 | 1.6062 | 0.1012 | RNF216 | −1.0287 | 0.6947 |
| KCNQ1DN | 1.0474 | 0.4072 | RP11-101E7.2 | −1.3542 | 0.4888 |
| KHSRPP1 | 1.3176 | 0.155 | RP11-1096G20.5 | −2.0624 | 0.0985 |
| KIAA0087 | 1.1189 | 0.7792 | RP11-111M22.3 | −1.1051 | 0.53 |
| KRBOX4 | 1.0971 | 0.4441 | RP11-112J3.15 | −1.9476 | 0.477 |
| KRT41P | 1.8042 | 0.3081 | RP11-1180F24.1 | −2.7995 | 0.1233 |
| LA16c-325D7.1 | 1.2974 | 0.5936 | RP11-126K1.2 | −1.8529 | 0.1244 |
| LA16c-380F5.3 | 1.1817 | 0.4874 | RP11-133N21.7 | −1.2454 | 0.707 |
| LAMTOR5-AS1 | 1.0683 | 0.7245 | RP11-143E21.3 | −1.412 | 0.4305 |
| LHFPL3 | 1.0887 | 0.7553 | RP11-14K3.7 | −1.5292 | 0.4151 |
| LINC00323 | 1.7725 | 0.085 | RP11-15L13.4 | −1.3629 | 0.587 |
| LINC00339 | 1.1577 | 0.2514 | RP11-166B2.3 | −1.1917 | 0.1099 |
| LINC00391 | 1.0913 | 0.5914 | RP11-168F9.2 | −2.6341 | 0.1714 |
| LINC00427 | 1 | 1 | RP11-177H2.2 | −1 | 1 |
| LINC00461 | 1.6257 | 0.0852 | RP1-117B12.4 | −1.2502 | 0.6894 |
| LINC00473 | 1.06 | 0.9111 | RP11-187C18.3 | −1.4433 | 0.1066 |
| LINC00636 | 1.0865 | 0.8494 | RP11-18C24.8 | −1.5638 | 0.2886 |
| LINC00691 | 1.1066 | 0.6868 | RP11-191L9.5 | −1.0034 | 0.9918 |
| LINC00936 | 1.1621 | 0.1586 | RP11-213H15.1 | −1.1751 | 0.6531 |
| LINC01096 | 1.3598 | 0.5107 | RP11-22C11.2 | −1.088 | 0.4214 |
| LINC01142 | 1.2465 | 0.5944 | RP11-285E9.6 | −1.6099 | 0.1562 |
| LINC01320 | 1.3942 | 0.5026 | RP11-286E11.2 | −1.0912 | 0.7629 |
| LINC01431 | 1.4709 | 0.3265 | RP11-286O18.1 | −1.9539 | 0.2679 |
| LMAN1L | 1.1425 | 0.7168 | RP11-297D21.4 | −1.0204 | 0.9315 |
| LMOD3 | 1.3358 | 0.3754 | RP11-303E16.9 | −1.2137 | 0.2906 |
| LRRC4C | 1.5745 | 0.0976 | RP11-325N19.3 | −1.3424 | 0.1555 |
| LRRFIP1P1 | 1.2491 | 0.142 | RP11-328C8.4 | −1.2142 | 0.7063 |
| MAMSTR | 1.1374 | 0.2842 | RP11-338K17.10 | −1.2716 | 0.3187 |
| MBL2 | 1.054 | 0.4835 | RP11-342A23.2 | −1.1007 | 0.8727 |
| METTL24 | 1.2056 | 0.5113 | RP1-134E15.3 | −1.527 | 0.604 |
| MIATNB | 1.101 | 0.4778 | RP11-359I18.1 | −1.2825 | 0.4208 |
| MLK7-AS1 | 1.3291 | 0.3209 | RP11-363N22.3 | −1.2632 | 0.5577 |
| MMP19 | 1.1748 | 0.3326 | RP11-374M1.11 | −2.0615 | 0.3485 |
| MPV17L | 1.1321 | 0.2187 | RP11-383C5.8 | −1.1938 | 0.4955 |
| MTND4P9 | 1.1326 | 0.6045 | RP11-38M8.1 | −1.7043 | 0.2353 |
| MTND6P21 | 1.8574 | 0.2057 | RP11-396C23.2 | −1.1745 | 0.3637 |
| MTUS1 | 1.1933 | 0.0561 | RP11-403I13.5 | −1.0837 | 0.7817 |
| MUM1 | 1.199 | 0.1459 | RP11-404P21.3 | −2.1655 | 0.1742 |
| MYCBP2-AS2 | 2.2096 | 0.2635 | RP11-404P21.5 | −3.0474 | 0.0986 |
| MYL12BP2 | 1.0504 | 0.9324 | RP11-417F21.2 | −1 | 1 |
| NANOGP9 | 1.1243 | 0.5259 | RP11-443B7.3 | −1.835 | 0.1488 |
| NCR3 | 1.2557 | 0.5212 | RP11-464D20.2 | −1.3406 | 0.6729 |
| NDUFA3P1 | 2.4873 | 0.1898 | RP11-467J12.4 | −1.5225 | 0.4349 |
| NDUFAF4P3 | 2.4794 | 0.114 | RP11-484D2.2 | −1.2217 | 0.6028 |
| NKAIN2 | 1.4774 | 0.3075 | RP11-492M23.2 | −2.1513 | 0.169 |
| NPHS1 | 1.1602 | 0.4363 | RP11-498C9.15 | −1.0163 | 0.8859 |
| NPIPB7 | 1.136 | 0.8022 | RP11-509A17.3 | −1.3187 | 0.535 |
| NPM1P32 | 1.1607 | 0.5112 | RP11-511H23.2 | −1.1175 | 0.4867 |
| NPPA | 1.4852 | 0.4686 | RP11-511H9.3 | −1.4085 | 0.5931 |
| NPPA-AS1 | 1.2922 | 0.1404 | RP11-523L20.2 | −1.0641 | 0.4768 |
| NPY6R | 1.1534 | 0.5411 | RP11-543P15.1 | −2.3831 | 0.1632 |
| NRIP3 | 1.0418 | 0.7888 | RP11-552F3.12 | −2.4935 | 0.0655 |
| NUBPL | 1.1375 | 0.0627 | RP11-556H2.1 | −1.0593 | 0.8752 |
| NUTF2P6 | 2.8393 | 0.2066 | RP11-55K22.2 | −1.4858 | 0.3969 |
| NUTM2D | 1.1918 | 0.1832 | RP11-562A8.4 | −1.1605 | 0.6711 |
| OACYLP | 1.4466 | 0.1346 | RP11-565P22.6 | −1.5911 | 0.3923 |

TABLE 7-continued

Genes Stably Expressed Between Day 1 and Day 28

| Genes Increased But Not Significant | | | Genes Decreased But Not Significant | | |
|---|---|---|---|---|---|
| Gene Symbol | Fold Change | Raw P Value | Gene Symbol | Fold Change | Raw P Value |
| OFD1 | 1.1153 | 0.3381 | RP11-571M6.18 | −1.2588 | 0.5687 |
| OR1C1 | 1.3093 | 0.208 | RP11-576N17.3 | −1.2916 | 0.46 |
| OR1Q1 | 1.3773 | 0.2354 | RP11-579D7.8 | −1.3965 | 0.4517 |
| OR7E99P | 2.0893 | 0.0904 | RP11-584P21.2 | −1.1226 | 0.7898 |
| OXCT1-AS1 | 1.8818 | 0.0767 | RP11-624L12.1 | −1.1706 | 0.709 |
| P2RX5-TAX1BP3 | 1.0913 | 0.6133 | RP11-626G11.1 | −1.604 | 0.3266 |
| PAPPA | 1.0278 | 0.9324 | RP11-651P23.4 | −1.0337 | 0.8432 |
| PCDHB2 | 1.3686 | 0.0724 | RP11-652L8.4 | −1.5911 | 0.3943 |
| PCDHGA12 | 1.1921 | 0.478 | RP11-662M24.2 | −1.5118 | 0.4617 |
| PLA2G2D | 1.1421 | 0.7096 | RP11-66D17.5 | −1.016 | 0.9457 |
| PLCL1 | 1.2259 | 0.0596 | RP11-677M14.2 | −1.9578 | 0.3638 |
| PNMT | 1.4656 | 0.3301 | RP11-685M7.5 | −1.719 | 0.314 |
| POT1 | 1.0812 | 0.1598 | RP11-69L16.6 | −1.4665 | 0.4283 |
| PPATP1 | 1.1061 | 0.4867 | RP11-70L8.4 | −1.1422 | 0.352 |
| PRB1 | 1.3127 | 0.5006 | RP11-71L14.4 | −1.0498 | 0.8678 |
| PRKCB | 1.0957 | 0.602 | RP11-767N6.7 | −1.1935 | 0.1662 |
| PRR29-AS1 | 1.1218 | 0.729 | RP11-777F6.3 | −1.2868 | 0.4949 |
| PRSS30P | 1.1973 | 0.6702 | RP11-815N9.2 | −1 | 1 |
| PSIP1 | 1.1197 | 0.1229 | RP11-900F13.2 | −1.4318 | 0.5445 |
| PSMC1P4 | 1.2414 | 0.403 | RP1-193H18.3 | −1.2402 | 0.6239 |
| PTCHD3P2 | 1.42 | 0.3105 | RP11-973H7.3 | −1.0151 | 0.9428 |
| PTCHD4 | 1.2047 | 0.568 | RP11-989E6.10 | −1.2554 | 0.1357 |
| PWRN1 | 1.8244 | 0.2565 | RP1-30M3.5 | −1.2983 | 0.1468 |
| RAB40A | 1.2514 | 0.3668 | RP3-414A15.10 | −1.7048 | 0.34 |
| RAB5CP2 | 1 | 1 | RP3-467K16.7 | −1.6406 | 0.1168 |
| RANBP17 | 1.3756 | 0.1452 | RP3-467N11.1 | −1.0804 | 0.3333 |
| RAP1A | 1.0129 | 0.8469 | RP3-467N11.2 | −1.6326 | 0.3814 |
| RARRES2P1 | 1.7494 | 0.1819 | RP4-635A23.4 | −1.4764 | 0.4435 |
| RGPD6 | 1.3363 | 0.212 | RP4-635E18.6 | −2.1184 | 0.2296 |
| RIBC1 | 1.2098 | 0.256 | RP4-651E10.4 | −1.745 | 0.326 |
| RMDN3 | 1.0445 | 0.4411 | RP4-668J24.2 | −1.0294 | 0.9265 |
| RN7SL172P | 1.1429 | 0.8335 | RP4-669P10.16 | −1.4983 | 0.4317 |
| RN7SL187P | 2.1357 | 0.1463 | RP4-785G19.2 | −1.2173 | 0.474 |
| RN7SL40P | 1.043 | 0.8808 | RP5-1024G6.7 | −1.2717 | 0.1677 |
| RN7SL444P | 2.6818 | 0.1636 | RP5-884C9.2 | −1.3104 | 0.152 |
| RNFT1P2 | 1.0104 | 0.968 | RP5-884M6.1 | −1.1761 | 0.7003 |
| RP1-102E24.10 | 1.0071 | 0.9758 | RPL35P5 | −2.4701 | 0.1288 |
| RP11-1036E20.7 | 1 | 1 | RPL36AP43 | −1.6007 | 0.4425 |
| RP11-1042B17.3 | 1.5135 | 0.1788 | RPS13P2 | −1.451 | 0.4846 |
| RP11-108P20.2 | 1.8519 | 0.2099 | RPS19P3 | −1.2996 | 0.5988 |
| RP11-109N23.4 | 1.1325 | 0.6926 | RPS26P15 | −1.9004 | 0.2634 |
| RP11-1112J20.1 | 2.0613 | 0.2819 | RPTOR | −1.1209 | 0.1771 |
| RP11-1148O4.1 | 2.4958 | 0.0907 | RUNDC3A-AS1 | −1.3916 | 0.0974 |
| RP11-114G22.1 | 1.0097 | 0.9674 | S1PR2 | −1.0541 | 0.3677 |
| RP11-114H24.2 | 1.0077 | 0.9873 | SAA4 | −1.3506 | 0.5738 |
| RP11-118K6.3 | 1.3779 | 0.5519 | SAP30L-AS1 | −1.8752 | 0.1128 |
| RP11-121P12.1 | 1.4329 | 0.1296 | SH3YL1 | −1.0288 | 0.4915 |
| RP11-1280N14.3 | 1.6008 | 0.1031 | SHBG | −1.0263 | 0.9188 |
| RP11-12D24.10 | 1.2141 | 0.6954 | SLC25A30 | −1.0707 | 0.3893 |
| RP11-134K13.4 | 1.4882 | 0.2388 | SLC25A51 | −1.0603 | 0.6443 |
| RP11-138A9.2 | 1.4589 | 0.2438 | SNHG24 | −1.3141 | 0.3795 |
| RP11-13A1.1 | 1.563 | 0.1431 | SNHG25 | −1.8698 | 0.4446 |
| RP11-145O15.2 | 2.2464 | 0.0657 | SNX29P1 | −1.3186 | 0.1144 |
| RP11-148B6.1 | 1.1783 | 0.6249 | SORD2P | −1.1924 | 0.5109 |
| RP11-155D18.13 | 1.1539 | 0.431 | SP5 | −1.038 | 0.866 |
| RP11-158H5.2 | 1.4042 | 0.3377 | SPAG17 | −1.3933 | 0.217 |
| RP11-159N11.4 | 1.2164 | 0.2019 | SPDYE2 | −1.4265 | 0.136 |
| RP11-15E18.1 | 1.8651 | 0.163 | SPECC1L | −1.03 | 0.6557 |
| RP11-163O19.8 | 1.168 | 0.502 | SPSB2 | −1.045 | 0.5849 |
| RP11-178L8.7 | 1.0581 | 0.8983 | SRP54-AS1 | −1.2341 | 0.4039 |
| RP11-17E13.2 | 1.5124 | 0.1695 | SSH1 | −1.1488 | 0.0637 |
| RP11-17E2.2 | 1.1105 | 0.4176 | ST20-AS1 | −1.0555 | 0.4748 |
| RP11-180M15.6 | 1.1411 | 0.8125 | SYT2 | −1.2639 | 0.2187 |
| RP11-20G6.1 | 1.8657 | 0.2712 | TAL2 | −1.0227 | 0.9689 |
| RP11-20I23.7 | 2.0064 | 0.3976 | TBC1D3C | −1.1398 | 0.597 |
| RP11-214O1.1 | 1 | 1 | TCF7 | −1.1215 | 0.0902 |
| RP11-227G15.8 | 2.0069 | 0.2595 | TECPR2 | −1.0937 | 0.2474 |
| RP11-235G24.3 | 1 | 1 | TEX9 | −1.1809 | 0.0674 |
| RP11-247L20.3 | 1.0372 | 0.946 | TIMM23B | −1.1981 | 0.1767 |
| RP11-250B2.5 | 1.7744 | 0.0875 | TMPPE | −1.3509 | 0.1313 |
| RP11-251G23.2 | 1.4777 | 0.4648 | TMPRSS12 | −1.4666 | 0.2008 |
| RP11-259G18.3 | 1.6888 | 0.1418 | TNFRSF17 | −1.1777 | 0.6906 |
| RP11-263K19.4 | 1.2638 | 0.3439 | TNFSF14 | −1.0835 | 0.7453 |
| RP11-276H1.3 | 1.0275 | 0.9232 | TNFSF8 | −1.121 | 0.5535 |
| RP11-278C7.5 | 1.1323 | 0.3459 | TRAV13-1 | −1.1234 | 0.8743 |
| RP1-127L4.7 | 1 | 1 | TRBV14 | −1.1689 | 0.8093 |
| RP11-290C10.1 | 1.7643 | 0.1386 | TRBV19 | −1.2485 | 0.5489 |
| RP11-296O14.3 | 1.125 | 0.5318 | TRBV29-1 | −1.2191 | 0.5971 |
| RP11-2N1.2 | 1.6608 | 0.2511 | TRBV6-5 | −1.7502 | 0.1636 |
| RP11-314A20.5 | 1.1543 | 0.8367 | TRBV6-6 | −1.1294 | 0.8514 |
| RP11-317B17.3 | 1.9365 | 0.0964 | TRIM54 | −1.2105 | 0.5246 |
| RP11-320N7.2 | 2.7215 | 0.1273 | TSSK5P | −2.4968 | 0.0601 |
| RP11-323F24.4 | 2.6449 | 0.0563 | TTC39A-AS1 | −1.5625 | 0.4445 |
| RP11-325L12.6 | 1.9227 | 0.2026 | TTYH3 | −1.0345 | 0.6409 |
| RP11-326C3.1 | 1.0575 | 0.8399 | UBOX5-AS1 | −1.1719 | 0.6054 |
| RP11-327J17.9 | 2.4539 | 0.0846 | UBQLN4P1 | −1.4545 | 0.0964 |
| RP11-330M2.4 | 1.3383 | 0.7106 | UGT2B15 | −1.0885 | 0.7986 |
| RP11-331F9.3 | 1.4083 | 0.5052 | UPK3BL | −1.0753 | 0.5455 |
| RP11-339F13.2 | 1.1931 | 0.3422 | USH2A | −1.0994 | 0.4576 |
| RP11-33B1.1 | 1.0011 | 0.9903 | USP17L4 | −2.0096 | 0.1564 |
| RP11-342L8.2 | 1 | 1 | VN1R21P | −1.1771 | 0.8067 |
| RP11-347C18.5 | 1.0251 | 0.9243 | WDR88 | −1.0491 | 0.807 |
| RP11-349G13.3 | 1.9239 | 0.0881 | WNT11 | −1.0056 | 0.9692 |
| RP11-351I21.11 | 1.1123 | 0.7182 | XCR1 | −1.0026 | 0.9888 |
| RP11-356C4.5 | 1.286 | 0.3993 | ZFYVE19 | −1.0251 | 0.7272 |
| RP11-359P5.1 | 1.4405 | 0.528 | ZNF197-AS1 | −2.7687 | 0.0982 |
| RP11-367J7.3 | 1.3398 | 0.3829 | ZNF304 | −1.0077 | 0.8882 |
| RP11-379F4.7 | 1.0444 | 0.8694 | ZNF425 | −1.1462 | 0.2855 |
| RP1-137D17.2 | 1.0789 | 0.8273 | ZNF490 | −1.204 | 0.418 |
| RP11-380I10.2 | 1 | 1 | ZNF516 | −1.0319 | 0.7507 |
| RP11-386B13.4 | 1.3565 | 0.165 | ZNF526 | −1.1342 | 0.0638 |
| RP11-390P2.4 | 1.188 | 0.315 | ZNF623 | −1.1128 | 0.2024 |
| RP11-395C3.1 | 1.8592 | 0.1308 | ZSCAN32 | −1.0409 | 0.5107 |
| RP1-13D10.3 | 1.2014 | 0.5647 | | | |
| RP11-401P9.7 | 1.4634 | 0.2199 | | | |
| RP11-407G23.2 | 1.1076 | 0.6639 | | | |
| RP11-425D17.1 | 1.8386 | 0.1508 | | | |
| RP11-426C22.8 | 1.1331 | 0.7576 | | | |
| RP11-426L16.9 | 1.2263 | 0.1871 | | | |
| RP11-428P16.3 | 2.0979 | 0.2114 | | | |
| RP11-430L17.1 | 1 | 1 | | | |
| RP11-432J22.2 | 1.5275 | 0.338 | | | |
| RP11-460N20.4 | 1.3882 | 0.3857 | | | |
| RP11-466F5.6 | 1.147 | 0.7124 | | | |
| RP11-474C8.7 | 1.4476 | 0.2404 | | | |
| RP11-476D10.1 | 1.4083 | 0.1617 | | | |
| RP11-477G18.2 | 1 | 1 | | | |
| RP11-483P21.2 | 1.3433 | 0.4136 | | | |
| RP11-48B3.4 | 1.2568 | 0.2524 | | | |
| RP11-511B23.2 | 1.0371 | 0.9512 | | | |
| RP11-512F24.1 | 1.0124 | 0.9813 | | | |
| RP11-517F14.2 | 1.1994 | 0.4309 | | | |
| RP11-51B23.3 | 1.315 | 0.7063 | | | |
| RP1-151F17.2 | 1.0533 | 0.7011 | | | |
| RP11-521M14.2 | 1 | 1 | | | |
| RP11-523H24.3 | 1.4146 | 0.6163 | | | |
| RP11-525A16.4 | 1.1554 | 0.8417 | | | |

TABLE 7-continued

Genes Stably Expressed Between Day 1 and Day 28

| Genes Increased But Not Significant | | | Genes Decreased But Not Significant | | |
|---|---|---|---|---|---|
| Gene Symbol | Fold Change | Raw P Value | Gene Symbol | Fold Change | Raw P Value |
| RP11-531F16.4 | 1.2586 | 0.2979 | | | |
| RP11-553D4.2 | 1.4997 | 0.3208 | | | |
| RP11-588G21.2 | 1.3066 | 0.2188 | | | |
| RP1-15D23.2 | 1.1614 | 0.4276 | | | |
| RP11-618P17.4 | 1 | 1 | | | |
| RP11-620J15.2 | 1.1409 | 0.6368 | | | |
| RP11-624J12.1 | 1.5473 | 0.0894 | | | |
| RP11-631M6.3 | 1.518 | 0.2967 | | | |
| RP11-64K12.4 | 1.4785 | 0.2715 | | | |
| RP11-64K12.9 | 1.3323 | 0.381 | | | |
| RP11-665C16.9 | 1.2081 | 0.7483 | | | |
| RP11-666A8.7 | 1.3383 | 0.3623 | | | |
| RP11-667K14.3 | 2.2476 | 0.0628 | | | |
| RP11-66N24.7 | 1.3535 | 0.3554 | | | |
| RP11-684B2.3 | 2.259 | 0.0687 | | | |
| RP11-687E1.2 | 2.3646 | 0.1103 | | | |
| RP11-689C9.1 | 1.529 | 0.208 | | | |
| RP11-6O2.2 | 1.4986 | 0.1393 | | | |
| RP11-708J19.3 | 1.9279 | 0.1725 | | | |
| RP11-713M15.1 | 1.428 | 0.0824 | | | |
| RP11-71H17.7 | 2.032 | 0.1802 | | | |
| RP11-75C10.9 | 1.292 | 0.4566 | | | |
| RP11-781P6.1 | 1.0813 | 0.7084 | | | |
| RP11-794G24.1 | 1.7182 | 0.1405 | | | |
| RP11-795F19.5 | 1.0716 | 0.8137 | | | |
| RP11-798G7.5 | 1.325 | 0.2587 | | | |
| RP11-83B20.9 | 1.2525 | 0.3961 | | | |
| RP11-843P14.1 | 1.3076 | 0.5424 | | | |
| RP11-84C13.2 | 1.1304 | 0.8332 | | | |
| RP11-85G18.6 | 1.4234 | 0.5753 | | | |
| RP11-874G11.1 | 1.7887 | 0.1384 | | | |
| RP11-876N24.1 | 1.7599 | 0.0869 | | | |
| RP11-8P13.5 | 1 | 1 | | | |
| RP11-92C4.6 | 1.2341 | 0.3325 | | | |
| RP11-93B14.4 | 1.1706 | 0.427 | | | |
| RP1-193H18.2 | 1.0874 | 0.2767 | | | |
| RP11-95C14.1 | 1.2775 | 0.3613 | | | |
| RP11-95P13.1 | 1.8219 | 0.3314 | | | |
| RP11-96K19.2 | 1.1291 | 0.5466 | | | |
| RP1-20C7.6 | 1.5442 | 0.074 | | | |
| RP1-278O22.2 | 1.2673 | 0.6355 | | | |
| RP13-20L14.4 | 1.6108 | 0.2568 | | | |
| RP13-46H24.1 | 2.0103 | 0.2372 | | | |
| RP1-39J2.1 | 1.4654 | 0.4527 | | | |
| RP1-63G5.8 | 1.2925 | 0.1871 | | | |
| RP1-63M2.5 | 1 | 1 | | | |
| RP3-332B22.1 | 1.5902 | 0.0713 | | | |
| RP3-375P9.2 | 1.8143 | 0.143 | | | |
| RP3-414A15.11 | 1.6459 | 0.2901 | | | |
| RP4-568B10.1 | 1.7264 | 0.1853 | | | |
| RP4-595K12.2 | 1.2229 | 0.3791 | | | |
| RP4-669P10.20 | 1.543 | 0.1989 | | | |
| RP5-1007F24.1 | 1.8832 | 0.0596 | | | |
| RP5-1055C14.6 | 1.2515 | 0.5497 | | | |
| RP5-1172N10.2 | 1.9901 | 0.1179 | | | |
| RP5-1184F4.7 | 1.596 | 0.1911 | | | |
| RP5-1185H19.2 | 1.6521 | 0.358 | | | |
| RP5-827C21.1 | 1.5475 | 0.4061 | | | |
| RP5-827C21.4 | 1.426 | 0.0793 | | | |
| RP5-940F7.2 | 1 | 1 | | | |
| RP5-940J5.3 | 1.4111 | 0.5507 | | | |
| RP5-981O7.2 | 1.0207 | 0.9317 | | | |
| RPE65 | 1.8342 | 0.1542 | | | |
| RPL10P15 | 1.0016 | 0.9984 | | | |
| RPL21P123 | 1.4432 | 0.3568 | | | |
| RPL31P52 | 1.4158 | 0.5762 | | | |
| RPL7L1P3 | 1.8503 | 0.2154 | | | |
| RPLP1P6 | 1.0632 | 0.7185 | | | |
| RPS4XP17 | 1.9159 | 0.2883 | | | |
| SCN2B | 1.3425 | 0.0982 | | | |
| SDCCAG8 | 1.0259 | 0.8075 | | | |
| SENCR | 1.1089 | 0.5982 | | | |
| SERPINA6 | 1.7249 | 0.1617 | | | |
| SEZ6 | 1.1543 | 0.5491 | | | |
| SFTPA1 | 1.845 | 0.1567 | | | |
| SHROOM1 | 1.0034 | 0.9782 | | | |
| SIRT5 | 1.1288 | 0.334 | | | |
| SLA2 | 1.1162 | 0.4713 | | | |
| SLC16A12 | 1.1326 | 0.6982 | | | |
| SLC25A24P2 | 1 | 1 | | | |
| SLC2A13 | 1.1535 | 0.3146 | | | |
| SLC7A9 | 2.0775 | 0.2493 | | | |
| SMAD9 | 1.2987 | 0.0609 | | | |
| SMG1P4 | 1.2461 | 0.4615 | | | |
| SNORA27 | 1.0893 | 0.3769 | | | |
| SPAG16 | 1.0066 | 0.9336 | | | |
| SPDYE10P | 1.0586 | 0.7938 | | | |
| SPG20-AS1 | 1.5415 | 0.3739 | | | |
| SPX | 1.4516 | 0.1371 | | | |
| SRD5A2 | 1.6019 | 0.2547 | | | |
| SRL | 1.2271 | 0.2186 | | | |
| SRP72P1 | 1.1145 | 0.4395 | | | |
| SRSF12 | 1.1795 | 0.2518 | | | |
| SSX1 | 1.1179 | 0.4312 | | | |
| ST20 | 1.0779 | 0.736 | | | |
| STH | 1.2012 | 0.5262 | | | |
| SVILP1 | 1.2524 | 0.2654 | | | |
| SYCP2L | 1.5941 | 0.108 | | | |
| SYN3 | 2.0012 | 0.0721 | | | |
| SYNDIG1L | 1.7695 | 0.088 | | | |
| TATDN1 | 1.0421 | 0.4099 | | | |
| THYN1 | 1.1734 | 0.0877 | | | |
| TIMD4 | 1.561 | 0.3558 | | | |
| TMC2 | 1.3986 | 0.1763 | | | |
| TMED7-TICAM2 | 2.3163 | 0.2289 | | | |
| TMEM143 | 1.0569 | 0.6301 | | | |
| TMEM42 | 1.1448 | 0.2536 | | | |
| TNFRSF11B | 1.2318 | 0.3501 | | | |
| TPM3P6 | 1.8492 | 0.1962 | | | |
| TPT1P10 | 1.85 | 0.0889 | | | |
| TPTE2P2 | 2.0446 | 0.0762 | | | |
| TRAV12-2 | 1.7017 | 0.4404 | | | |
| TRAV30 | 2.298 | 0.213 | | | |
| TRBV12-3 | 2.7933 | 0.1677 | | | |
| TRBV4-1 | 1.4695 | 0.668 | | | |
| TRBV5-6 | 1.1124 | 0.8693 | | | |
| TRDV2 | 1.3558 | 0.5796 | | | |
| TRIM6-TRIM34 | 1.645 | 0.1701 | | | |
| TRPC2 | 1.4811 | 0.3001 | | | |
| TTC41P | 1.1319 | 0.7564 | | | |
| TTC8 | 1.0848 | 0.2119 | | | |
| TUNAR | 1.1819 | 0.2046 | | | |
| UPK3BP1 | 1.0234 | 0.9511 | | | |
| VAT1 | 1.0112 | 0.9278 | | | |
| VCAM1 | 1.1232 | 0.5066 | | | |
| VDAC1P1 | 1.1009 | 0.8539 | | | |
| VDAC1P13 | 1 | 1 | | | |
| VGLL1 | 1.0284 | 0.9567 | | | |
| VIPR1-AS1 | 1.036 | 0.8531 | | | |
| VLDLR-AS1 | 1.3205 | 0.1734 | | | |
| VPS26BP1 | 1.4495 | 0.1997 | | | |
| VSTM2A | 1.81 | 0.1792 | | | |
| WDR93 | 1.2967 | 0.3176 | | | |
| XKRYP1 | 1.6136 | 0.1276 | | | |
| XKRYP2 | 1.6136 | 0.1276 | | | |
| ZFP36L2 | 1.0485 | 0.3328 | | | |
| ZMYM3 | 1.0117 | 0.86 | | | |
| ZNF230 | 1.1253 | 0.0659 | | | |
| ZNF337-AS1 | 1.1115 | 0.5887 | | | |
| ZNF442 | 1.0865 | 0.5833 | | | |
| ZNF519 | 1.152 | 0.2649 | | | |
| ZNF738 | 1.0201 | 0.866 | | | |

TABLE 7-continued

Genes Stably Expressed Between Day 1 and Day 28

| Genes Increased But Not Significant | | | Genes Decreased But Not Significant | | |
|---|---|---|---|---|---|
| Gene Symbol | Fold Change | Raw P Value | Gene Symbol | Fold Change | Raw P Value |
| ZNF740 | 1.0122 | 0.8326 | | | |
| ZNF76 | 1.0986 | 0.2751 | | | |
| ZNF781 | 1.4483 | 0.2624 | | | |
| ZNF80 | 1.6944 | 0.1458 | | | |
| ZNF833P | 1.2797 | 0.6615 | | | |
| ZSCAN4 | 1.3735 | 0.4578 | | | |

Example 3: Identification of Genes that Predict Therapeutic Benefit to JAK Inhibition at Baseline RNA-sequencing data and genes outlined in Table 7 of Example 2 were utilized to identify genes capable of predicting a therapeutic benefit. Genes were identified by refining the selective criteria to raw p-value <0.01 and absolute fold change >|1.5| (Table 8).

TABLE 8

Genes Capable of Predicting Therapeutic Benefit to JAK inhibition at Baseline

| Up-regulated in Responders | | | Down-regulated in Responders | | |
|---|---|---|---|---|---|
| Gene Symbol | Fold Change | Raw P Value | Gene Symbol | Fold Change | Raw P Value |
| ASIC4 | 3.1041 | 0.0077 | ARHGEF35 | -2.6708 | 0.0009 |
| C10orf35 | 1.7202 | 0.0075 | BNIP3P5 | -8.8373 | 0.008 |
| C6orf58 | 4.3935 | 0.009 | BZW1P2 | -2.4089 | 0.0089 |
| CCDC73 | 1.7066 | 0.0001 | C1QTNF3-AMACR | -7.6974 | 0.0068 |
| CDH15 | 3.2475 | 0.0067 | CAMK4 | -2.8075 | 0.0025 |
| CLHC1 | 1.6886 | 0.007 | CCL18 | -4.4125 | 0.0092 |
| DZIP1 | 1.6755 | 0.0033 | CYTH4 | -1.6175 | 0.0023 |
| EDN1 | 2.3445 | 0.0078 | IL17C | -7.7601 | 0.0078 |
| EEF1DP4 | 8.1437 | 0.0009 | IL1RL1 | -2.3738 | 0.0039 |
| EFCAB10 | 2.6386 | 0.005 | KHSRPP1 | -1.9608 | 0.0012 |
| FDPSP7 | 8.3565 | 0.0061 | KRT18P12 | -1.8964 | 0.0044 |
| FSIP2 | 2.0047 | 0.0093 | LIPE-AS1 | -2.1211 | 0.0086 |
| GDF9 | 1.9615 | 0.0057 | MS4A3 | -3.1586 | 0.0012 |
| H1FNT | 5.6038 | 0.0052 | MTND4P9 | -3.0175 | 0.0014 |
| HMGB1P31 | 5.4107 | 0.0025 | MYCBP2-AS2 | -12.3355 | 0.0012 |
| HS6ST2 | 2.045 | 0.0034 | PAPPA | -1.8518 | 0.0071 |
| HTR1F | 2.9523 | 0.0043 | PLA2G2D | -3.4617 | 0.0092 |
| IGHG3 | 11.8657 | 0.0082 | PTCHD3P2 | -2.7009 | 0.0026 |
| IL1RAPL2 | 3.3478 | 0.0023 | RPL7L1P3 | -6.0251 | 0.0007 |
| LINC00339 | 1.746 | 0.0019 | SP5 | -2.8837 | 0.0069 |
| LINC00623 | 1.869 | 0.0061 | TDRD1 | -4.1139 | 0.0061 |
| LINC01118 | 4.8708 | 0.006 | TMED7-TICAM2 | -19.0096 | 0.0044 |
| LINC01127 | 1.993 | 0.0074 | TNFRSF11B | -1.8224 | 0.0053 |
| MEF2C-AS1 | 5.8034 | 0.0071 | TNFSF14 | -2.3802 | 0.0086 |
| MPV17L | 1.6067 | 0.0042 | TRAV30 | -13.0836 | 0.0005 |
| NKAPP1 | 1.8886 | 0.0053 | TRBV5-6 | -11.0477 | 0.0055 |
| PLCZ1 | 3.0739 | 0.0073 | TRDV2 | -8.1209 | 0.0081 |
| PRSS30P | 4.4472 | 0.0078 | WDR11-AS1 | -2.768 | 0.0009 |
| PTPN5 | 3.5645 | 0.0073 | | | |
| RBP3 | 2.5509 | 0.007 | | | |
| RNASEK-C17orf49 | 42.9147 | 0.001 | | | |
| RPS26P15 | 14.6538 | 0.0038 | | | |
| SNX29P1 | 2.5938 | 0.0065 | | | |
| SYDE2 | 2.1356 | 0.0006 | | | |
| TIMD4 | 4.6771 | 0.0015 | | | |
| TRPC2 | 4.3353 | 0.0089 | | | |
| UPK3BL | 2.0538 | 0.003 | | | |
| WDR88 | 2.4767 | 0.0053 | | | |
| ZNF738 | 1.7323 | 0.0066 | | | |

Example 4: Identification of Genes Differentially Expressed in Patients with Mild to Moderate Plaque Psoriasis that are Complete Responders to Treatment with Ruxolitinib Full thickness skin biopsies were collected from individuals with mild to moderate plaque psoriasis, enrolled in a double-blind, randomized, vehicle controlled dose ranging study of ruxolitinib (INCB018424) for the treatment of plaque psoriasis involving 2-20% of body surface area. All subjects consented to the biopsy collection and met the inclusion and exclusion criteria outlined in the clinical protocol. Once collected, skin biopsies were processed from full tissue into ribonucleic acid (RNA) for further analysis and subsequently analyzed using RNA sequencing. Samples were separated into to two groups based on clinical response to treatment with topical INCB018424 and outlined in Table 9. Specifically, samples were classified as "responder" or "non-responder" based on their therapeutic response at day 84 of treatment (individuals were classified as responders if they had >=50% improvement in psoriasis area severity index on day 84). Individuals were topically applied INCB018424 once daily, at a dose strength of 0.5%, 1.0%, or 1.5% INCB018424 phosphate in a cream formulation.

TABLE 9

Characterization and Classification of Subjects Enrolled in Study.

| Subject ID | Treatment | Classification | % Change in PASI at Day 28 | % Change in PASI at Day 84 |
|---|---|---|---|---|
| 8007 | 0.5% QD | Non-Responder | -23.5 | -23.5 |
| 19020 | 0.5% QD | Responder | -51.7 | -66.7 |
| 19027 | 0.5% QD | Non-Responder | -12.5 | -12.5 |
| 24006 | 0.5% QD | Non-Responder | -27.8 | -45.9 |
| 24008 | 0.5% QD | Responder | -16.7 | -75 |
| 24013 | 0.5% QD | Responder | -16.7 | -50 |
| 10017 | 1.0% QD | Non-Responder | -15.3 | 0 |
| 24003 | 1.0% QD | Responder | 0 | -66.7 |
| 24007 | 1.0% QD | Non-Responder | 83.3 | 77.8 |
| 8013 | 1.5% QD | Non-Responder | -12.6 | -12.6 |
| 8016 | 1.5% QD | Non-Responder | -4.7 | -42.5 |
| 10016 | 1.5% QD | Non-Responder | -28 | -30 |
| 16010 | 1.5% QD | Responder | -50 | -84.8 |
| 21016 | 1.5% QD | Responder | -32 | -64 |
| 8002 | Vehicle | Non-Responder | -5 | 3.8 |
| 8012 | Vehicle | Responder | -8.3 | -83.3 |
| 8014 | Vehicle | Non-Responder | 4.7 | 4.7 |
| 9004 | Vehicle | Non-Responder | -10.4 | -14.3 |
| 21013 | Vehicle | Responder | -55 | -71.7 |
| 21014 | Vehicle | Responder | -49.3 | -59.2 |
| 22012 | Vehicle | Responder | -18.9 | -66 |
| 22014 | Vehicle | Non-Responder | -16.1 | 22.6 |

RNA-sequencing was conducted on all biopsy samples by Beijing Genomics Institute using the Illumina HiSeq 4000 system. Data was then aligned and quality controlled in OmicSoft Array Studio using the Human Genome B38 library. The Fragments Per Kilobase of transcript per Million (FPKM) mapped reads (the relative expression of a transcript) were generated and used in all downstream analysis. Significant differences in differentially expressed genes between groups were identified using ANOVA tests. RNA-sequencing identified a total of 2922 differentially expressed genes between the responder and non-responder groups at baseline. One thousand five hundred eighty-nine genes were increased and 1333 genes were decreased in responders compared to non-responders (Table 10).

TABLE 10

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| AADACL2-AS1 | 7.1111 | 0.0009 | AAGAB | −1.1822 | 0.035 |
| ABCA10 | 1.5321 | 0.0181 | AASDHPPT | −1.325 | 0.0494 |
| ABCA5 | 1.4011 | 0.0498 | ABCC6P1 | −3.6171 | 0.0257 |
| ABCA6 | 2.2231 | 0.0031 | ABCD3 | −1.3337 | 0.011 |
| ABCA9 | 2.2965 | 0.0118 | ABCF1 | −1.2013 | 0.0151 |
| ABCC9 | 1.7371 | 0.0056 | ABCF2 | −1.3241 | 0.0064 |
| ABHD16B | 8.6227 | 0.0348 | ABHD13 | −1.3479 | 0.007 |
| ABI3BP | 1.9352 | 0.0352 | ABLIM1 | −1.4037 | 0.0492 |
| ABLIM3 | 1.7596 | 0.0346 | AC000095.11 | −5.2784 | 0.0338 |
| AC002451.3 | 2.254 | 0.0008 | AC002069.5 | −1.5785 | 0.0333 |
| AC003006.7 | 5.9492 | 0.0015 | AC002310.10 | −3.1775 | 0.0447 |
| AC005301.8 | 2.1687 | 0.0022 | AC004471.9 | −7.0322 | 0.0069 |
| AC005355.3 | 3.0743 | 0.022 | AC005008.3 | −1.6601 | 0.0333 |
| AC005387.3 | 5.3945 | 0.023 | AC005523.2 | −1.2749 | 0.0121 |
| AC005537.2 | 2.6478 | 0.0147 | AC005546.2 | −4.6707 | 0.044 |
| AC005618.8 | 4.347 | 0.0011 | AC005593.2 | −2.82 | 0.0452 |
| AC005754.8 | 4.0051 | 0.0088 | AC005609.20 | −2.2182 | 0.0333 |
| AC006153.3 | 3.2288 | 0.0007 | AC007879.5 | −4.4394 | 0.018 |
| AC007099.1 | 2.0535 | 0.0475 | AC007899.3 | −4.9437 | 0.0229 |
| AC007126.1 | 1.2462 | 0.001 | AC008065.1 | −1.9425 | 0.0333 |
| AC007278.3 | 3.0145 | 0.0459 | AC009133.22 | −2.7197 | 0.0433 |
| AC007283.5 | 8.9534 | 0.0481 | AC010642.1 | −1.718 | 0.033 |
| AC007383.3 | 1.4009 | 0.0281 | AC010969.1 | −2.5006 | 0.0458 |
| AC007405.6 | 2.6571 | 0.0293 | AC011286.1 | −1.8162 | 0.0333 |
| AC009120.6 | 1.9343 | 0.0278 | AC017028.10 | −2.983 | 0.0333 |
| AC010894.3 | 3.3825 | 0.0002 | AC017074.1 | −2.2873 | 0.0333 |
| AC011239.2 | 2.3744 | 0.0043 | AC017104.6 | −5.1963 | 0.0273 |
| AC011551.3 | 4.1303 | 0.0438 | AC022201.5 | −4.4679 | 0.0492 |
| AC011747.3 | 2.8599 | 0.0382 | AC068858.1 | −1.4018 | 0.0333 |
| AC012074.2 | 1.83 | 0.0297 | AC073254.1 | −2.098 | 0.031 |
| AC013275.2 | 4.1821 | 0.0003 | AC093063.2 | −3.5641 | 0.0489 |
| AC017002.2 | 3.7232 | 0.0256 | AC096574.4 | −2.0915 | 0.0477 |
| AC018647.3 | 3.2144 | 0.0224 | AC097533.1 | −4.5309 | 0.0488 |
| AC019117.2 | 5.5997 | 0.0412 | AC124861.1 | −1.8292 | 0.0333 |
| AC022182.1 | 3.1968 | 0.04 | AC135048.13 | −7.4349 | 0.0067 |
| AC024560.2 | 5.373 | 0.0363 | AC138969.4 | −4.7351 | 0.0356 |
| AC069513.4 | 3.1039 | 0.0189 | ACACA | −1.3398 | 0.0447 |
| AC073283.4 | 2.7278 | 0.0413 | ACAD9 | −1.2999 | 0.0443 |
| AC073551.1 | 2.3888 | 0.0027 | ACAT2 | −1.4488 | 0.0489 |
| AC074117.13 | 4.8807 | 0.0124 | ACBD3 | −1.4038 | 0.0346 |
| AC079630.4 | 1.9162 | 0.0385 | ACBD5 | −1.4479 | 0.0188 |
| AC079753.5 | 2.6679 | 0.0359 | ACLY | −1.63 | 0.0077 |
| AC079776.1 | 4.5069 | 0.0141 | ACOX3 | −1.2889 | 0.0254 |
| AC079776.2 | 16.8207 | 0.0000639 | ACSL1 | −1.5483 | 0.0053 |
| AC079988.3 | 2.2264 | 0.049 | ACTL8 | −4.4594 | 0.000039918 |
| AC093585.6 | 5.0212 | 0.0377 | ACTRT1 | −1.5927 | 0.0333 |
| AC093627.8 | 3.1443 | 0.0283 | AEBP2 | −1.4736 | 0.0186 |
| AC093642.1 | 2.6845 | 0.0248 | AFTPH | −1.2432 | 0.0408 |
| AC097359.2 | 4.2716 | 0.0407 | AGBL5-IT1 | −5.7091 | 0.0153 |
| AC097713.4 | 3.3872 | 0.0468 | AGFG1 | −1.5134 | 0.0358 |
| AC098828.2 | 3.6485 | 0.0039 | AGGF1 | −1.272 | 0.0344 |
| AC104667.3 | 4.5276 | 0.0383 | AGPAT3 | −1.1929 | 0.0442 |
| AC104809.2 | 2.5301 | 0.0112 | AHCYL1 | −1.2503 | 0.0368 |
| AC104809.4 | 2.3175 | 0.0331 | AK3P3 | −4.7987 | 0.0268 |
| AC106869.2 | 4.5317 | 0.025 | AK4 | −1.4377 | 0.0168 |
| AC108488.4 | 2.3347 | 0.0368 | AKR1C6P | −1.476 | 0.0333 |
| AC108676.1 | 2.148 | 0.0179 | AKT2 | −1.3459 | 0.042 |
| AC113188.2 | 12.8157 | 0.0328 | ALDH2 | −1.264 | 0.0187 |
| AC113189.5 | 1.6937 | 0.0107 | ALG11 | −1.2501 | 0.0377 |
| AC131097.4 | 4.2732 | 0.0325 | ALG2 | −1.1911 | 0.0149 |
| AC144525.1 | 4.0633 | 0.014 | ALOX12P2 | −1.8964 | 0.0425 |
| AC147651.1 | 4.1853 | 0.0132 | ALS2 | −1.1929 | 0.0199 |
| AC156455.1 | 3.2704 | 0.0065 | AMD1 | −1.4185 | 0.0177 |
| AC234582.2 | 3.6951 | 0.0261 | AMHR2 | −2.3573 | 0.0311 |
| ACCS | 2.0192 | 0.0067 | AMMECR1 | −1.6384 | 0.0048 |
| ACKR4 | 1.4087 | 0.0336 | ANKEF1 | −1.6111 | 0.0058 |
| ACO1 | 1.2051 | 0.022 | ANKHD1-EIF4EBP3 | −1.3186 | 0.0231 |
| ACSL6 | 2.0445 | 0.0425 | ANKRD17 | −1.3909 | 0.0205 |
| ACSM5 | 2.9535 | 0.0131 | ANKRD27 | −1.262 | 0.0332 |
| ACTL7B | 1.5958 | 0.0265 | AP000350.6 | −3.404 | 0.0344 |
| ACYP2 | 1.2265 | 0.0426 | AP000648.5 | −1.7164 | 0.0054 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| AD000671.6 | 1.6921 | 0.0164 | AP000797.4 | −1.7097 | 0.0333 |
| ADAM32 | 2.5423 | 0.0418 | AP000892.4 | −3.8055 | 0.0383 |
| ADAM33 | 2.4346 | 0.0222 | AP001610.5 | −4.0659 | 0.05 |
| ADAMTS10 | 2.2932 | 0.0235 | AP1B1 | −1.3189 | 0.0469 |
| ADAMTS12 | 2.1708 | 0.0099 | AP4E1 | −1.3445 | 0.0177 |
| ADAMTS5 | 1.7888 | 0.0202 | APLP2 | −1.2752 | 0.0475 |
| ADGRD1 | 2.8957 | 0.0187 | APOBEC3A | −3.9969 | 0.0208 |
| ADGRE1 | 2.3078 | 0.0231 | APPBP2 | −1.2659 | 0.0122 |
| ADGRF5 | 1.4469 | 0.0277 | APPL1 | −1.3188 | 0.0208 |
| ADGRG5 | 1.6029 | 0.0405 | AREG | −2.2203 | 0.0172 |
| ADH1B | 3.8741 | 0.014 | AREL1 | −1.1558 | 0.0068 |
| ADH1C | 4.5597 | 0.0207 | ARF3 | −1.2675 | 0.0148 |
| ADH4 | 4.74 | 0.005 | ARF6 | −1.2301 | 0.0111 |
| AEBP1 | 1.9272 | 0.0212 | ARFGEF1 | −1.3666 | 0.0468 |
| AF038458.5 | 4.8774 | 0.0167 | ARFGEF2 | −1.2936 | 0.0329 |
| AF064858.8 | 2.163 | 0.0296 | ARFIP1 | −1.3251 | 0.0338 |
| AF131217.1 | 1.9248 | 0.0078 | ARHGAP23 | −1.2746 | 0.0207 |
| AFAP1 | 1.4868 | 0.0244 | ARHGEF18 | −1.2098 | 0.0338 |
| AFF3 | 1.6675 | 0.0465 | ARHGEF34P | −3.0193 | 0.0182 |
| AGAP11 | 2.15 | 0.0055 | ARID3C | −4.0456 | 0.0062 |
| AGTR1 | 2.0287 | 0.0437 | ARIH1 | −1.1753 | 0.0368 |
| AJ006998.2 | 2.7346 | 0.0143 | ARL1 | −1.2582 | 0.0285 |
| AK5 | 1.8884 | 0.0319 | ARL6IP1 | −1.2335 | 0.0236 |
| AKAP14 | 4.8138 | 0.0013 | ARMC3 | −1.4654 | 0.0308 |
| AL035610.1 | 3.4722 | 0.0441 | ARMT1 | −1.4187 | 0.0147 |
| AL137860.1 | 2.8886 | 0.0322 | ARPC1A | −1.1706 | 0.0435 |
| ALPK2 | 3.2812 | 0.0293 | ARSD-AS1 | −3.2382 | 0.0396 |
| AMT | 2.0284 | 0.0446 | ASB9P1 | −2.4624 | 0.0463 |
| ANKAR | 1.9593 | 0.0066 | ASH2L | −1.1769 | 0.0329 |
| ANKRD13B | 1.2859 | 0.0456 | ASNSD1 | −1.1712 | 0.0441 |
| ANKRD18CP | 2.3036 | 0.0047 | ASXL2 | −1.642 | 0.0108 |
| ANKRD36 | 1.5976 | 0.0318 | ATAD2B | −1.2689 | 0.0263 |
| ANKRD6 | 1.4451 | 0.043 | ATE1 | −1.2965 | 0.0426 |
| ANKRD62P1 | 2.7652 | 0.0169 | ATF6 | −1.2849 | 0.0331 |
| ANKS1B | 3.1037 | 0.0016 | ATG4A | −1.2467 | 0.0077 |
| ANXA13 | 3.7458 | 0.015 | ATMIN | −1.2596 | 0.0268 |
| ANXA2R | 1.9872 | 0.0103 | ATP10D | −1.6345 | 0.0118 |
| ANXA6 | 1.6792 | 0.0098 | ATP11B | −1.5706 | 0.0337 |
| AP000255.6 | 7.9874 | 0.0048 | ATP1B3-AS1 | −4.7988 | 0.0488 |
| AP000347.4 | 2.8484 | 0.044 | ATP5G1P1 | −1.895 | 0.0333 |
| AP000439.2 | 3.1522 | 0.0172 | ATP6V0D1 | −1.2396 | 0.0442 |
| AP000473.5 | 3.9336 | 0.0124 | ATP6V1A | −1.328 | 0.024 |
| AP001055.6 | 4.3629 | 0.0121 | ATP6V1B2 | −1.3709 | 0.0193 |
| AP001062.8 | 6.4414 | 0.028 | ATP6V1C1 | −1.2941 | 0.0487 |
| AP001604.3 | 1.7123 | 0.0235 | ATP6V1D | −1.2301 | 0.0116 |
| AP001627.1 | 4.8505 | 0.0159 | ATP6V1H | −1.228 | 0.0381 |
| APOA1 | 2.1164 | 0.0122 | ATXN2 | −1.2835 | 0.0149 |
| APOB | 1.9821 | 0.0317 | ATXN3L | −1.3129 | 0.0333 |
| APOBEC3C | 1.2279 | 0.0375 | ATXN7L3 | −1.1868 | 0.0155 |
| ARHGAP22 | 1.709 | 0.0051 | ATXN7L3B | −1.2378 | 0.002 |
| ARHGAP23P1 | 3.7111 | 0.0441 | B3GALNT2 | −1.5685 | 0.0355 |
| ARHGAP4 | 1.7526 | 0.0477 | B3GNT6 | −2.2157 | 0.0325 |
| ARHGAP6 | 1.9514 | 0.0024 | BAG3 | −1.3414 | 0.0382 |
| ARHGEF10 | 1.3754 | 0.0047 | BAHD1 | −1.2169 | 0.0229 |
| ARHGEF17 | 1.6249 | 0.012 | BANP | −1.3707 | 0.0114 |
| ARHGEF25 | 2.3061 | 0.0009 | BAZ1A | −1.2817 | 0.0446 |
| ARL2-SNX15 | 7.7878 | 0.0181 | BAZ1B | −1.3453 | 0.0427 |
| ARMCX7P | 1.7504 | 0.019 | BBS7 | −1.2223 | 0.0008 |
| ARRDC2 | 1.3541 | 0.0376 | BCKDHA | −1.2826 | 0.0417 |
| ARX | 2.6215 | 0.0052 | BCL2L13 | −1.225 | 0.0446 |
| ASB16-AS1 | 1.4678 | 0.0291 | BCL2L2 | −1.3051 | 0.0419 |
| ASTN2 | 2.1553 | 0.0149 | BCRP7 | −1.7131 | 0.0333 |
| ATP8A1 | 1.4135 | 0.0186 | BDP1 | −1.4023 | 0.0484 |
| B3GLCT | 1.248 | 0.0039 | BICD2 | −1.3733 | 0.0447 |
| BAK1P1 | 3.7166 | 0.0112 | BIRC6 | −1.3646 | 0.0277 |
| BARHL1 | 2.98 | 0.0012 | BLZF1 | −1.6016 | 0.0135 |
| BBC3 | 1.5387 | 0.0266 | BMS1 | −1.1842 | 0.0294 |
| BCAR3 | 1.5504 | 0.0352 | bP-21201H5.1 | −2.5387 | 0.0266 |
| BEX1 | 4.4554 | 0.0338 | BPNT1 | −1.3569 | 0.0037 |
| BEX5 | 1.9185 | 0.0431 | BRAP | −1.1622 | 0.014 |
| BGN | 1.9832 | 0.0055 | BRCC3 | −1.2204 | 0.0206 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
| --- | --- | --- | --- | --- | --- |
| Gene Symbol | Fold Change | Raw P Value | Gene Symbol | Fold Change | Raw P Value |
| BHLHE41 | 1.932 | 0.0031 | BRD7 | −1.1833 | 0.0323 |
| BICC1 | 1.8398 | 0.0378 | BRI3BP | −1.5095 | 0.0292 |
| BRINP3 | 3.2068 | 0.0103 | BRWD1 | −1.0917 | 0.0344 |
| BZRAP1 | 1.8332 | 0.0018 | BTBD10 | −1.3564 | 0.0309 |
| BZRAP1-AS1 | 1.9769 | 0.0379 | BTBD3 | −1.1964 | 0.0339 |
| C10orf10 | 2.1521 | 0.048 | BTBD7 | −1.2285 | 0.0401 |
| C12orf40 | 1.5395 | 0.0024 | BTF3P10 | −2.1501 | 0.0333 |
| C12orf54 | 2.099 | 0.0419 | BTF3P6 | −3.8812 | 0.0386 |
| C12orf76 | 1.2649 | 0.0454 | BZW1P2 | −2.0274 | 0.0278 |
| C14orf159 | 1.2337 | 0.0148 | C10orf95 | −1.584 | 0.0254 |
| C1orf143 | 3.8593 | 0.0085 | C11orf57 | −1.1599 | 0.0235 |
| C1orf53 | 1.5814 | 0.0345 | C11orf58 | −1.4017 | 0.0111 |
| C1QTNF3 | 1.9354 | 0.0223 | C12orf29 | −1.4122 | 0.0061 |
| C1QTNF6 | 1.9568 | 0.0459 | C14orf1 | −1.3223 | 0.0451 |
| C1RL | 1.2289 | 0.0485 | C14orf119 | −1.2495 | 0.0353 |
| C2 | 2.0027 | 0.0371 | C18orf8 | −1.1829 | 0.0466 |
| C20orf96 | 1.634 | 0.021 | C1orf100 | −1.7696 | 0.0333 |
| C21orf2 | 1.4481 | 0.0217 | C1orf43 | −1.1469 | 0.0198 |
| C2orf61 | 2.4121 | 0.0296 | C2orf47 | −1.2263 | 0.0294 |
| C2orf91 | 4.002 | 0.0137 | C2orf49 | −1.4071 | 0.0065 |
| C3 | 2.0621 | 0.0335 | C5orf22 | −1.2725 | 0.0014 |
| C3orf18 | 1.81 | 0.002 | C5orf51 | −1.2613 | 0.0231 |
| C5 | 1.487 | 0.0342 | C6orf106 | −1.1865 | 0.0439 |
| C5orf56 | 1.5192 | 0.0118 | C6orf47 | −1.2112 | 0.0028 |
| C6orf48 | 1.4943 | 0.0268 | C6orf62 | −1.2745 | 0.0253 |
| C7orf34 | 2.537 | 0.047 | C7orf26 | −1.1759 | 0.0446 |
| C7orf61 | 2.4789 | 0.0385 | C7orf33 | −2.9475 | 0.0208 |
| C8orf37 | 1.2399 | 0.0447 | C8orf44-SGK3 | −2.5165 | 0.0466 |
| CACNA2D4 | 1.8276 | 0.0365 | C8orf76 | −1.2815 | 0.0103 |
| CACNB1 | 1.5228 | 0.036 | C9orf69 | −1.2546 | 0.0426 |
| CACNG2 | 1.5067 | 0.0499 | CAAP1 | −1.3178 | 0.0269 |
| CACTIN-AS1 | 2.0458 | 0.0081 | CACUL1 | −1.3493 | 0.0025 |
| CADM3-AS1 | 1.9155 | 0.0309 | CALCOCO2 | −1.3364 | 0.0301 |
| CADPS | 2.3122 | 0.0157 | CALM1 | −1.1826 | 0.044 |
| CAMK1 | 1.5175 | 0.0075 | CAND1 | −1.3415 | 0.0419 |
| CBLB | 1.4374 | 0.0142 | CAPN1 | −1.1978 | 0.0176 |
| CBLN3 | 2.1782 | 0.0044 | CARD6 | −1.7927 | 0.0003 |
| CBS | 12.1492 | 0.0152 | CARS | −1.2136 | 0.0254 |
| CCDC116 | 3.0459 | 0.015 | CASK-AS1 | −1.8323 | 0.0333 |
| CCDC144NL-AS1 | 4.4742 | 0.0309 | CAST | −1.3378 | 0.0414 |
| CCDC146 | 1.5731 | 0.0372 | CBL | −1.3091 | 0.0107 |
| CCDC148 | 2.5039 | 0.0086 | CBWD3 | −2.0327 | 0.0128 |
| CCDC149 | 1.4155 | 0.0087 | CCAR1 | −1.2035 | 0.0338 |
| CCDC151 | 1.8169 | 0.0097 | CCDC126 | −1.4686 | 0.0175 |
| CCDC170 | 1.5748 | 0.0348 | CCDC173 | −2.715 | 0.0231 |
| CCDC175 | 1.5174 | 0.0028 | CCDC51 | −1.2573 | 0.0384 |
| CCDC180 | 2.1704 | 0.0172 | CCDC86 | −1.2707 | 0.0433 |
| CCDC24 | 1.8067 | 0.0191 | CCDC97 | −1.1585 | 0.047 |
| CCDC42 | 2.7424 | 0.0339 | CCL15 | −1.5406 | 0.0333 |
| CCDC80 | 2.2114 | 0.0295 | CCL18 | −2.8822 | 0.0326 |
| CCER2 | 2.3525 | 0.0225 | CD3EAP | −1.5883 | 0.0272 |
| CCL14 | 2.1953 | 0.0317 | CDC23 | −1.2077 | 0.023 |
| CD248 | 2.0136 | 0.0388 | CDC37L1 | −1.3379 | 0.0409 |
| CD72 | 1.9173 | 0.0156 | CDC42EP3P1 | −1.8907 | 0.0333 |
| CD99L2 | 1.3265 | 0.0017 | CDC42-IT1 | −2.3628 | 0.0369 |
| CDC20P1 | 1.8938 | 0.0086 | CDC5L | −1.2426 | 0.0365 |
| CDKN2A | 2.8483 | 0.004 | CDK13 | −1.2108 | 0.0421 |
| CDKN2B-AS1 | 2.0142 | 0.0171 | CDK17 | −1.2322 | 0.0349 |
| CDR1 | 2.3454 | 0.0436 | CDK8 | −1.3315 | 0.0046 |
| CDRT4 | 24.2411 | 0.0418 | CDS1 | −1.2816 | 0.0319 |
| CENPVP1 | 1.3967 | 0.0481 | CDV3 | −1.2913 | 0.0396 |
| CEP126 | 1.4003 | 0.0003 | CEBPB | −1.2115 | 0.0466 |
| CEP164P1 | 2.006 | 0.0193 | CEBPZ | −1.2441 | 0.0433 |
| CERCAM | 1.6534 | 0.0488 | CEMIP | −1.364 | 0.0492 |
| CERS5 | 1.3606 | 0.0225 | CEP104 | −1.3952 | 0.0113 |
| CFAP69 | 1.7236 | 0.0451 | CEP192 | −1.1973 | 0.0264 |
| CFAP70 | 1.8618 | 0.0331 | CEP350 | −1.3912 | 0.0342 |
| CFD | 2.1744 | 0.0165 | CEPT1 | −1.2412 | 0.0356 |
| CFH | 2.1932 | 0.047 | CFAP126 | −4.4147 | 0.033 |
| CGB5 | 12.1872 | 0.0277 | CH17-360D5.2 | −1.5039 | 0.017 |
| CHODL | 1.5995 | 0.0472 | CHAC2 | −1.6269 | 0.0008 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
| --- | --- | --- | --- | --- | --- |
| Gene Symbol | Fold Change | Raw P Value | Gene Symbol | Fold Change | Raw P Value |
| CILP | 4.2103 | 0.0105 | CHD4 | −1.2499 | 0.0164 |
| CLCNKA | 5.7051 | 0.0197 | CHD8 | −1.2207 | 0.0381 |
| CLCNKB | 3.7978 | 0.0265 | CHIC2 | −1.4628 | 0.0332 |
| CLDN11 | 1.8842 | 0.012 | CHM | −1.3011 | 0.0368 |
| CLEC11A | 1.4953 | 0.0175 | CHMP5 | −1.3298 | 0.006 |
| CLEC4G | 3.5255 | 0.0107 | CHMP7 | −1.2601 | 0.0011 |
| CLIC1P1 | 3.7206 | 0.0434 | CHORDC1 | −1.8685 | 0.0038 |
| CLIP3 | 1.7599 | 0.0009 | CHP1 | −1.1719 | 0.0155 |
| CLRN1-AS1 | 1.2967 | 0.0384 | CHUK | −1.4014 | 0.0075 |
| CMTM3 | 1.4575 | 0.0181 | CHURC1-FNTB | −18.7461 | 0.0109 |
| CMTM5 | 2.3109 | 0.0453 | CIAO1 | −1.2081 | 0.0255 |
| CNRIP1 | 1.6094 | 0.0497 | CIAPIN1 | −1.3136 | 0.0021 |
| CNTN3 | 2.6122 | 0.008 | CKAP4 | −1.4337 | 0.0217 |
| CNTN6 | 3.0473 | 0.0021 | CKAP5 | −1.2868 | 0.0125 |
| CNTNAP1 | 1.727 | 0.0068 | CLCA4 | −2.2597 | 0.0347 |
| COL16A1 | 1.4688 | 0.0103 | CLCN3 | −1.6854 | 0.0134 |
| COL9A2 | 2.036 | 0.0037 | CLOCK | −1.3491 | 0.028 |
| COLGALT2 | 1.4332 | 0.0217 | CLP1 | −1.1823 | 0.023 |
| COPZ2 | 1.3345 | 0.0469 | CLPTM1 | −1.2601 | 0.0394 |
| CORT | 1.7643 | 0.0296 | CLTC | −1.4333 | 0.0436 |
| COX4I2 | 1.7195 | 0.0437 | CLUH | −1.2265 | 0.0227 |
| COX7A1 | 2.6258 | 0.0055 | CLUHP6 | −1.7825 | 0.0333 |
| CPNE7 | 1.7074 | 0.0359 | CMAS | −1.2771 | 0.0091 |
| CRHR1 | 1.9553 | 0.0114 | CMB9-22P13.2 | −2.0989 | 0.0333 |
| CRIP3 | 3.8236 | 0.0325 | CNOT6 | −1.1979 | 0.0124 |
| CRYBA4 | 2.9322 | 0.0031 | CNOT7 | −1.3251 | 0.0258 |
| CRYGN | 1.9963 | 0.0455 | CNTN5 | −1.2865 | 0.0416 |
| CTA-481E9.4 | 7.0452 | 0.0004 | COA7 | −1.4455 | 0.0148 |
| CTB-31N19.3 | 1.7083 | 0.0394 | COG3 | −1.2643 | 0.0164 |
| CTB-40H15.4 | 5.4026 | 0.0092 | COG6 | −1.287 | 0.0415 |
| CTB-83J4.1 | 4.9066 | 0.0148 | COG8 | −1.5365 | 0.0063 |
| CTC-350I8.1 | 3.8601 | 0.0201 | COL4A3BP | −1.4768 | 0.0264 |
| CTC-429P9.3 | 1.5931 | 0.0179 | COMMD5 | −1.16 | 0.0092 |
| CTC-435M10.12 | 4.5442 | 0.0402 | COMT | −1.2235 | 0.031 |
| CTC-444N24.6 | 2.748 | 0.0053 | COPA | −1.2195 | 0.0389 |
| CTC-471J1.10 | 3.683 | 0.0256 | COPB2 | −1.3494 | 0.0191 |
| CTC-490E21.11 | 2.3296 | 0.0072 | COPS2 | −1.3307 | 0.0371 |
| CTC-492K19.7 | 3.5612 | 0.0398 | COX10 | −1.3665 | 0.0144 |
| CTC-498J12.1 | 3.5068 | 0.046 | COX18 | −1.3125 | 0.0061 |
| CTC-510F12.2 | 3.1029 | 0.0228 | CPN1 | −1.2933 | 0.0333 |
| CTC-524C5.2 | 1.8045 | 0.0366 | CPSF2 | −1.3673 | 0.0101 |
| CTC-529I10.2 | 2.0282 | 0.0466 | CRCP | −1.3494 | 0.000098456 |
| CTC-537E7.3 | 3.0118 | 0.0404 | CRK | −1.3184 | 0.0115 |
| CTC-550B14.6 | 3.94 | 0.0062 | CRKL | −1.3422 | 0.0198 |
| CTD-2001J20.1 | 1.4081 | 0.0338 | CRLF3 | −1.4073 | 0.0216 |
| CTD-2026K11.5 | 1.9892 | 0.0124 | CRY1 | −1.6073 | 0.0442 |
| CTD-2035E11.4 | 2.9301 | 0.0284 | CSDE1 | −1.2722 | 0.0318 |
| CTD-2201E18.3 | 2.3377 | 0.0014 | CSNK1A1 | −1.309 | 0.0342 |
| CTD-2292M16.8 | 1.4032 | 0.0303 | CSNK1G2-AS1 | −4.2601 | 0.0161 |
| CTD-2339F6.1 | 2.8597 | 0.0033 | CSNK2A1 | −1.3524 | 0.0147 |
| CTD-2380F24.1 | 4.0759 | 0.0315 | CSTF1 | −1.2358 | 0.0365 |
| CTD-2515H24.2 | 3.3604 | 0.0428 | CSTF2 | −1.3153 | 0.0335 |
| CTD-2517M22.17 | 2.0902 | 0.0281 | CTA-253N17.1 | −2.5782 | 0.0319 |
| CTD-2525I3.2 | 4.3342 | 0.0249 | CTA-929C8.5 | −2.9471 | 0.0333 |
| CTD-2527I21.14 | 7.7241 | 0.0087 | CTAGE15 | −4.281 | 0.0274 |
| CTD-2532K18.2 | 4.2983 | 0.0482 | CTB-14A14.2 | −2.7869 | 0.0049 |
| CTD-2544H17.2 | 4.6513 | 0.0137 | CTB-32O4.3 | −2.7878 | 0.0466 |
| CTD-2555O16.4 | 1.5004 | 0.0206 | CTB-35F21.3 | −1.7055 | 0.0333 |
| CTD-2595P9.4 | 4.7099 | 0.0157 | CTB-60E11.9 | −3.2708 | 0.0274 |
| CTD-2639E6.9 | 2.2381 | 0.0307 | CTC-203F4.2 | −1.4815 | 0.0265 |
| CTD-2651B20.3 | 4.5936 | 0.026 | CTC-326K19.6 | −2.9588 | 0.0333 |
| CTD-2651B20.6 | 5.4564 | 0.0007 | CTC-339F2.2 | −2.2746 | 0.0333 |
| CTD-3010D24.3 | 3.5501 | 0.03 | CTC-454I21.3 | −2.6098 | 0.0333 |
| CTD-3035K23.7 | 2.3689 | 0.0379 | CTC-487M23.5 | −1.9002 | 0.0167 |
| CTD-3076O17.2 | 2.1581 | 0.021 | CTC-497E21.3 | −1.7622 | 0.0136 |
| CTD-3193K9.3 | 4.5542 | 0.0266 | CTC-559E9.13 | −1.7038 | 0.0333 |
| CTD-3214K19.6 | 2.3124 | 0.0112 | CTD-2005H7.1 | −1.8256 | 0.0333 |
| CTD-3222D19.9 | 2.0694 | 0.032 | CTD-2012J19.3 | −1.9503 | 0.0278 |
| CTGF | 2.9577 | 0.01 | CTD-2033A16.1 | −2.7768 | 0.0333 |
| CTHRC1 | 1.5774 | 0.0327 | CTD-2215E18.3 | −2.5799 | 0.0333 |
| CTRL | 1.8872 | 0.0379 | CTD-2228K2.2 | −1.543 | 0.0333 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| CTSF | 1.3652 | 0.009 | CTD-2311M21.2 | −2.8668 | 0.0349 |
| CUBN | 1.6715 | 0.003 | CTD-2318O12.1 | −1.7707 | 0.0333 |
| CUTC | 1.2417 | 0.0497 | CTD-2325K12.1 | −1.8914 | 0.0333 |
| CXCL14 | 1.6476 | 0.0221 | CTD-2370N5.3 | −4.3268 | 0.0342 |
| CYB5R3 | 1.222 | 0.041 | CTD-2525I3.8 | −1.6177 | 0.0333 |
| DAAM2 | 1.435 | 0.0499 | CTD-2547L16.3 | −3.7034 | 0.0129 |
| DAB2 | 1.6986 | 0.0259 | CTD-2562G15.2 | −3.4721 | 0.0349 |
| DBN1 | 1.7633 | 0.0248 | CTD-2588J6.2 | −2.808 | 0.0333 |
| DCHS2 | 2.1707 | 0.0307 | CTD-2616J11.16 | −1.8226 | 0.0333 |
| DCLK2 | 1.7123 | 0.0058 | CTD-2619J13.14 | −1.5065 | 0.0399 |
| DCN | 1.8416 | 0.0271 | CTD-3126B10.5 | −5.3712 | 0.0239 |
| DDIT3 | 1.404 | 0.0328 | CTR9 | −1.476 | 0.0121 |
| DDR2 | 1.7111 | 0.0332 | CTRB2 | −1.8043 | 0.0333 |
| DDTL | 1.6267 | 0.0485 | CTTNBP2NL | −1.3445 | 0.0288 |
| DGKD | 1.5974 | 0.0323 | CUL1 | −1.2729 | 0.0142 |
| DHDH | 1.9815 | 0.0108 | CUL4A | −1.2341 | 0.0208 |
| DHRS12 | 1.5799 | 0.0018 | CXorf56 | −1.3987 | 0.0028 |
| DIO3 | 5.1807 | 0.0053 | CYB5A | −1.2849 | 0.0048 |
| DIO3OS | 3.3577 | 0.016 | CYP24A1 | −2.4315 | 0.0409 |
| DIP2C | 1.25 | 0.0357 | CYP4A22-AS1 | −3.6128 | 0.0328 |
| DISC1FP1 | 2.939 | 0.0163 | CYP51A1 | −1.9123 | 0.0035 |
| DLG4 | 1.4534 | 0.0085 | CYP7B1 | −1.5372 | 0.02 |
| DLGAP4-AS1 | 3.3381 | 0.0067 | DAAM1 | −1.3957 | 0.0442 |
| DLX2-AS1 | 3.5674 | 0.0026 | DBT | −1.4072 | 0.0452 |
| DMRT2 | 2.2096 | 0.0133 | DCAF10 | −1.3233 | 0.0165 |
| DMRTC1B | 4.0773 | 0.0112 | DCAF12 | −1.3109 | 0.0305 |
| DNAH10OS | 1.6098 | 0.0265 | DCAF7 | −1.2448 | 0.0259 |
| DNM1 | 1.6726 | 0.0379 | DCDC2C | −1.5527 | 0.0443 |
| DNM3OS | 2.0829 | 0.0033 | DCLRE1B | −1.1921 | 0.0393 |
| DOK1 | 1.3896 | 0.018 | DCTN1 | −1.1465 | 0.0478 |
| DPY19L2 | 1.6356 | 0.0359 | DCTN4 | −1.2827 | 0.0087 |
| DSCR9 | 3.3773 | 0.0221 | DCTN5 | −1.5053 | 0.0321 |
| EBF1 | 1.8577 | 0.0065 | DCUN1D1 | −1.4873 | 0.0371 |
| EBF4 | 1.6985 | 0.009 | DCUN1D3 | −1.5054 | 0.0392 |
| ECM2 | 1.8294 | 0.009 | DDB1 | −1.2078 | 0.0461 |
| EDA | 1.6199 | 0.0345 | DDI2 | −1.3975 | 0.0063 |
| EDA2R | 2.5423 | 0.0037 | DDIAS | −1.3753 | 0.0217 |
| EFEMP2 | 1.8745 | 0.0139 | DDOST | −1.2137 | 0.0184 |
| EFNA5 | 1.273 | 0.0241 | DDX23 | −1.1756 | 0.0065 |
| EGFLAM-AS4 | 3.3075 | 0.0016 | DDX27 | −1.1906 | 0.0221 |
| EID2B | 1.5671 | 0.0386 | DDX28 | −1.1789 | 0.0356 |
| ELANE | 2.5271 | 0.0132 | DDX31 | −1.275 | 0.0493 |
| ELOVL2 | 1.7925 | 0.0388 | DDX46 | −1.3136 | 0.0152 |
| EMX2OS | 1.75 | 0.0061 | DDX50P1 | −2.6308 | 0.0212 |
| ENO3 | 1.611 | 0.0221 | DDX6 | −1.1808 | 0.0262 |
| EPB41L2 | 1.3615 | 0.0311 | DEDD | −1.1945 | 0.0089 |
| EPHA3 | 1.9207 | 0.0198 | DEFB109P1 | −3.851 | 0.0367 |
| ERICH6-AS1 | 2.2554 | 0.0241 | DERL1 | −1.1891 | 0.0196 |
| ERLEC1P1 | 5.8845 | 0.0155 | DESI2 | −1.2058 | 0.0253 |
| ERMN | 2.2384 | 0.0155 | DGCR2 | −1.1791 | 0.0416 |
| ERO1B | 1.3053 | 0.0465 | DHCR24 | −1.685 | 0.011 |
| ESRG | 2.7593 | 0.0397 | DHCR7 | −1.8897 | 0.004 |
| EVX1 | 1.5081 | 0.0357 | DHRS13 | −1.293 | 0.0396 |
| EXOC3L4 | 2.0911 | 0.0226 | DHX29 | −1.3707 | 0.0298 |
| FADS3 | 1.747 | 0.0497 | DHX57 | −1.252 | 0.0052 |
| FAHD2CP | 1.9015 | 0.0291 | DHX8 | −1.2351 | 0.0297 |
| FAM101B | 1.6169 | 0.0121 | DIAPH1 | −1.3123 | 0.0458 |
| FAM103A2P | 27.3577 | 0.0346 | DIP2A-IT1 | −1.8304 | 0.0333 |
| FAM133A | 2.2374 | 0.0113 | DLAT | −1.3297 | 0.0305 |
| FAM13A | 1.408 | 0.000070643 | DNAAF2 | −1.3029 | 0.0338 |
| FAM186A | 2.5452 | 0.0463 | DNAJA1 | −1.7319 | 0.0273 |
| FAM189A2 | 2.518 | 0.047 | DNAJA2 | −1.3217 | 0.0052 |
| FAM228B | 1.8847 | 0.0102 | DNAJA3 | −1.2901 | 0.046 |
| FAM229B | 1.601 | 0.0365 | DNAJC5 | −1.2034 | 0.0427 |
| FAM66C | 1.8091 | 0.0191 | DNAJC6 | −1.4033 | 0.0168 |
| FAM90A10P | 2.0257 | 0.0027 | DNAJC7 | −1.1453 | 0.0357 |
| FAM95B1 | 3.302 | 0.0201 | DPF2 | −1.3154 | 0.004 |
| FAUP1 | 4.2851 | 0.0025 | DPH3 | −1.3236 | 0.0126 |
| FBLN1 | 1.9254 | 0.0278 | DPPA5P2 | −2.0313 | 0.0333 |
| FBXO32 | 1.4733 | 0.0496 | DRG1 | −1.2126 | 0.0141 |
| FCGR2C | 2.7604 | 0.0475 | DSC1 | −3.1723 | 0.0294 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| FCGRT | 1.4017 | 0.0195 | DSC3 | −1.3781 | 0.0267 |
| FCRL2 | 2.6291 | 0.0365 | DSCR3 | −1.2514 | 0.0015 |
| FGF12 | 2.0865 | 0.0265 | DSG1 | −2.0981 | 0.0383 |
| FGF14 | 1.6325 | 0.0187 | DSTYK | −1.2305 | 0.0475 |
| FGF16 | 4.0715 | 0.0131 | DUSP11 | −1.2867 | 0.0105 |
| FGF2 | 1.786 | 0.0089 | DUSP18 | −1.4042 | 0.0492 |
| FIBIN | 1.848 | 0.0266 | DUTP7 | −1.7666 | 0.0333 |
| FKBP7 | 1.613 | 0.0479 | DYNC1H1 | −1.272 | 0.0174 |
| FLJ13224 | 2.6759 | 0.0087 | DYNC1I2 | −1.3428 | 0.0362 |
| FLT3LG | 1.5 | 0.004 | EAF1 | −1.5018 | 0.0064 |
| FMO3 | 1.9514 | 0.0422 | EARS2 | −1.307 | 0.01 |
| FNDC4 | 1.5218 | 0.0362 | ECD | −1.2056 | 0.0228 |
| FOXB1 | 1.7681 | 0.0278 | EDC3 | −1.2213 | 0.0182 |
| FOXC2-AS1 | 3.5576 | 0.0007 | EDEM3 | −1.6068 | 0.0072 |
| FOXD2-AS1 | 1.6484 | 0.0451 | EEF1B2P7 | −3.9062 | 0.0181 |
| FOXD4L4 | 2.2392 | 0.0247 | EFCAB14 | −1.2232 | 0.0243 |
| FRS3 | 1.8147 | 0.0103 | EFTUD1 | −1.3305 | 0.0481 |
| FSIP2 | 1.5575 | 0.0455 | EFTUD2 | −1.2148 | 0.0286 |
| FSIP2-AS1 | 4.6939 | 0.015 | EHD1 | −1.3896 | 0.0022 |
| FST | 1.7148 | 0.0254 | EI24 | −1.2797 | 0.0217 |
| FTH1P19 | 3.9964 | 0.0493 | EIF1AD | −1.2074 | 0.0422 |
| FTH1P23 | 6.2543 | 0.0007 | EIF2B2 | −1.3956 | 0.0259 |
| FTL | 1.5206 | 0.0346 | EIF3A | −1.602 | 0.0333 |
| FUCA1P1 | 2.846 | 0.0009 | EIF3J | −1.3032 | 0.0119 |
| FUK | 1.2978 | 0.0216 | EIF4A2P1 | −2.5972 | 0.0213 |
| FXYD1 | 2.2303 | 0.0274 | EIF4A3 | −1.3056 | 0.0031 |
| FXYD6 | 1.6211 | 0.0235 | EIF4E | −1.5527 | 0.0319 |
| FYN | 1.396 | 0.0037 | EIF4EBP2 | −1.2382 | 0.0043 |
| FZD10-AS1 | 2.0348 | 0.0181 | EIF4ENIF1 | −1.1136 | 0.008 |
| FZD2 | 1.4635 | 0.0472 | EIF4G1 | −1.3473 | 0.0255 |
| GAA | 1.419 | 0.0457 | EIF4G2 | −1.334 | 0.017 |
| GABBR1 | 1.812 | 0.041 | EIF4H | −1.2433 | 0.018 |
| GAPDHP70 | 2.0515 | 0.045 | EIF5AP4 | −4.6717 | 0.0193 |
| GARNL3 | 1.566 | 0.0038 | ELAC2 | −1.1561 | 0.0491 |
| GAS6 | 1.2649 | 0.0337 | ELAVL1 | −1.2236 | 0.0421 |
| GBGT1 | 1.2638 | 0.0495 | ELFN1 | −1.4565 | 0.0097 |
| GCNT2 | 1.1916 | 0.0445 | EMC10 | −1.2285 | 0.0208 |
| GDF10 | 2.7762 | 0.0344 | EMC3 | −1.1598 | 0.0293 |
| GDPD5 | 1.89 | 0.026 | EMP2 | −1.3069 | 0.0343 |
| GFRA1 | 1.7296 | 0.0417 | ENAH | −1.7853 | 0.0499 |
| GFRA3 | 2.4136 | 0.0492 | ENDOD1 | −1.3175 | 0.035 |
| GGA2 | 1.0903 | 0.0392 | ENO1P3 | −2.0542 | 0.036 |
| GHR | 1.3154 | 0.0231 | ENPP7P6 | −2.1922 | 0.0333 |
| GLIPR1L2 | 3.0149 | 0.0237 | ENSA | −1.1596 | 0.0273 |
| GLIS2-AS1 | 6.903 | 0.0288 | ENTPD1-AS1 | −1.5872 | 0.0157 |
| GLRA4 | 2.3925 | 0.045 | ENTPD7 | −2.0391 | 0.0221 |
| GMDS-AS1 | 1.9531 | 0.0452 | EPHB4 | −1.2009 | 0.003 |
| GNG2 | 1.2745 | 0.0406 | EPHX3 | −1.5186 | 0.0476 |
| GOLGA8N | 1.8229 | 0.0058 | EPPK1 | −2.2098 | 0.0184 |
| GOLGA8VP | 1.9197 | 0.0015 | EPRS | −1.359 | 0.0374 |
| GORAB | 1.339 | 0.0212 | EPS15L1 | −1.2625 | 0.0364 |
| GPAA1P2 | 2.0133 | 0.0465 | EPS8L3 | −1.7936 | 0.0475 |
| GPIHBP1 | 1.8612 | 0.0316 | EPT1 | −1.3053 | 0.0034 |
| GPR162 | 2.07 | 0.0313 | ERAS | −2.816 | 0.0215 |
| GPR17 | 1.5228 | 0.0475 | ERC1 | −1.3501 | 0.038 |
| GPR173 | 2.0403 | 0.0116 | ERCC4 | −1.333 | 0.0374 |
| GPR34 | 1.4182 | 0.0138 | ERCC6 | −1.4432 | 0.0265 |
| GPRASP1 | 1.6789 | 0.0016 | ERGIC2 | −1.3127 | 0.0003 |
| GRAMD1A | 1.4649 | 0.0203 | ERICH5 | −2.0196 | 0.0348 |
| GRAPL | 1.4778 | 0.0319 | ERLIN1 | −1.5918 | 0.0141 |
| GRIA3 | 2.1965 | 0.0266 | ERRFI1 | −1.3694 | 0.0317 |
| GRID1 | 1.7435 | 0.049 | ETF1 | −1.2949 | 0.0246 |
| GRIN2C | 2.1497 | 0.0136 | EXD2 | −1.3214 | 0.0143 |
| GRM7 | 2.217 | 0.0127 | EXOC2 | −1.2583 | 0.035 |
| GS1-304P7.1 | 4.9651 | 0.0421 | EXOC5 | −1.7482 | 0.04 |
| GS1-393G12.13 | 1.8301 | 0.0391 | EXOC6 | −1.3093 | 0.0391 |
| GSTM2 | 2.1446 | 0.0048 | EXOSC3 | −1.3824 | 0.02 |
| GSTM5 | 3.2287 | 0.021 | EXTL3 | −1.3976 | 0.0014 |
| GUCA1B | 2.2616 | 0.0391 | EYA3 | −1.326 | 0.0043 |
| GUSB | 1.2419 | 0.0407 | F2RL1 | −1.333 | 0.0407 |
| GUSBP5 | 2.179 | 0.0343 | FABP7P2 | −1.895 | 0.0333 |

TABLE 10-continued

Differentially Expressed Genes in the Skin Biopsies
of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| GXYLT2 | 2.0208 | 0.0326 | FAF2 | −1.1539 | 0.0151 |
| GYPC | 1.7518 | 0.023 | FAHD1 | −1.2988 | 0.0045 |
| HAND2 | 2.4687 | 0.0124 | FAM103A1 | −1.1857 | 0.0128 |
| HAR1A | 1.3222 | 0.0343 | FAM114A2 | −1.3865 | 0.0117 |
| HAUS7 | 2.1739 | 0.0091 | FAM120B | −1.3151 | 0.0486 |
| HERC2P9 | 1.2557 | 0.0475 | FAM122A | −1.2326 | 0.0387 |
| HIGD1AP11 | 6.0692 | 0.0376 | FAM160A1 | −1.6702 | 0.0283 |
| HIGD1B | 2.0987 | 0.0366 | FAM167A-AS1 | −3.592 | 0.0189 |
| HIST1H4B | 2.4458 | 0.0237 | FAM168B | −1.2426 | 0.0365 |
| HLA-DMA | 1.4725 | 0.0357 | FAM175B | −1.1578 | 0.0044 |
| HLA-DOA | 1.5572 | 0.0251 | FAM185A | −1.3357 | 0.011 |
| HLA-DRB9 | 6.1002 | 0.0387 | FAM199X | −1.284 | 0.0452 |
| HMCN1 | 1.5219 | 0.0369 | FAM210A | −1.3318 | 0.0038 |
| HMGB1P24 | 4.063 | 0.0335 | FAM220A | −1.3116 | 0.0392 |
| HMGCLL1 | 3.4547 | 0.0331 | FAM222A | −1.8295 | 0.0388 |
| HMGN3 | 1.3433 | 0.0231 | FAM222B | −1.2695 | 0.0107 |
| HNRNPA1L2 | 1.4472 | 0.0239 | FAM45A | −1.2752 | 0.0282 |
| HNRNPA1P35 | 2.899 | 0.0278 | FAM53C | −1.2026 | 0.0261 |
| HNRNPMP1 | 2.224 | 0.0062 | FAM83B | −1.8529 | 0.0321 |
| HORMAD2 | 1.8235 | 0.0022 | FAM83C | −1.3591 | 0.0202 |
| HRCT1 | 3.5755 | 0.0354 | FAM83D | −1.252 | 0.0329 |
| HS3ST4 | 4.2131 | 0.0306 | FAM83H | −1.2846 | 0.0349 |
| HSD17B14 | 1.6294 | 0.0391 | FAM84A | −1.5502 | 0.0311 |
| HSPA12B | 1.8135 | 0.0081 | FAM91A1 | −1.3769 | 0.0446 |
| HSPA7 | 2.1795 | 0.0444 | FAM98A | −1.592 | 0.0014 |
| HTR1F | 3.1491 | 0.0116 | FARSA | −1.3013 | 0.0309 |
| HTR2C | 1.6336 | 0.016 | FASN | −1.7361 | 0.0022 |
| HTR3C | 2.0107 | 0.0055 | FASTKD2 | −1.3332 | 0.0332 |
| HTRA1 | 1.3238 | 0.0476 | FASTKD5 | −1.2888 | 0.0117 |
| ICA1L | 1.6612 | 0.000029233 | FBXL19 | −1.2971 | 0.0026 |
| IDUA | 1.6784 | 0.0149 | FBXL4 | −1.3453 | 0.0473 |
| IFFO1 | 1.7523 | 0.0228 | FBXO22 | −1.3791 | 0.009 |
| IFT22 | 1.2804 | 0.0214 | FBXO28 | −1.528 | 0.0154 |
| IGBP1P3 | 2.3643 | 0.0187 | FBXO3 | −1.347 | 0.0475 |
| IGDCC3 | 1.86 | 0.0025 | FBXO33 | −1.1999 | 0.015 |
| IGDCC4 | 1.9186 | 0.0026 | FBXO9 | −1.2553 | 0.0349 |
| IGF2 | 2.3862 | 0.0165 | FBXW11 | −1.388 | 0.0461 |
| IGFBP7-AS1 | 3.3068 | 0.0098 | FDFT1 | −1.5211 | 0.0017 |
| IGSF10 | 2.1929 | 0.0107 | FEM1A | −1.2742 | 0.0023 |
| IL11RA | 1.9873 | 0.0006 | FEM1B | −1.3507 | 0.013 |
| IL16 | 1.5033 | 0.0293 | FFAR2 | −1.415 | 0.0273 |
| IL17REL | 3.6092 | 0.0125 | FGFBP1 | −2.1917 | 0.0368 |
| IL1RAPL2 | 2.614 | 0.0374 | FGFR3P5 | −1.5125 | 0.0333 |
| INPP5D | 1.352 | 0.024 | FTP1L1 | −1.1867 | 0.0338 |
| INPPL1 | 1.3521 | 0.0415 | FKBP1C | −1.5386 | 0.0145 |
| IQCD | 1.3757 | 0.0125 | FKBP4 | −1.2386 | 0.0451 |
| ISL2 | 2.9191 | 0.0161 | FKBPL | −1.3403 | 0.0421 |
| ISPD-AS1 | 2.1706 | 0.005 | FLRT3 | −1.8039 | 0.0498 |
| ITGA1 | 1.7142 | 0.0135 | FNIP2 | −1.5129 | 0.0334 |
| ITGB2-AS1 | 2.0704 | 0.0357 | FOXJ1 | −1.4748 | 0.0247 |
| JPX | 1.4046 | 0.0429 | FOXK2 | −1.1881 | 0.0074 |
| KB-226F1.2 | 3.1268 | 0.023 | FOXO3B | −1.7362 | 0.0372 |
| KCNIP1 | 4.4041 | 0.0183 | FOXRED2 | −1.3409 | 0.0078 |
| KCNMB3 | 1.8279 | 0.0156 | FPGT | −1.382 | 0.0189 |
| KCNQ3 | 1.7335 | 0.0188 | FRMD8 | −1.3781 | 0.0382 |
| KCNQ4 | 2.1545 | 0.0031 | FTSJ3 | −1.2535 | 0.0056 |
| KCNT2 | 2.0743 | 0.0027 | FURIN | −1.3015 | 0.0375 |
| KIAA1755 | 2.0755 | 0.0145 | FYCO1 | −1.2486 | 0.0463 |
| KIF9-AS1 | 1.4283 | 0.0334 | FYTTD1 | −1.7107 | 0.0316 |
| KLF15 | 1.6616 | 0.0301 | G3BP1 | −1.5268 | 0.0451 |
| KLHL3 | 1.3568 | 0.0381 | GAB1 | −1.6809 | 0.0075 |
| KLHL40 | 1.8978 | 0.016 | GALNT1 | −1.4582 | 0.0477 |
| KRT17P5 | 2.5238 | 0.0151 | GAPVD1 | −1.3167 | 0.0476 |
| LA16c-306E5.1 | 3.8213 | 0.001 | GARS | −1.3148 | 0.0038 |
| LA16c-OS12.2 | 2.649 | 0.02 | GATAD2A | −1.1254 | 0.0316 |
| LAMA4 | 1.4476 | 0.0471 | GCC1 | −1.2789 | 0.0035 |
| LAMB2 | 1.3558 | 0.0028 | GCH1 | −1.3562 | 0.0369 |
| LAMC3 | 1.8238 | 0.0272 | GCNT4 | −1.6627 | 0.0344 |
| LAMP5 | 1.637 | 0.04 | GDAP2 | −1.5848 | 0.0109 |
| LARGE | 1.2366 | 0.0418 | GDPD1 | −1.5889 | 0.0445 |
| LARP6 | 1.7253 | 0.0243 | GEMIN4 | −1.2094 | 0.0023 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| LBHD1 | 1.4005 | 0.0295 | GFOD2 | −1.3387 | 0.0177 |
| LCA10 | 1.9368 | 0.0409 | GFPT1 | −1.3544 | 0.0115 |
| LDB2 | 1.5453 | 0.0379 | GID8 | −1.3104 | 0.0413 |
| LGALS1 | 1.7407 | 0.0042 | GIGYF2 | −1.3876 | 0.0085 |
| LHFP | 1.6724 | 0.0222 | GJB5 | −1.3777 | 0.044 |
| LHFPL1 | 3.7493 | 0.0219 | GMCL1 | −1.4053 | 0.0288 |
| LHFPL4 | 3.8291 | 0.0024 | GMPPB | −1.302 | 0.0078 |
| LIN7A | 1.4667 | 0.0258 | GNA15 | −1.4404 | 0.0279 |
| LINC00173 | 2.082 | 0.0453 | GNAI3 | −1.3492 | 0.029 |
| LINC00264 | 4.1552 | 0.0225 | GNB5 | −1.3398 | 0.0086 |
| LINC00404 | 4.4877 | 0.0061 | GNG12 | −1.2747 | 0.0245 |
| LINC00472 | 2.8776 | 0.0149 | GNL3L | −1.8111 | 0.0388 |
| LINC00506 | 2.0588 | 0.0367 | GNRHR | −2.3744 | 0.0301 |
| LINC00535 | 1.9699 | 0.0298 | GOLGA1 | −1.2543 | 0.013 |
| LINC00536 | 1.7765 | 0.0038 | GOLGA3 | −1.1659 | 0.0243 |
| LINC00565 | 3.1569 | 0.0398 | GOLGA4 | −1.4266 | 0.0414 |
| LINC00603 | 7.0339 | 0.0041 | GOLPH3 | −1.296 | 0.0433 |
| LINC00632 | 4.1819 | 0.0227 | GORASP2 | −1.2074 | 0.0408 |
| LINC00642 | 2.3582 | 0.0282 | GOSR1 | −1.3017 | 0.0455 |
| LINC00672 | 2.2396 | 0.0168 | GOSR2 | −1.3252 | 0.0406 |
| LINC00705 | 2.3159 | 0.0403 | GPR107 | −1.1946 | 0.0256 |
| LINC00854 | 4.1877 | 0.0145 | GPR157 | −1.4984 | 0.0429 |
| LINC00867 | 6.1751 | 0.0179 | GPR27 | −1.5917 | 0.017 |
| LINC00886 | 2.0349 | 0.019 | GPRIN1 | −1.5603 | 0.0238 |
| LINC00892 | 2.8848 | 0.0267 | GRB2 | −1.1666 | 0.0338 |
| LINC00893 | 1.6029 | 0.0361 | GRHL2 | −1.24 | 0.0322 |
| LINC00907 | 3.1495 | 0.022 | GRHL3 | −1.5244 | 0.0383 |
| LINC00911 | 2.9308 | 0.042 | GRK1 | −1.1453 | 0.0333 |
| LINC00926 | 1.9392 | 0.0083 | GRSF1 | −1.1928 | 0.0194 |
| LINC00968 | 2.926 | 0.0148 | GS1-251I9.3 | −1.8686 | 0.0333 |
| LINC00969 | 1.6005 | 0.0311 | GSK3A | −1.2566 | 0.0122 |
| LINC01070 | 2.0935 | 0.0198 | GTF2A1 | −1.277 | 0.0452 |
| LINC01102 | 2.1366 | 0.0306 | GTF2B | −1.2255 | 0.0082 |
| LINC01126 | 1.7335 | 0.0119 | GTF2E1 | −1.2896 | 0.0271 |
| LINC01138 | 2.0485 | 0.003 | GTF2E2 | −1.1818 | 0.0213 |
| LINC01142 | 4.1886 | 0.0107 | GTF2F1 | −1.1957 | 0.0318 |
| LINC01187 | 1.7855 | 0.0442 | GTF2H3 | −1.3502 | 0.0494 |
| LINC01268 | 3.0006 | 0.0177 | GTF3C2 | −1.1771 | 0.0234 |
| LINC01305 | 2.1561 | 0.0381 | GTF3C4 | −1.3169 | 0.0353 |
| LINC01342 | 1.9968 | 0.0172 | GTPBP10 | −1.1357 | 0.0416 |
| LINC01352 | 2.0829 | 0.0348 | GXYLT1 | −1.4608 | 0.0081 |
| LINC01376 | 2.361 | 0.0225 | H2AFY | −1.1681 | 0.0485 |
| LINC01479 | 4.033 | 0.0109 | HARBI1 | −1.4628 | 0.0091 |
| LINC01529 | 2.8257 | 0.0052 | HAUS2 | −1.2672 | 0.0273 |
| LINC01561 | 2.4548 | 0.0115 | HBS1L | −1.4408 | 0.0062 |
| LIPC | 2.441 | 0.0236 | HCAR2 | −1.6927 | 0.0018 |
| LIX1 | 2.9917 | 0.0006 | HDAC4 | −1.2203 | 0.0121 |
| LL21NC02-1C16.2 | 2.0453 | 0.0312 | HEATR5A | −1.3228 | 0.017 |
| LMCD1 | 1.6606 | 0.0336 | HERC4 | −1.2461 | 0.0272 |
| LMF1 | 1.3785 | 0.0238 | HIF1AN | −1.2174 | 0.0317 |
| LMO3 | 2.41 | 0.0316 | HINT3 | −1.3059 | 0.0241 |
| LMX1A | 2.5761 | 0.0241 | HIPK1 | −1.4252 | 0.0023 |
| LONRF2 | 1.9053 | 0.0342 | HIPK2 | −1.4131 | 0.0319 |
| LOXL3 | 1.6387 | 0.0031 | HIRA | −1.3186 | 0.0069 |
| LOXL4 | 2.0122 | 0.0107 | HIST1H2BG | −3.0791 | 0.0356 |
| LPAR1 | 1.6318 | 0.0413 | HIST1H2BJ | −2.6081 | 0.0234 |
| LRCH2 | 1.8092 | 0.0227 | HIST1H4F | −2.0058 | 0.0333 |
| LRRC17 | 1.86 | 0.0127 | HIST2H2AA3 | −30.8634 | 0.0305 |
| LRRC2 | 1.7582 | 0.0275 | HIST2H2BB | −7.8449 | 0.0152 |
| LRRC23 | 1.4148 | 0.0324 | HIST2H2BD | −1.625 | 0.022 |
| LRRC24 | 1.8058 | 0.025 | HK1 | −1.2428 | 0.031 |
| LRRC36 | 3.8596 | 0.0254 | HMBOX1 | −1.6683 | 0.0382 |
| LRRC37A3 | 1.7711 | 0.0093 | HMG20A | −1.3879 | 0.0244 |
| LST1 | 1.8507 | 0.01 | HMGB1P26 | −1.6489 | 0.0333 |
| LTBP3 | 1.3622 | 0.0462 | HMGCR | −1.9094 | 0.0044 |
| LTBP4 | 1.3677 | 0.0308 | HMGCS1 | −1.8123 | 0.0158 |
| LURAP1L-AS1 | 4.387 | 0.0174 | HMGN2P7 | −2.0873 | 0.0333 |
| LY6G5C | 1.9436 | 0.0486 | HNF4A | −2.1393 | 0.0107 |
| MAATS1 | 1.8862 | 0.0485 | HNRNPA1P43 | −1.5029 | 0.0333 |
| MAGED4 | 6.575 | 0.0041 | HNRNPH2 | −1.3732 | 0.04 |
| MAGI2-AS3 | 1.974 | 0.0188 | HOMER1 | −1.9934 | 0.0415 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| MAP2K5 | 1.1812 | 0.0356 | HOOK1 | −1.4061 | 0.0402 |
| MAPT-AS1 | 1.4271 | 0.011 | HOXA7 | −1.2401 | 0.0167 |
| MARVELD1 | 1.1948 | 0.0493 | HSBP1 | −1.2086 | 0.0431 |
| MCF2L2 | 1.455 | 0.0461 | HSD17B7 | −1.5977 | 0.0016 |
| MCIDAS | 1.6507 | 0.0485 | HSPA4 | −1.3474 | 0.0398 |
| MED12L | 1.5548 | 0.0253 | HSPA4L | −1.801 | 0.0342 |
| MEF2B | 1.7043 | 0.0337 | HSPA8 | −1.7163 | 0.0413 |
| MEGF6 | 1.4638 | 0.0092 | HSPE1-MOB4 | −1.3469 | 0.0387 |
| MEI4 | 2.0315 | 0.0267 | HUS1 | −1.4067 | 0.0022 |
| MEIKIN | 3.072 | 0.0214 | HYMAI | −1.4215 | 0.0468 |
| MEIS3 | 1.6707 | 0.0483 | ICMT | −1.2658 | 0.0352 |
| MERTK | 1.9573 | 0.0041 | IDH1 | −1.3245 | 0.0099 |
| MFAP2 | 1.6679 | 0.0249 | IDI1 | −1.4794 | 0.0175 |
| MFAP4 | 2.1259 | 0.01 | IER5 | −1.3213 | 0.011 |
| MGP | 2.8163 | 0.0043 | IFT46 | −1.2241 | 0.0124 |
| MGST3 | 1.405 | 0.043 | IGFL4 | −3.1619 | 0.0188 |
| MICAL1 | 1.501 | 0.0219 | IGHE | −4.891 | 0.0168 |
| MIR143HG | 2.1421 | 0.0441 | IGHV3-23 | −17.3034 | 0.0423 |
| MIR181A1HG | 1.5058 | 0.036 | IGHV3-29 | −1.9659 | 0.0333 |
| MND1 | 1.2607 | 0.0436 | IGHV3-74 | −12.4272 | 0.001 |
| MNX1-AS1 | 2.1296 | 0.0446 | IGHV4-39 | −14.7483 | 0.0341 |
| MPPED2 | 2.4838 | 0.0338 | IGKV1-16 | −5.2897 | 0.0434 |
| MRC2 | 1.592 | 0.0097 | IGKV1-5 | −12.7551 | 0.0213 |
| MRGPRE | 1.778 | 0.0334 | IGKV1D-12 | −7.9908 | 0.0027 |
| MRO | 2.1519 | 0.0133 | IGKV2-30 | −18.8438 | 0.0073 |
| MROH8 | 1.7422 | 0.0002 | IGKV3-20 | −16.4356 | 0.0465 |
| MRPS31P5 | 1.4293 | 0.0266 | IGLV1-44 | −12.5594 | 0.0226 |
| MSC | 1.3889 | 0.0473 | IGLV3-1 | −16.2208 | 0.0124 |
| MSH4 | 1.75 | 0.0177 | IGLV3-27 | −5.0728 | 0.026 |
| MSTN | 1.8316 | 0.0466 | IGSF3 | −1.2982 | 0.0199 |
| MSX1 | 1.7306 | 0.0149 | INA | −2.1612 | 0.0002 |
| MTMR9LP | 1.9608 | 0.0253 | INIP | −1.2911 | 0.0296 |
| MTUS1 | 1.1678 | 0.0372 | INTS5 | −1.4283 | 0.0003 |
| MTUS2-AS1 | 2.3229 | 0.0348 | INTS6 | −1.4736 | 0.0409 |
| MXRA8 | 1.7521 | 0.0222 | INTS7 | −1.4744 | 0.0147 |
| MYH6 | 1.5766 | 0.0006 | IP6K1 | −1.2936 | 0.0011 |
| MYH7B | 1.9338 | 0.0445 | IPO13 | −1.2446 | 0.0331 |
| MYL3 | 3.5164 | 0.0022 | IPP | −1.3988 | 0.0195 |
| MYO15B | 1.8791 | 0.0363 | IQCA1L | −1.3869 | 0.0333 |
| MYOC | 3.0755 | 0.0338 | IRAK1 | −1.2796 | 0.0084 |
| NAALAD2 | 2.0764 | 0.0034 | IRF6 | −1.2609 | 0.0236 |
| NALT1 | 5.9779 | 0.001 | ISG20L2 | −1.479 | 0.0127 |
| NAMPTP1 | 9.9847 | 0.0442 | ISM2 | −1.8834 | 0.0353 |
| NAP1L3 | 1.9073 | 0.0172 | ISY1 | −1.1623 | 0.0417 |
| NBPF12 | 1.2567 | 0.0414 | ITM2B | −1.3034 | 0.0218 |
| NBPF9 | 1.2615 | 0.0331 | ITPRIPL2 | −1.5336 | 0.0447 |
| NCR3 | 2.0521 | 0.0219 | IWS1 | −1.2076 | 0.0443 |
| NDUFV2-AS1 | 1.3755 | 0.045 | JPH1 | −2.2834 | 0.0472 |
| NEGR1 | 2.1011 | 0.0228 | JUP | −1.3731 | 0.0452 |
| NEK3 | 1.6466 | 0.0275 | KALRN | −1.7478 | 0.003 |
| NETO1 | 2.596 | 0.0147 | KAT6A | −1.3671 | 0.0333 |
| NHS | 1.5194 | 0.0132 | KAT7 | −1.25 | 0.0487 |
| NLRP2P | 1.5577 | 0.0361 | KB-1440D3.13 | −5.7691 | 0.0083 |
| NMNAT2 | 1.8024 | 0.0376 | KCNA7 | −1.7449 | 0.0357 |
| NMUR1 | 3.585 | 0.0447 | KCNH7 | −1.3402 | 0.0312 |
| NOG | 3.2906 | 0.0345 | KCNV2 | −1.8858 | 0.042 |
| NOL4L | 1.3356 | 0.0463 | KCTD20 | −1.2749 | 0.0071 |
| NOVA1 | 2.6879 | 0.0163 | KCTD5 | −1.3396 | 0.0039 |
| NOX4 | 2.1461 | 0.0275 | KDM5A | −1.2918 | 0.0235 |
| NPHP3 | 1.4658 | 0.0219 | KHSRP | −1.3224 | 0.0373 |
| NR2E3 | 2.8294 | 0.0013 | KIAA0368 | −1.1517 | 0.0152 |
| NR2F1-AS1 | 2.5866 | 0.0279 | KIAA1033 | −1.2864 | 0.0403 |
| NREP | 1.3113 | 0.03 | KIAA1161 | −1.4971 | 0.0029 |
| NRG4 | 1.6249 | 0.0472 | KIAA1429 | −1.2553 | 0.0168 |
| NRN1 | 1.8189 | 0.0182 | KIAA1468 | −1.2726 | 0.0408 |
| NT5C1A | 2.8834 | 0.0011 | KIAA1919 | −1.5677 | 0.0113 |
| NUDT11 | 2.0299 | 0.0396 | KIF16B | −1.3631 | 0.0158 |
| NUDT14 | 1.4349 | 0.034 | KIF1B | −1.4395 | 0.0182 |
| NYAP2 | 2.2264 | 0.0125 | KIF1BP | −1.3877 | 0.0101 |
| OCM | 4.9637 | 0.027 | KIF24 | −1.3003 | 0.019 |
| OLFML1 | 1.783 | 0.0426 | KIF3A | −1.5508 | 0.0164 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| OLFML3 | 2.004 | 0.0216 | KIF5B | −1.4248 | 0.0376 |
| OPRD1 | 1.3238 | 0.0127 | KLC1 | −1.1379 | 0.0188 |
| OR13J1 | 2.4129 | 0.0309 | KLHDC10 | −1.1498 | 0.0341 |
| OR2A1 | 3.006 | 0.0361 | KLHL18 | −1.3887 | 0.0376 |
| OR2L1P | 3.2151 | 0.016 | KLHL7 | −1.3471 | 0.0227 |
| OR2T8 | 3.6969 | 0.0222 | KLHL8 | −1.4124 | 0.026 |
| OR5P3 | 3.1126 | 0.0341 | KLK15 | −3.1514 | 0.0036 |
| OR7E105P | 2.4632 | 0.0221 | KNG1 | −1.5234 | 0.0333 |
| OR7E125P | 4.5679 | 0.0276 | KPNA1 | −1.2876 | 0.0043 |
| OSCAR | 1.5713 | 0.0329 | KPNA2 | −1.3141 | 0.0438 |
| OSR1 | 2.3893 | 0.0299 | KPNA3 | −1.3803 | 0.0205 |
| OSR2 | 2.8827 | 0.0111 | KPNA4 | −1.1889 | 0.0435 |
| OXCT1-AS1 | 2.3087 | 0.046 | KPNA6 | −1.2704 | 0.0024 |
| P3H1 | 1.2204 | 0.0258 | KPNB1 | −1.4161 | 0.0466 |
| PACS2 | 1.1957 | 0.0161 | KRR1 | −1.2721 | 0.0225 |
| PAK3 | 2.3924 | 0.0162 | KRT12 | −3.6151 | 0.0049 |
| PALM | 1.6891 | 0.0427 | KRTAP20-2 | −5.0263 | 0.0449 |
| PAPPA2 | 2.0105 | 0.0149 | LA16c-407A10.3 | −2.8075 | 0.0479 |
| PARD3B | 1.3618 | 0.0484 | LARP1 | −1.2217 | 0.0349 |
| PARP15 | 2.0829 | 0.0214 | LARP4 | −1.4231 | 0.0352 |
| PARP3 | 1.3935 | 0.0133 | LARP4B | −1.1434 | 0.0166 |
| PATL2 | 1.6214 | 0.0406 | LDAH | −1.3569 | 0.0305 |
| PAX9 | 1.705 | 0.0494 | LDHAL6A | −2.5459 | 0.025 |
| PBX4 | 1.5825 | 0.0418 | LDLR | −2.1878 | 0.0401 |
| PCAT29 | 5.9026 | 0.0006 | LDOC1L | −1.2945 | 0.0263 |
| PCBD1 | 1.2929 | 0.0255 | LEMD3 | −1.2946 | 0.0311 |
| PCDHA9 | 1.2007 | 0.0463 | LEO1 | −1.3447 | 0.0105 |
| PCDHGA1 | 1.8043 | 0.0382 | LETM1 | −1.2958 | 0.0022 |
| PCDHGA4 | 2.8158 | 0.0214 | LHFPL3 | −3.0875 | 0.0264 |
| PCED1B | 1.7285 | 0.0379 | LIG4 | −1.4245 | 0.0085 |
| PCED1B-AS1 | 2.1034 | 0.028 | LIMS3 | −4.656 | 0.0436 |
| PCOLCE | 2.0308 | 0.0328 | LINC00112 | −2.6264 | 0.0333 |
| PCOLCE-AS1 | 3.2819 | 0.0044 | LINC00483 | −1.6116 | 0.0333 |
| PCP2 | 2.675 | 0.0277 | LINC00485 | −1.2936 | 0.0333 |
| PCSK4 | 1.7503 | 0.044 | LINC00567 | −1.8642 | 0.0296 |
| PCSK5 | 2.4502 | 0.0076 | LINC00649 | −1.9467 | 0.002 |
| PDE1A | 2.3767 | 0.0096 | LINC01055 | −2.2824 | 0.0393 |
| PDE2A | 1.5302 | 0.0445 | LINC01105 | −1.7137 | 0.0344 |
| PDE4C | 3.2264 | 0.03 | LINC01123 | −1.8483 | 0.0324 |
| PDE6C | 2.7437 | 0.0002 | LINC01128 | −1.2241 | 0.0473 |
| PHC1 | 1.5668 | 0.0081 | LINC01247 | −1.3658 | 0.0333 |
| PHC1P1 | 1.5933 | 0.0404 | LINC01290 | −3.6896 | 0.0399 |
| PHKG1 | 1.9193 | 0.0057 | LINC01298 | −1.7351 | 0.0333 |
| PHLDB1 | 1.728 | 0.0234 | LINC01513 | −1.7696 | 0.0333 |
| PHYKPL | 1.331 | 0.0474 | LINC01620 | −1.7406 | 0.0333 |
| PI4KAP1 | 1.9946 | 0.0202 | LLGL1 | −1.2355 | 0.0314 |
| PIGZ | 1.4018 | 0.0447 | LLPH | −1.2109 | 0.0428 |
| PIWIL2 | 2.4473 | 0.0014 | LMBR1 | −1.2946 | 0.024 |
| PKN1 | 1.5104 | 0.04 | LONP2 | −1.4136 | 0.0318 |
| PKN3 | 1.2968 | 0.0307 | LRFN3 | −1.2416 | 0.0058 |
| PLA2G10 | 3.6444 | 0.006 | LRRC41 | −1.2757 | 0.0026 |
| PLA2G2C | 1.7676 | 0.016 | LRRC47 | −1.1445 | 0.0217 |
| PLA2G4C | 1.9223 | 0.0132 | LRRC8A | −1.3531 | 0.038 |
| PLA2G6 | 1.5277 | 0.0418 | LRWD1 | −1.3003 | 0.0234 |
| PLAC9 | 1.7989 | 0.0447 | LSM12P1 | −4.5627 | 0.0382 |
| PLCXD3 | 1.6515 | 0.0454 | LSM14A | −1.1771 | 0.0479 |
| PLD6 | 2.0497 | 0.0183 | LYPLA1 | −1.4312 | 0.0223 |
| PLEKHA6 | 1.7433 | 0.0438 | LYPLA2P2 | −2.9135 | 0.0442 |
| PLEKHS1 | 2.6515 | 0.0484 | LYRM1 | −1.2648 | 0.0153 |
| PLPP7 | 1.7469 | 0.036 | LYST | −1.3604 | 0.021 |
| PLXND1 | 1.8283 | 0.0401 | MAB21L3 | −1.7989 | 0.019 |
| PMCH | 5.045 | 0.0227 | MAEA | −1.1381 | 0.0104 |
| PMS2CL | 1.3608 | 0.0207 | MAL2 | −1.3903 | 0.0474 |
| PNMA2 | 1.944 | 0.0095 | MAML1 | −1.2938 | 0.02 |
| PNMT | 2.8685 | 0.0142 | MAN1A2 | −1.2969 | 0.0442 |
| PODN | 2.2864 | 0.0367 | MAP2K3 | −1.262 | 0.0415 |
| POFUT2 | 1.441 | 0.0289 | MAP2K4 | −1.2595 | 0.035 |
| POLR3GL | 1.303 | 0.0225 | MAP7 | −1.4061 | 0.0387 |
| POU4F3 | 2.5161 | 0.0252 | MAPK1 | −1.4729 | 0.0376 |
| POU6F1 | 1.56 | 0.0182 | MAPK14 | −1.2401 | 0.0323 |
| PPFIA2 | 1.8417 | 0.0371 | MAPKAPK5 | −1.1596 | 0.0349 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| PPIAP6 | 3.3564 | 0.0006 | MARCH7 | −1.5663 | 0.0345 |
| PPM1E | 1.9536 | 0.0459 | MARK2 | −1.4041 | 0.0143 |
| PPM1M | 1.4092 | 0.0093 | MARVELD2 | −1.477 | 0.0048 |
| PPP1R26-AS1 | 1.72 | 0.0453 | MATK | −1.5103 | 0.0303 |
| PPP1R2P9 | 2.5843 | 0.0493 | MAX | −1.1707 | 0.013 |
| PPP1R36 | 1.5237 | 0.0361 | MB21D2 | −1.2529 | 0.0322 |
| PPP1R3G | 1.8399 | 0.0043 | MBD1 | −1.2056 | 0.0232 |
| PPP1R9A | 2.3909 | 0.0441 | MCFD2 | −1.5067 | 0.0066 |
| PPP4R1L | 1.2793 | 0.0335 | MCPH1-AS1 | −3.4393 | 0.0155 |
| PRB4 | 3.185 | 0.008 | MCTS2P | −1.5382 | 0.0372 |
| PRCD | 4.9563 | 0.0056 | MDH2 | −1.192 | 0.0379 |
| PRDM6 | 1.6709 | 0.0184 | MDN1 | −1.2488 | 0.0355 |
| PRDM8 | 2.0437 | 0.0062 | MED1 | −1.1837 | 0.0109 |
| PRICKLE2-AS3 | 1.678 | 0.001 | MED14 | −1.2356 | 0.0041 |
| PRKAA2 | 1.7043 | 0.0435 | MED20 | −1.3108 | 0.0233 |
| PRKAG2-AS1 | 1.8505 | 0.0329 | MED28 | −1.1923 | 0.0322 |
| PRKD1 | 1.5803 | 0.0258 | MED29 | −1.2014 | 0.005 |
| PRKG1 | 1.7695 | 0.0403 | MED4-AS1 | −5.3576 | 0.0121 |
| PRKG2 | 1.6925 | 0.0158 | MEP1A | −1.8063 | 0.0427 |
| PRMT8 | 3.0663 | 0.0271 | MESDC2 | −1.2355 | 0.0283 |
| PRORSD1P | 2.334 | 0.038 | METAP2 | −1.2935 | 0.0296 |
| PRR23D1 | 1.7809 | 0.0239 | METTL2A | −1.3615 | 0.0105 |
| PRR29 | 2.0535 | 0.034 | METTL2B | −1.2918 | 0.0462 |
| PRR3 | 1.2982 | 0.0464 | MFAP1 | −1.4104 | 0.0265 |
| PRRX1 | 1.902 | 0.0166 | MFAP3 | −2.0251 | 0.0156 |
| PRTFDC1 | 1.5523 | 0.0267 | MFN1 | −1.4646 | 0.0345 |
| PSG5 | 4.8634 | 0.0121 | MFSD11 | −1.1599 | 0.0412 |
| PSG8 | 2.2574 | 0.0185 | MFSD6 | −1.3918 | 0.026 |
| PSMA3-AS1 | 1.3803 | 0.0269 | MFSD9 | −1.2866 | 0.0225 |
| PSMD6-AS2 | 2.2487 | 0.0399 | MGC2752 | −1.3249 | 0.0386 |
| PTH1R | 2.5474 | 0.008 | MID1IP1 | −1.4538 | 0.0234 |
| PVT1 | 1.5452 | 0.0268 | MID2 | −1.7223 | 0.0396 |
| PXDC1 | 1.3408 | 0.0116 | MIEF1 | −1.3035 | 0.01 |
| RAB40A | 2.7132 | 0.0304 | MINA | −1.2152 | 0.0328 |
| RAB9B | 1.5876 | 0.0431 | MIOS | −1.2336 | 0.0021 |
| RABL2B | 1.1438 | 0.0453 | MIOXP1 | −1.5343 | 0.0333 |
| RAPGEF4-AS1 | 1.6346 | 0.0354 | MIRLET7DHG | −5.079 | 0.0322 |
| RARRES2 | 2.2701 | 0.0101 | MKLN1 | −1.3019 | 0.0496 |
| RARRES3 | 1.8298 | 0.0057 | MKRN2 | −1.2203 | 0.0023 |
| RASA3 | 1.5284 | 0.0217 | MLEC | −1.2567 | 0.0292 |
| RASSF4 | 1.9002 | 0.029 | MLX | −1.1907 | 0.0197 |
| RBM43P1 | 2.6454 | 0.03 | MMACHC | −1.562 | 0.0189 |
| RBMS2 | 1.2859 | 0.0121 | MMADHC | −1.2079 | 0.0402 |
| RCBTB2 | 1.2337 | 0.0376 | MMGT1 | −1.1887 | 0.0419 |
| RCBTB2P1 | 3.9136 | 0.0282 | MOB4 | −1.2622 | 0.0245 |
| RCN3 | 1.8461 | 0.0255 | MOCOS | −1.7064 | 0.0002 |
| RCOR3 | 1.2842 | 0.0181 | MOCS3 | −1.271 | 0.0294 |
| REC8 | 2.1442 | 0.0265 | MORF4L2P1 | −1.5243 | 0.0333 |
| RET | 1.7975 | 0.0098 | MOSPD2 | −1.4931 | 0.0267 |
| RFESD | 1.5841 | 0.0181 | MPHOSPH8 | −1.2172 | 0.0242 |
| RFX8 | 3.7286 | 0.0226 | MPV17L2 | −1.327 | 0.0301 |
| RGN | 1.828 | 0.0142 | MPZL2 | −1.3499 | 0.0371 |
| RGPD6 | 1.8605 | 0.0488 | MRGPRX2 | −2.0812 | 0.0307 |
| RGR | 2.3659 | 0.0396 | MRPL42 | −1.2734 | 0.0207 |
| RGS22 | 3.0831 | 0.0199 | MRPL49 | −1.255 | 0.0389 |
| RGS5 | 1.5279 | 0.02 | MRS2 | −1.2065 | 0.0148 |
| RGS9 | 1.7807 | 0.028 | MSMO1 | −1.925 | 0.0238 |
| RN7SKP249 | 4.0511 | 0.0198 | MSX2 | −1.5374 | 0.0421 |
| RN7SL225P | 4.2303 | 0.0479 | MTF1 | −1.5606 | 0.0075 |
| RN7SL521P | 10.3415 | 0.0059 | MTFR1 | −1.43 | 0.0138 |
| RN7SL812P | 3.6439 | 0.0394 | MTMR12 | −1.2958 | 0.0385 |
| RNASE4 | 1.7846 | 0.027 | MTND5P12 | −1.3569 | 0.0333 |
| RNF175 | 2.8376 | 0.0087 | MTO1 | −1.4286 | 0.0149 |
| RNF207 | 2.2573 | 0.0031 | MUT | −1.3957 | 0.0107 |
| RP11-1007O24.2 | 2.9676 | 0.0023 | MVK | −1.5101 | 0.0305 |
| RP11-102G14.1 | 5.9258 | 0.0215 | MYC | −1.3578 | 0.0258 |
| RP11-106M3.2 | 2.2807 | 0.0037 | MYCBP | −1.2022 | 0.0417 |
| RP11-1070N10.3 | 3.6816 | 0.0274 | MYO5A | −1.3556 | 0.0321 |
| RP11-108L7.4 | 5.229 | 0.0406 | NAA30 | −1.5494 | 0.013 |
| RP11-1090M7.3 | 3.662 | 0.0168 | NAA50 | −1.4077 | 0.0436 |
| RP11-109D9.4 | 3.396 | 0.0443 | NACC1 | −1.3467 | 0.0072 |

TABLE 10-continued

Differentially Expressed Genes in the Skin Biopsies
of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| RP11-109P11.1 | 2.0244 | 0.0274 | NAF1 | −1.3344 | 0.0444 |
| RP11-10N23.4 | 4.995 | 0.003 | NANOS1 | −1.8884 | 0.0279 |
| RP11-1143G9.4 | 5.5551 | 0.0301 | NARS | −1.2452 | 0.0412 |
| RP11-114F3.5 | 5.2904 | 0.0214 | NBPF2P | −4.473 | 0.02 |
| RP11-118A3.1 | 2.2698 | 0.0358 | NCDN | −1.2831 | 0.0254 |
| RP11-121C6.5 | 3.8562 | 0.0191 | NCKAP1 | −1.3929 | 0.0427 |
| RP11-121L10.2 | 3.5417 | 0.0008 | NCOA4 | −1.3293 | 0.0431 |
| RP11-1228E12.1 | 2.7625 | 0.0308 | NCOA5 | −1.1438 | 0.042 |
| RP11-1277A3.1 | 1.546 | 0.0114 | NCOA6 | −1.1801 | 0.0287 |
| RP11-12D24.10 | 8.8692 | 0.0085 | NCOR1 | −1.3347 | 0.0228 |
| RP11-131L12.4 | 2.6377 | 0.0136 | NDST1 | −1.4332 | 0.0224 |
| RP11-134G8.6 | 8.4557 | 0.0404 | NDST2 | −1.2049 | 0.0482 |
| RP11-135A1.2 | 13.035 | 0.0018 | NEBL | −1.4837 | 0.0253 |
| RP11-1396O13.1 | 4.68 | 0.0028 | NEK4 | −1.6028 | 0.0265 |
| RP11-13A1.1 | 2.1903 | 0.0124 | NEO1 | −1.2284 | 0.0186 |
| RP11-141O19.1 | 1.3967 | 0.0481 | NFE2L2 | −1.323 | 0.0369 |
| RP11-142A23.1 | 2.9492 | 0.016 | NFIC | −1.3444 | 0.0441 |
| RP11-147L13.8 | 2.6435 | 0.0083 | NFKB1 | −1.3146 | 0.0258 |
| RP11-150C16.1 | 5.6801 | 0.0251 | NFKBIB | −1.2383 | 0.0257 |
| RP11-151A6.6 | 2.2015 | 0.0387 | NFRKB | −1.1548 | 0.0349 |
| RP11-151F5.2 | 4.5606 | 0.0163 | NFYA | −1.4074 | 0.0179 |
| RP11-160O5.1 | 1.9711 | 0.0257 | NGLY1 | −1.2205 | 0.0003 |
| RP11-161I6.2 | 8.8192 | 0.0153 | NHLRC1 | −1.4323 | 0.0148 |
| RP11-166B2.1 | 3.8118 | 0.0236 | NIPA1 | −1.3097 | 0.0417 |
| RP11-166B2.7 | 2.5119 | 0.0236 | NIPA2 | −1.4411 | 0.0124 |
| RP11-166D19.1 | 1.7468 | 0.0209 | NIPA2P4 | −1.3786 | 0.0333 |
| RP11-167N4.4 | 2.2331 | 0.0376 | NIPAL4 | −1.3709 | 0.0267 |
| RP11-16E12.1 | 3.7652 | 0.0015 | NKIRAS2 | −1.2858 | 0.0416 |
| RP11-16K12.2 | 3.2309 | 0.003 | NMD3 | −1.2812 | 0.0372 |
| RP11-170M17.2 | 2.5348 | 0.0383 | NMNAT1 | −1.3723 | 0.0466 |
| RP11-172E9.2 | 3.6308 | 0.0427 | NMT1 | −1.2205 | 0.0129 |
| RP11-177G23.1 | 2.5345 | 0.0388 | NOB1 | −1.1829 | 0.0257 |
| RP11-177H13.2 | 1.7126 | 0.007 | NOCT | −1.8492 | 0.0289 |
| RP11-179B15.6 | 3.4889 | 0.0263 | NOL6 | −1.3178 | 0.0323 |
| RP11-182J1.5 | 2.8075 | 0.019 | NOP14 | −1.2344 | 0.0402 |
| RP11-182J23.1 | 5.4943 | 0.0152 | NOTCH3 | −1.224 | 0.0323 |
| RP11-184E9.2 | 2.2674 | 0.0081 | NOX5 | −1.7765 | 0.0006 |
| RP11-188P20.3 | 2.5364 | 0.0255 | NPC1 | −1.3384 | 0.0181 |
| RP11-196G11.2 | 3.2395 | 0.0328 | NPM1P37 | −5.0904 | 0.0112 |
| RP11-1E1.2 | 2.6571 | 0.0198 | NR2F6 | −1.3572 | 0.0487 |
| RP11-203E8.1 | 3.0056 | 0.0493 | NRBP1 | −1.2017 | 0.0238 |
| RP11-203L2.3 | 3.2044 | 0.0104 | NSD1 | −1.3628 | 0.0044 |
| RP11-20G13.2 | 8.9548 | 0.0021 | NSDHL | −1.321 | 0.0149 |
| RP11-211G23.2 | 7.2343 | 0.0267 | NSG1 | −1.4858 | 0.0122 |
| RP11-212I21.2 | 11.4598 | 0.0109 | NSUN4 | −1.362 | 0.0011 |
| RP11-214K3.21 | 3.9434 | 0.0241 | NUDCD2 | −1.2384 | 0.0246 |
| RP11-219D15.3 | 9.2423 | 0.0122 | NUDT4 | −1.2528 | 0.0082 |
| RP11-21A7A.4 | 2.2073 | 0.0183 | NUDT5 | −1.2025 | 0.024 |
| RP11-222K16.1 | 4.4139 | 0.045 | NUP133 | −1.1416 | 0.0331 |
| RP11-227B21.2 | 6.0365 | 0.0116 | NUP160 | −1.3408 | 0.0481 |
| RP11-227G15.11 | 2.4742 | 0.0304 | NUP188 | −1.2711 | 0.042 |
| RP11-228B15.4 | 1.8585 | 0.0134 | NUP35 | −1.2791 | 0.0388 |
| RP11-234G16.5 | 4.5816 | 0.0425 | NUP54 | −1.2739 | 0.0267 |
| RP11-236L14.2 | 2.5863 | 0.0312 | NUP98 | −1.3501 | 0.0234 |
| RP11-23D24.2 | 3.0944 | 0.0068 | ODC1 | −2.0194 | 0.0363 |
| RP11-23J18.1 | 2.9876 | 0.036 | OGDH | −1.3968 | 0.0366 |
| RP11-23J9.5 | 1.6394 | 0.0374 | OGFOD1 | −1.5397 | 0.0131 |
| RP11-23N2.4 | 2.2055 | 0.0407 | OPA3 | −1.3046 | 0.0002 |
| RP11-244H3.1 | 1.9372 | 0.0056 | OR2A7 | −2.968 | 0.0152 |
| RP11-244M2.1 | 1.6348 | 0.0471 | OR51K1P | −1.997 | 0.0333 |
| RP11-247A12.2 | 3.0964 | 0.0035 | OR7E128P | −2.7176 | 0.0332 |
| RP11-247L20.3 | 3.4732 | 0.0054 | OR7E130P | −2.5333 | 0.0275 |
| RP11-248J18.2 | 1.6324 | 0.0404 | OR7M1P | −6.7037 | 0.014 |
| RP11-24M17.4 | 4.8621 | 0.0105 | OR9N1P | −2.169 | 0.0333 |
| RP11-250B2.3 | 3.891 | 0.027 | OSBP | −1.3624 | 0.0017 |
| RP11-254F7.3 | 50.8165 | 0.0251 | OSBPL10 | −1.4806 | 0.0357 |
| RP11-256I9.2 | 2.7747 | 0.0413 | OSBPL11 | −1.445 | 0.0045 |
| RP11-260E18.1 | 3.5535 | 0.0057 | OSTM1 | −1.2835 | 0.0298 |
| RP11-266J6.2 | 8.6006 | 0.0208 | OTP | −1.4636 | 0.0291 |
| RP11-269C23.5 | 7.3579 | 0.0077 | OTUD4 | −1.3729 | 0.0168 |
| RP11-26J3.3 | 1.4377 | 0.0338 | OTULIN | −1.4622 | 0.0025 |

TABLE 10-continued

Differentially Expressed Genes in the Skin Biopsies
of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| RP11-280O24.3 | 2.3369 | 0.0234 | OXCT1 | −1.3812 | 0.0358 |
| RP11-282A11.4 | 3.7257 | 0.0058 | OXNAD1 | −1.3219 | 0.0183 |
| RP11-284F21.9 | 2.163 | 0.0278 | P2RX3 | −2.0851 | 0.0269 |
| RP11-290O12.2 | 4.9576 | 0.0158 | P3H2-AS1 | −4.6129 | 0.0344 |
| RP11-296A18.5 | 3.2267 | 0.037 | PABPC3 | −1.5214 | 0.0481 |
| RP11-297N6.4 | 2.3468 | 0.0083 | PANK3 | −1.4098 | 0.0409 |
| RP11-298P3.4 | 1.7737 | 0.0157 | PANK4 | −1.1338 | 0.0332 |
| RP11-2C24.7 | 4.4653 | 0.0399 | PAPSS1 | −1.2866 | 0.0485 |
| RP11-305L7.1 | 3.2578 | 0.0437 | PAQR3 | −1.2626 | 0.0152 |
| RP11-305O6.3 | 1.7208 | 0.036 | PARG | −1.6841 | 0.0003 |
| RP11-307B6.3 | 4.2763 | 0.0373 | PCDHGA10 | −1.5594 | 0.0474 |
| RP11-307L14.1 | 5.1266 | 0.0082 | PCDHGA11 | −1.7936 | 0.0189 |
| RP11-325I22.3 | 2.6399 | 0.0048 | PCDHGA8 | −1.9109 | 0.0352 |
| RP11-325K4.2 | 1.447 | 0.0299 | PCP4L1 | −2.0589 | 0.0364 |
| RP11-326C3.7 | 2.2362 | 0.0379 | PCSK9 | −1.629 | 0.0137 |
| RP11-327F22.2 | 2.2494 | 0.0261 | PCYOX1 | −1.3137 | 0.0382 |
| RP11-329B9.4 | 4.5014 | 0.0313 | PCYT1A | −1.294 | 0.0193 |
| RP11-329B9.5 | 6.2307 | 0.0227 | PDCD2 | −1.2026 | 0.0224 |
| RP11-331F9.3 | 3.5972 | 0.003 | PDCD6IP | −1.3038 | 0.0231 |
| RP11-333J10.2 | 5.1259 | 0.0274 | PDCD7 | −1.1955 | 0.0283 |
| RP11-334A14.8 | 2.9908 | 0.027 | PDE12 | −1.7231 | 0.0251 |
| RP11-335L23.4 | 3.2632 | 0.0455 | PDIA6 | −1.4118 | 0.0327 |
| RP11-335L23.5 | 3.6596 | 0.0387 | PDP2 | −1.461 | 0.0418 |
| RP11-343B18.2 | 2.6303 | 0.0376 | PDPK1 | −1.3083 | 0.0198 |
| RP11-344H11.5 | 3.1529 | 0.0007 | PDXDC1 | −1.2584 | 0.047 |
| RP11-345J18.2 | 2.1109 | 0.0213 | PEX13 | −1.2448 | 0.0407 |
| RP11-345K9.2 | 2.5758 | 0.0412 | PEX3 | −1.3771 | 0.0067 |
| RP11-346C20.4 | 5.5016 | 0.0089 | PGA3 | −6.2115 | 0.0285 |
| RP11-347C12.11 | 1.9312 | 0.0214 | PGAM5 | −1.2876 | 0.0343 |
| RP11-347C18.5 | 12.0029 | 0.0022 | PGS1 | −1.2063 | 0.0446 |
| RP11-351C21.2 | 6.4328 | 0.016 | PHAX | −1.2416 | 0.028 |
| RP11-352D13.5 | 5.1242 | 0.0009 | PHBP2 | −2.4352 | 0.0444 |
| RP11-352D13.6 | 3.8368 | 0.0084 | PHF14 | −1.2662 | 0.0069 |
| RP11-354E11.2 | 4.0613 | 0.0109 | PHF20 | −1.1937 | 0.0082 |
| RP11-357N13.6 | 1.6792 | 0.0308 | PHF20L1 | −1.2667 | 0.0186 |
| RP11-358B23.1 | 5.785 | 0.0018 | PHF24 | −1.8043 | 0.0253 |
| RP11-358L22.3 | 1.9682 | 0.0477 | PHTF1 | −1.2485 | 0.0467 |
| RP11-360F5.3 | 2.4175 | 0.0417 | PI4K2A | −1.3458 | 0.0453 |
| RP11-360L9.7 | 15.5669 | 0.0092 | PIAS1 | −1.3386 | 0.0261 |
| RP11-362F19.3 | 4.3302 | 0.0144 | PIAS4 | −1.26 | 0.0132 |
| RP11-368L12.1 | 3.8349 | 0.0343 | PIK3R4 | −1.3722 | 0.0401 |
| RP11-379F4.6 | 7.166 | 0.0187 | PIP4K2C | −1.1781 | 0.02 |
| RP11-379F4.8 | 4.844 | 0.047 | PITPNA | −1.2747 | 0.0263 |
| RP1-137D17.2 | 4.3986 | 0.0195 | PLA2G12A | −1.3436 | 0.0082 |
| RP11-382A20.1 | 5.6464 | 0.0178 | PLAA | −1.3858 | 0.0185 |
| RP11-384F7.2 | 3.0229 | 0.0484 | PLD1 | −1.5197 | 0.0018 |
| RP11-388C12.8 | 2.4936 | 0.0063 | PLEKHA7 | −1.2778 | 0.0448 |
| RP11-38H17.1 | 11.6119 | 0.0114 | PLEKHA8 | −1.2602 | 0.0234 |
| RP11-38M8.1 | 3.3431 | 0.0067 | PLEKHB2 | −1.2942 | 0.0058 |
| RP11-393I2.4 | 1.7697 | 0.0328 | PLS1 | −1.7431 | 0.0147 |
| RP11-396B14.2 | 5.3781 | 0.0028 | PMS2 | −1.3029 | 0.0123 |
| RP11-397A16.1 | 6.6929 | 0.0008 | PNLDC1 | −3.078 | 0.0307 |
| RP11-397P13.6 | 3.5818 | 0.0005 | PNO1 | −1.3544 | 0.0441 |
| RP11-399K21.14 | 2.3587 | 0.0115 | PNP | −1.6046 | 0.0227 |
| RP1-13D10.3 | 14.1048 | 0.001 | PNPLA8 | −1.3579 | 0.0116 |
| RP11-400N9.1 | 1.8375 | 0.0175 | PNPO | −1.3828 | 0.0117 |
| RP11-404G16.2 | 1.6715 | 0.0062 | POLDIP2 | −1.1824 | 0.0406 |
| RP11-406H21.2 | 9.4849 | 0.0052 | POLR1B | −1.5246 | 0.0101 |
| RP11-411B10.8 | 3.7692 | 0.0176 | POLR2A | −1.2205 | 0.049 |
| RP11-415F23.2 | 1.8197 | 0.0181 | POLR2B | −1.218 | 0.0321 |
| RP11-420L9.5 | 1.6608 | 0.0026 | POLR2C | −1.0917 | 0.0474 |
| RP11-421F16.3 | 2.0332 | 0.0339 | POLR3B | −1.3435 | 0.0227 |
| RP11-422P24.10 | 2.3777 | 0.0336 | POLR3D | −1.4924 | 0.0029 |
| RP11-426C22.4 | 2.1796 | 0.039 | POLR3E | −1.4484 | 0.0026 |
| RP11-426C22.5 | 2.9521 | 0.0493 | POLR3G | −1.379 | 0.0412 |
| RP11-430C7.5 | 3.4124 | 0.0159 | POMK | −2.2307 | 0.0195 |
| RP11-434D9.1 | 5.3861 | 0.019 | POP1 | −1.4374 | 0.007 |
| RP11-435J9.2 | 3.1332 | 0.0407 | PPFIBP2 | −1.2614 | 0.0457 |
| RP11-438B23.2 | 1.2211 | 0.032 | PPIAP31 | −5.4822 | 0.0087 |
| RP11-43F13.3 | 2.3244 | 0.0088 | PPID | −1.3041 | 0.0309 |
| RP11-452F19.3 | 1.9297 | 0.013 | PPIG | −1.2392 | 0.0254 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| RP11-452L6.1 | 1.8677 | 0.0461 | PPIL6 | −1.8959 | 0.0147 |
| RP11-452L6.7 | 3.2378 | 0.0131 | PPP1R15B | −1.2969 | 0.0178 |
| RP11-454P21.1 | 5.6966 | 0.0092 | PPP1R26P1 | −2.5585 | 0.0092 |
| RP11-455F5.6 | 1.9352 | 0.0498 | PPP1R3D | −1.1499 | 0.0247 |
| RP11-455O6.2 | 4.2202 | 0.0311 | PPP2CB | −1.2664 | 0.043 |
| RP11-460N11.2 | 2.4121 | 0.0283 | PPP2R2A | −1.3601 | 0.0249 |
| RP11-461F11.2 | 1.8676 | 0.0211 | PPP4R3A | −1.2058 | 0.0213 |
| RP11-463O9.9 | 2.6022 | 0.0465 | PPP6C | −1.0941 | 0.0393 |
| RP11-465N4.4 | 1.685 | 0.0369 | PPP6R3 | −1.099 | 0.016 |
| RP11-465N4.5 | 1.7406 | 0.0387 | PRDM4 | −1.1642 | 0.0364 |
| RP11-468E2.11 | 1.9722 | 0.0079 | PREB | −1.2718 | 0.0067 |
| RP11-46D6.1 | 1.7115 | 0.0127 | PRELID3B | −1.3839 | 0.027 |
| RP11-46F15.2 | 3.3584 | 0.0093 | PRKAR2A | −1.4367 | 0.0266 |
| RP11-472N13.3 | 3.9571 | 0.0426 | PRKCI | −1.2771 | 0.0271 |
| RP11-473M20.9 | 2.1831 | 0.0236 | PRKRIRP7 | −3.3795 | 0.0109 |
| RP11-474P2.7 | 2.0825 | 0.0169 | PRKX-AS1 | −1.7378 | 0.0333 |
| RP11-475B2.1 | 3.3804 | 0.0154 | PRKXP1 | −1.9833 | 0.0409 |
| RP11-477D19.2 | 1.607 | 0.0435 | PRMT3 | −1.3837 | 0.0466 |
| RP11-481J13.1 | 2.9248 | 0.0492 | PRMT5 | −1.3391 | 0.0041 |
| RP11-485G7.5 | 4.3861 | 0.0212 | PRMT9 | −1.4077 | 0.025 |
| RP11-496D24.2 | 3.4571 | 0.0093 | PROSC | −1.2063 | 0.0496 |
| RP11-506F3.1 | 2.1855 | 0.0066 | PRPF4 | −1.3202 | 0.0087 |
| RP11-506H21.5 | 3.6892 | 0.0022 | PRPF4B | −1.524 | 0.03 |
| RP11-50C13.1 | 2.1803 | 0.0049 | PRR14L | −1.3174 | 0.0188 |
| RP11-513O13.1 | 1.9855 | 0.013 | PRRC1 | −1.2096 | 0.0292 |
| RP11-521B24.5 | 9.693 | 0.035 | PRSS37 | −1.4143 | 0.0333 |
| RP11-522B15.3 | 2.8005 | 0.033 | PSEN1 | −1.2266 | 0.0123 |
| RP11-524D16__A.3 | 3.8643 | 0.0328 | PSMC1P1 | −1.5733 | 0.0387 |
| RP1-152L7.5 | 1.5684 | 0.0338 | PSMC4 | −1.2205 | 0.0141 |
| RP11-539L10.2 | 2.1106 | 0.0265 | PSMC6 | −1.1963 | 0.0344 |
| RP11-541N10.3 | 1.2713 | 0.0166 | PSMD10 | −1.203 | 0.0389 |
| RP11-544L8__B.4 | 2.0229 | 0.0315 | PSMD11 | −1.4077 | 0.008 |
| RP11-548P2.2 | 5.7418 | 0.0281 | PSMD2 | −1.2551 | 0.0429 |
| RP11-551L14.4 | 5.6123 | 0.0247 | PSMD3 | −1.2336 | 0.0226 |
| RP11-553L6.5 | 1.8926 | 0.0027 | PSMD5 | −1.1895 | 0.0046 |
| RP11-554D14.6 | 2.7443 | 0.0065 | PSME3 | −1.4749 | 0.0215 |
| RP11-566K19.6 | 2.6344 | 0.0187 | PSPH | −1.6523 | 0.0006 |
| RP11-577H5.1 | 1.8754 | 0.0097 | PTAFR | −1.462 | 0.0121 |
| RP11-57H14.5 | 3.6496 | 0.0021 | PTBP3 | −1.246 | 0.0318 |
| RP11-585P4.6 | 2.9839 | 0.0302 | PTEN | −1.1773 | 0.0207 |
| RP11-588H23.3 | 2.0784 | 0.0005 | PTPN11 | −1.3885 | 0.033 |
| RP11-5N19.3 | 3.5232 | 0.0283 | PTPN21 | −1.2808 | 0.0215 |
| RP11-635L1.3 | 2.9289 | 0.0477 | PTPRZ1 | −1.8102 | 0.0311 |
| RP11-637A17.2 | 2.5892 | 0.0387 | PVRIG2P | −7.374 | 0.0352 |
| RP11-63P12.7 | 2.3655 | 0.03 | PYURF | −1.2021 | 0.0489 |
| RP11-640I15.1 | 7.6695 | 0.003 | RAB10 | −1.3684 | 0.0391 |
| RP11-64P14.7 | 9.9162 | 0.0001 | RAB14 | −1.2357 | 0.0348 |
| RP11-656D10.5 | 4.1745 | 0.0073 | RAB1A | −1.2422 | 0.0331 |
| RP11-656D10.7 | 4.9998 | 0.0038 | RAB2A | −1.4831 | 0.0463 |
| RP11-662B19.2 | 2.9377 | 0.0472 | RAB35 | −1.1802 | 0.0317 |
| RP11-667F14.1 | 1.8266 | 0.0231 | RAB38 | −1.2537 | 0.0395 |
| RP11-676J12.7 | 2.9018 | 0.0186 | RAB3D | −1.5776 | 0.0082 |
| RP11-678G14.3 | 2.7865 | 0.0475 | RAB3GAP1 | −1.2971 | 0.0345 |
| RP11-686D22.4 | 1.9777 | 0.0403 | RAB6A | −1.2768 | 0.0041 |
| RP11-68I18.10 | 3.6063 | 0.0094 | RAB8A | −1.3861 | 0.0272 |
| RP1-168P16.2 | 3.5778 | 0.0281 | RAB9A | −1.1955 | 0.0284 |
| RP11-690G19.4 | 7.8425 | 0.0231 | RABGEF1 | −1.2682 | 0.0406 |
| RP11-6918.3 | 9.1128 | 0.0017 | RABIF | −1.1977 | 0.0263 |
| RP11-6J21.2 | 2.0495 | 0.0179 | RABL6 | −2.7957 | 0.0049 |
| RP11-6N17.2 | 2.7596 | 0.015 | RACGAP1 | −1.3426 | 0.0226 |
| RP11-707A18.1 | 2.7634 | 0.0141 | RAD1 | −1.2372 | 0.0162 |
| RP11-707G18.1 | 2.2203 | 0.0376 | RAD23B | −1.2912 | 0.0262 |
| RP11-70F11.2 | 5.2878 | 0.039 | RAD9B | −1.4964 | 0.0173 |
| RP1-170O19.14 | 3.6524 | 0.0066 | RAE1 | −1.1985 | 0.0411 |
| RP11-713M15.2 | 3.2102 | 0.0144 | RALBP1 | −1.3055 | 0.0268 |
| RP11-713N11.6 | 4.8464 | 0.0097 | RALGAPB | −1.139 | 0.0124 |
| RP11-718B12.2 | 4.9523 | 0.0053 | RANBP2 | −1.4234 | 0.018 |
| RP11-730A19.5 | 5.4488 | 0.0049 | RANBP3 | −1.1081 | 0.024 |
| RP11-73M7.6 | 5.5705 | 0.0382 | RAP1GDS1 | −1.1916 | 0.0251 |
| RP11-745O10.4 | 10.4813 | 0.0128 | RAP2C | −1.1902 | 0.0433 |
| RP11-748H22.1 | 2.0955 | 0.0388 | RBBP5 | −1.279 | 0.0149 |

TABLE 10-continued

Differentially Expressed Genes in the Skin Biopsies
of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| RP11-753N8.1 | 2.6418 | 0.0007 | RBM22 | −1.0986 | 0.0212 |
| RP11-759A24.1 | 1.5303 | 0.0072 | RBM26 | −1.3343 | 0.0482 |
| RP11-75A9.3 | 2.334 | 0.0119 | RBM38 | −1.3401 | 0.0079 |
| RP11-764K9.1 | 2.1169 | 0.0175 | RBM45 | −1.2118 | 0.0428 |
| RP11-771K4.3 | 2.6633 | 0.0483 | RBM47 | −1.2791 | 0.0247 |
| RP11-789C17.1 | 2.4871 | 0.0228 | RCC2 | −1.2579 | 0.0333 |
| RP11-796E10.1 | 7.4524 | 0.0304 | RCHY1 | −1.5939 | 0.0125 |
| RP11-798K3.3 | 3.7485 | 0.0398 | RCOR1 | −1.4299 | 0.0395 |
| RP11-798M19.6 | 1.7825 | 0.0207 | RDH11 | −1.3583 | 0.0038 |
| RP1-179N16.6 | 3.3485 | 0.0241 | RDH12 | −1.6237 | 0.0248 |
| RP11-812E19.3 | 3.5868 | 0.035 | RDH8 | −2.4046 | 0.0269 |
| RP11-81A1.4 | 1.4688 | 0.0311 | REEP3 | −1.2004 | 0.0142 |
| RP11-81A1.6 | 1.3603 | 0.0242 | REXO2 | −1.1681 | 0.0038 |
| RP11-81H14.2 | 6.0557 | 0.0097 | RFWD3 | −1.297 | 0.0287 |
| RP11-824M15.3 | 2.2408 | 0.0324 | RGP1 | −1.3573 | 0.009 |
| RP1-182O16.2 | 4.8261 | 0.0003 | RHOT1 | −1.331 | 0.0223 |
| RP11-831A10.1 | 4.1232 | 0.0266 | RIC8A | −1.128 | 0.016 |
| RP11-834C11.5 | 4.8219 | 0.009 | RIC8B | −1.4012 | 0.0019 |
| RP11-834C11.8 | 7.8636 | 0.0211 | RIMBP3C | −4.4556 | 0.0304 |
| RP11-848P1.4 | 2.0391 | 0.0124 | RINT1 | −1.2269 | 0.0191 |
| RP11-84D1.1 | 3.4736 | 0.0292 | RIT1 | −1.3604 | 0.0003 |
| RP11-861E21.2 | 2.2882 | 0.0473 | RN7SKP198 | −2.0173 | 0.0333 |
| RP11-863P13.3 | 3.1094 | 0.0161 | RN7SKP69 | −2.0193 | 0.0333 |
| RP11-885N19.6 | 3.529 | 0.037 | RN7SL124P | −2.0605 | 0.0333 |
| RP11-89K11.1 | 2.8447 | 0.004 | RN7SL12P | −6.7849 | 0.0376 |
| RP1-18D14.7 | 1.866 | 0.0263 | RN7SL172P | −2.0232 | 0.0333 |
| RP11-90C4.1 | 5.25 | 0.0116 | RN7SL199P | −3.0637 | 0.0239 |
| RP11-91P24.5 | 5.611 | 0.0151 | RN7SL656P | −3.0637 | 0.0239 |
| RP11-92G12.3 | 3.3427 | 0.0416 | RN7SL793P | −3.6489 | 0.0466 |
| RP11-936I5.1 | 2.7301 | 0.0008 | RNA5SP187 | −2.7052 | 0.0333 |
| RP11-93H24.3 | 1.7504 | 0.0103 | RNASEH2B-AS1 | −3.7098 | 0.0364 |
| RP11-950C14.7 | 6.1553 | 0.0014 | RNASEL | −1.2608 | 0.0421 |
| RP11-95D17.1 | 1.4093 | 0.0261 | RNF10 | −1.1669 | 0.0206 |
| RP11-964E11.2 | 3.3828 | 0.0208 | RNF114 | −1.133 | 0.0469 |
| RP11-964E11.3 | 2.9209 | 0.0083 | RNF149 | −1.2601 | 0.0076 |
| RP11-96B5.3 | 6.4352 | 0.0009 | RNF185 | −1.2157 | 0.0094 |
| RP11-96L14.7 | 1.9854 | 0.0197 | RNF2 | −1.3763 | 0.0046 |
| RP11-983P16.4 | 1.7604 | 0.0025 | RNF20 | −1.3767 | 0.026 |
| RP11-989F5.4 | 3.9516 | 0.0273 | RNF216 | −1.2185 | 0.0131 |
| RP11-998D10.4 | 2.6381 | 0.0492 | RNF40 | −1.2962 | 0.0015 |
| RP1-244F24.1 | 2.0485 | 0.0266 | RNF41 | −1.2715 | 0.0089 |
| RP1-290F12.3 | 2.7334 | 0.0463 | RNF6 | −1.3743 | 0.0356 |
| RP1-302D9.3 | 4.4713 | 0.0433 | RNF8 | −1.3125 | 0.0091 |
| RP1-310O13.7 | 2.9112 | 0.0162 | RNFT1 | −1.1998 | 0.0185 |
| RP13-131K19.2 | 6.2305 | 0.048 | RNGTT | −1.2634 | 0.0183 |
| RP13-147D17.3 | 1.4294 | 0.0362 | RNU2-25P | −2.3286 | 0.0333 |
| RP13-16H11.8 | 2.1917 | 0.0265 | RNU2-27P | −12.5178 | 0.0124 |
| RP13-20L14.4 | 2.6538 | 0.035 | RP11-1007O24.3 | −1.615 | 0.0147 |
| RP13-507P19.2 | 2.4708 | 0.0007 | RP11-100G15.12 | −3.4993 | 0.019 |
| RP13-516M14.2 | 4.0684 | 0.025 | RP11-1017G21.4 | −5.3771 | 0.0082 |
| RP13-726E6.2 | 4.8286 | 0.000035741 | RP11-10J21.3 | −1.6808 | 0.0333 |
| RP13-870H17.3 | 2.696 | 0.0436 | RP11-10L12.1 | −2.1307 | 0.0333 |
| RP13-895J2.4 | 1.7363 | 0.0016 | RP11-111K18.1 | −1.1726 | 0.0424 |
| RP1-39G22.7 | 1.2317 | 0.032 | RP11-114H23.1 | −4.3517 | 0.0344 |
| RP1-40E16.11 | 23.5044 | 0.0311 | RP11-115C21.2 | −1.3385 | 0.0233 |
| RP1-47M23.3 | 2.4588 | 0.0264 | RP11-115N12.1 | −2.9306 | 0.035 |
| RP1-68D18.3 | 2.6527 | 0.0006 | RP11-116B13.1 | −2.7147 | 0.0395 |
| RP1-8B1.4 | 4.4401 | 0.0131 | RP11-1223D19.3 | −6.6167 | 0.0163 |
| RP3-395M20.8 | 1.7263 | 0.0251 | RP11-1228E12.2 | −2.0504 | 0.046 |
| RP3-454B23.1 | 2.4394 | 0.0007 | RP11-127B16.1 | −2.3705 | 0.0476 |
| RP3-460G2.2 | 5.9962 | 0.0085 | RP11-129B9.1 | −1.6475 | 0.0333 |
| RP3-465N24.5 | 9.9304 | 0.0318 | RP11-138I18.1 | −3.8433 | 0.0438 |
| RP3-495K2.2 | 2.7532 | 0.016 | RP11-14N9.1 | −1.6653 | 0.0329 |
| RP3-508I15.9 | 1.4036 | 0.0488 | RP11-159D12.8 | −1.2541 | 0.0382 |
| RP3-522D1.1 | 9.3237 | 0.0056 | RP11-15E18.5 | −1.9218 | 0.0333 |
| RP3-525N10.2 | 2.8087 | 0.0035 | RP11-15J10.1 | −3.487 | 0.0494 |
| RP4-593H12.1 | 6.9334 | 0.0332 | RP11-175B9.2 | −2.9644 | 0.0206 |
| RP4-620F22.2 | 4.0932 | 0.0401 | RP11-175I6.1 | −2.6823 | 0.0333 |
| RP4-621F18.2 | 2.6497 | 0.0464 | RP11-179A10.2 | −1.369 | 0.0333 |
| RP4-635E18.7 | 1.7798 | 0.0342 | RP11-196I18.4 | −2.4402 | 0.0333 |
| RP4-639F20.1 | 2.0451 | 0.0112 | RP11-1D12.1 | −1.8872 | 0.0333 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| RP4-717I23.3 | 1.4663 | 0.0334 | RP11-239L20.6 | −1.8151 | 0.0333 |
| RP4-758J18.10 | 1.9429 | 0.0406 | RP11-245C17.2 | −2.9599 | 0.0468 |
| RP4-760C5.3 | 4.2537 | 0.0304 | RP11-251G23.5 | −1.3461 | 0.0154 |
| RP4-791M13.3 | 6.1676 | 0.0114 | RP11-255A11.2 | −2.6189 | 0.0333 |
| RP4-800G7.2 | 1.897 | 0.0043 | RP11-255H23.5 | −4.3006 | 0.0333 |
| RP4-800M22.1 | 3.1071 | 0.0346 | RP11-256I9.3 | −1.5597 | 0.0333 |
| RP5-1009E24.9 | 5.2914 | 0.0102 | RP11-258F1.2 | −1.7201 | 0.0365 |
| RP5-1024N4.4 | 2.0167 | 0.013 | RP11-262H14.5 | −1.8431 | 0.0279 |
| RP5-1065J22.4 | 3.8904 | 0.022 | RP11-26J3.4 | −1.7694 | 0.0208 |
| RP5-1068E13.7 | 1.6402 | 0.04 | RP11-271K21.12 | −2.2215 | 0.0038 |
| RP5-1110E20.1 | 6.8716 | 0.007 | RP11-27I1.4 | −1.8324 | 0.0448 |
| RP5-1116H23.4 | 6.2031 | 0.0241 | RP11-297L17.6 | −1.5814 | 0.0333 |
| RP5-1174N9.2 | 3.0185 | 0.0472 | RP11-298J20.4 | −2.5182 | 0.0099 |
| RP5-855D21.2 | 2.8255 | 0.0092 | RP11-29G8.3 | −1.6703 | 0.0007 |
| RP5-890O3.3 | 7.4445 | 0.0256 | RP11-305F5.2 | −1.6104 | 0.0333 |
| RP5-940J5.3 | 5.5703 | 0.0222 | RP11-30H9.1 | −1.98 | 0.0324 |
| RP5-965F6.2 | 3.1211 | 0.0298 | RP11-317B3.2 | −1.7006 | 0.0333 |
| RP5-997D16.2 | 1.5302 | 0.029 | RP11-317B7.2 | −1.2888 | 0.0333 |
| RP6-201G10.2 | 3.8022 | 0.0235 | RP11-318M2.3 | −2.1635 | 0.0333 |
| RP6-65G23.5 | 6.7707 | 0.0371 | RP11-322D14.1 | −2.7776 | 0.0223 |
| RP9P | 1.2957 | 0.0314 | RP11-332J15.4 | −3.4921 | 0.0473 |
| RPL13AP5 | 2.1261 | 0.0314 | RP11-344B5.2 | −2.6617 | 0.0039 |
| RPL13P6 | 2.4903 | 0.0007 | RP11-346M5.1 | −5.436 | 0.0468 |
| RPL23AP1 | 2.9498 | 0.0041 | RP11-351I21.7 | −4.3109 | 0.0229 |
| RPL23AP2 | 3.1822 | 0.0051 | RP11-359E8.5 | −1.5969 | 0.0333 |
| RPL23AP48 | 5.684 | 0.0109 | RP11-366I13.3 | −1.8209 | 0.0333 |
| RPL23AP86 | 3.8671 | 0.0055 | RP11-36C20.1 | −4.6232 | 0.0058 |
| RPL34P22 | 7.5172 | 0.0088 | RP11-379F12.3 | −6.2919 | 0.0478 |
| RPL36P4 | 5.9168 | 0.016 | RP11-379F12.4 | −3.9024 | 0.0432 |
| RPL7L1P8 | 2.2769 | 0.0226 | RP11-380I10.4 | −1.5121 | 0.0333 |
| RPL7P21 | 4.5697 | 0.0176 | RP11-387D10.4 | −2.5443 | 0.0435 |
| RPS20P35 | 6.5729 | 0.0387 | RP11-390F4.2 | −2.4355 | 0.0333 |
| RRAGB | 1.2 | 0.0308 | RP11-397G17.1 | −2.1968 | 0.0333 |
| RRAS | 1.4715 | 0.0421 | RP11-39E3.3 | −1.9557 | 0.0333 |
| RSL24D1P6 | 5.4355 | 0.0404 | RP11-39E3.4 | −1.6901 | 0.0333 |
| RTCA-AS1 | 1.7894 | 0.0492 | RP11-400F19.6 | −1.2873 | 0.0002 |
| RTEL1-TNFRSF6B | 1.8023 | 0.0416 | RP11-403A3.1 | −1.3142 | 0.0333 |
| RUNX1T1 | 2.1115 | 0.0042 | RP11-409O11.3 | −1.7131 | 0.0333 |
| S100A13 | 1.6017 | 0.0219 | RP11-415C15.2 | −1.21 | 0.0333 |
| S100A4 | 1.5652 | 0.0301 | RP11-425M5.7 | −5.5746 | 0.0333 |
| S100B | 1.4463 | 0.0495 | RP11-426C22.6 | −3.807 | 0.0149 |
| SAA4 | 6.167 | 0.0143 | RP11-426K3.1 | −2.571 | 0.0333 |
| SARM1 | 1.5202 | 0.0315 | RP11-434H6.2 | −2.6579 | 0.0281 |
| SATB2 | 1.4738 | 0.0378 | RP11-438J1.1 | −2.1634 | 0.012 |
| SCARF2 | 1.7001 | 0.003 | RP11-439M15.1 | −8.6276 | 0.0199 |
| SCARNA7 | 8.7685 | 0.0261 | RP11-43A14.2 | −2.1049 | 0.028 |
| SCG5 | 1.971 | 0.018 | RP11-442H21.2 | −2.3234 | 0.0333 |
| SCRT1 | 1.5259 | 0.0398 | RP11-443C10.2 | −1.9234 | 0.0333 |
| SCUBE1 | 3.3202 | 0.0051 | RP11-446E24.4 | −1.9005 | 0.0219 |
| SDK1 | 1.8652 | 0.0037 | RP11-447D11.3 | −2.0273 | 0.0105 |
| SELENBP1 | 1.7191 | 0.0252 | RP11-449H3.3 | −6.7409 | 0.0241 |
| SELV | 1.9487 | 0.0109 | RP11-452D12.1 | −2.2524 | 0.0215 |
| SEMA3A | 1.8091 | 0.0482 | RP11-452L6.5 | −1.4994 | 0.0274 |
| SEMA3B | 1.935 | 0.0127 | RP11-456J20.1 | −1.2342 | 0.0333 |
| SEMA3G | 1.7597 | 0.0402 | RP11-458D21.1 | −2.1499 | 0.0173 |
| SEMA6D | 1.5348 | 0.0423 | RP11-463D19.1 | −2.753 | 0.0438 |
| SEPT4-AS1 | 3.6154 | 0.0202 | RP11-466A19.7 | −2.0096 | 0.0061 |
| SERPINA5 | 3.3288 | 0.031 | RP11-474D14.2 | −6.2422 | 0.0321 |
| SERPINF1 | 1.8299 | 0.0059 | RP11-478B9.1 | −1.9092 | 0.0333 |
| SESTD1 | 1.2858 | 0.0266 | RP11-483E23.2 | −1.4979 | 0.0333 |
| SFTA1P | 3.172 | 0.0491 | RP11-488I20.9 | −1.6319 | 0.0371 |
| SGIP1 | 1.856 | 0.0236 | RP11-496N12.9 | −1.7006 | 0.0333 |
| SGMS1-AS1 | 1.3618 | 0.0048 | RP11-504I13.2 | −1.5474 | 0.025 |
| SHCBP1 | 1.4235 | 0.0249 | RP11-506E9.3 | −2.4256 | 0.0333 |
| SHISA9 | 1.5061 | 0.0234 | RP11-50B3.4 | −4.0618 | 0.0271 |
| SHOX2 | 1.7191 | 0.0295 | RP11-510J16.5 | −2.1866 | 0.0103 |
| SIAH2-AS1 | 5.4984 | 0.0086 | RP11-517A5.5 | −3.9594 | 0.0173 |
| SIGIRR | 1.5992 | 0.0292 | RP11-525G13.2 | −4.9209 | 0.0258 |
| SKOR1 | 1.9496 | 0.0346 | RP11-529J17.3 | −2.0261 | 0.0333 |
| SLC12A5 | 4.0123 | 0.0074 | RP11-542A14.1 | −3.8213 | 0.0425 |
| SLC1A7 | 2.0812 | 0.0414 | RP11-549L6.2 | −2.1872 | 0.0333 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| SLC22A17 | 1.6468 | 0.0405 | RP11-54D18.4 | −1.4745 | 0.0333 |
| SLC25A1P5 | 6.0336 | 0.0481 | RP11-54G14.1 | −5.4656 | 0.0215 |
| SLC25A20 | 1.3228 | 0.0334 | RP11-565P22.6 | −5.7881 | 0.0067 |
| SLC25A45 | 1.6808 | 0.0152 | RP11-567I13.1 | −2.016 | 0.0333 |
| SLC27A1 | 1.4218 | 0.0166 | RP11-567O16.1 | −2.2729 | 0.0333 |
| SLC29A3 | 1.4369 | 0.0111 | RP11-568A7.1 | −11.0414 | 0.009 |
| SLC2A10 | 1.7906 | 0.0465 | RP11-568J23.2 | −1.4658 | 0.0313 |
| SLC36A2 | 1.7595 | 0.0185 | RP11-56L13.3 | −2.2007 | 0.0333 |
| SLC38A11 | 2.4871 | 0.0323 | RP11-574F21.3 | −3.1223 | 0.0316 |
| SLC40A1 | 1.3426 | 0.0382 | RP11-614F17.1 | −1.9457 | 0.0333 |
| SLC45A1 | 1.7058 | 0.0409 | RP11-615J4.4 | −2.2662 | 0.0333 |
| SLC4A4 | 1.8932 | 0.0388 | RP11-624D20.1 | −1.4941 | 0.0333 |
| SLC5A8 | 3.3505 | 0.0134 | RP11-629N8.5 | −3.5145 | 0.0333 |
| SLC6A7 | 1.9826 | 0.0383 | RP11-648O15.1 | −2.1381 | 0.0289 |
| SLIT1 | 1.8036 | 0.0174 | RP11-661A12.4 | −2.932 | 0.0304 |
| SLIT3 | 2.0824 | 0.0461 | RP11-667M19.1 | −2.4106 | 0.0333 |
| SLITRK5 | 1.8059 | 0.0116 | RP11-676M6.1 | −2.7336 | 0.0106 |
| SMIM10L2A | 2.0529 | 0.0019 | RP11-67C2.2 | −8.3867 | 0.0201 |
| SNCG | 2.106 | 0.0263 | RP11-680F20.6 | −2.3493 | 0.0464 |
| SNED1 | 1.8562 | 0.0264 | RP11-689J19.1 | −2.8786 | 0.0498 |
| SNORA41 | 3.4379 | 0.0225 | RP1-168P16.1 | −1.8465 | 0.0333 |
| SNORA5A | 7.098 | 0.0188 | RP1-170O19.23 | −11.2381 | 0.0145 |
| SOD3 | 2.0999 | 0.025 | RP11-712P20.2 | −1.7396 | 0.016 |
| SOX13 | 1.6833 | 0.0126 | RP11-724N1.1 | −2.6893 | 0.0351 |
| SPATC1 | 2.8239 | 0.0143 | RP11-73M18.7 | −1.5241 | 0.0277 |
| SPEF2 | 1.5663 | 0.036 | RP11-753B14.1 | −3.6135 | 0.0477 |
| SPG20-AS1 | 7.262 | 0.0051 | RP11-802D6.1 | −4.6809 | 0.0032 |
| SPINK4 | 3.9741 | 0.0424 | RP11-80H18.3 | −1.4473 | 0.0487 |
| SPNS3 | 1.9415 | 0.0439 | RP11-844P9.1 | −2.3847 | 0.0333 |
| SRGAP1 | 1.5386 | 0.0131 | RP11-844P9.2 | −1.1683 | 0.0333 |
| SRP14-AS1 | 1.6757 | 0.0092 | RP11-881M11.1 | −1.8593 | 0.0333 |
| SRPK3 | 1.9519 | 0.0195 | RP11-88I21.1 | −2.879 | 0.0331 |
| SSC5D | 2.6389 | 0.0359 | RP11-894J14.5 | −2.2024 | 0.0406 |
| SSPN | 1.7641 | 0.0254 | RP11-94B19.6 | −2.1929 | 0.0333 |
| ST13P5 | 2.4571 | 0.0429 | RP11-94B19.7 | −2.0313 | 0.0333 |
| STC2 | 2.2078 | 0.0337 | RP11-958J22.2 | −3.2102 | 0.0477 |
| STK31 | 3.9771 | 0.0019 | RP11-978I15.10 | −3.1162 | 0.0475 |
| STK32B | 1.8474 | 0.0269 | RP11-99E15.2 | −2.2281 | 0.0474 |
| STMN2 | 4.3189 | 0.0083 | RP1-266L20.2 | −5.2394 | 0.0336 |
| STMN3 | 1.4198 | 0.0196 | RP1-272L16.1 | −4.6029 | 0.0176 |
| SUN3 | 3.2768 | 0.0045 | RP1-308E4.1 | −2.3064 | 0.0333 |
| SVBP | 1.316 | 0.0498 | RP13-650J16.1 | −3.1872 | 0.039 |
| SYBU | 1.6778 | 0.0099 | RP13-895J2.11 | −1.7173 | 0.0333 |
| SYCP2L | 3.1379 | 0.0413 | RP1-63G5.8 | −2.3106 | 0.0198 |
| SYDE1 | 1.6779 | 0.0196 | RP1-69M21.2 | −1.6391 | 0.0333 |
| SYNDIG1 | 2.3614 | 0.0064 | RP1-93H18.6 | −2.1061 | 0.0333 |
| SYNE3 | 1.4909 | 0.0051 | RP3-333A15.1 | −2.7422 | 0.0261 |
| SYT16 | 1.1869 | 0.0204 | RP3-468K18.7 | −2.0836 | 0.0333 |
| SYTL4 | 1.8005 | 0.0189 | RP3-507I15.2 | −1.9328 | 0.0333 |
| TAS2R15P | 2.6626 | 0.0359 | RP4-545C24.5 | −1.7636 | 0.0333 |
| TAS2R19 | 4.7903 | 0.0133 | RP4-635A23.3 | −1.8879 | 0.0333 |
| TAS2R20 | 2.4475 | 0.0236 | RP4-675C20.4 | −2.3152 | 0.0438 |
| TAS2R5 | 1.6319 | 0.0446 | RP4-724E16.2 | −1.8296 | 0.0323 |
| TBC1D3P2 | 2.2383 | 0.0088 | RP4-777O23.3 | −5.3522 | 0.0412 |
| TBX15 | 2.344 | 0.0024 | RP5-1154E9.7 | −1.5782 | 0.0333 |
| TBX18 | 2.5027 | 0.0048 | RP5-1170K4.7 | −1.7895 | 0.0333 |
| TCF21 | 2.8128 | 0.0455 | RPA1 | −1.1916 | 0.0484 |
| TCF23 | 2.6569 | 0.0347 | RPAP2 | −1.4134 | 0.0039 |
| TCF4-AS1 | 6.8883 | 0.0028 | RPF1 | −1.2056 | 0.0316 |
| TCF7L1 | 2.0377 | 0.0039 | RPL17-C18orf32 | −2.1748 | 0.0126 |
| TCTN1 | 1.2625 | 0.0177 | RPL17P51 | −2.1759 | 0.0333 |
| TDH | 4.4833 | 0.0046 | RPL21P106 | −1.7747 | 0.0333 |
| TENM1 | 1.8425 | 0.002 | RPL23AP50 | −2.5386 | 0.0387 |
| TEX35 | 5.1938 | 0.0109 | RPL29P12 | −5.892 | 0.0473 |
| TEX40 | 4.0228 | 0.0268 | RPL32P31 | −1.862 | 0.0333 |
| TFCP2L1 | 1.3389 | 0.034 | RPL39P5 | −4.6969 | 0.0317 |
| TGFB2-OT1 | 15.4989 | 0.0234 | RPL4P6 | −2.7556 | 0.0015 |
| THAP9-AS1 | 1.4167 | 0.0308 | RPL7AP31 | −2.0186 | 0.0467 |
| THBS3 | 1.4269 | 0.0199 | RPL7L1 | −1.2372 | 0.0007 |
| THRA | 1.4288 | 0.0308 | RPN2 | −1.2469 | 0.0248 |
| TIAM2 | 1.8663 | 0.0027 | RPP14 | −1.1838 | 0.0216 |

TABLE 10-continued

Differentially Expressed Genes in the Skin Biopsies
of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| TICAM2 | 1.6668 | 0.0223 | RPRD1A | −1.2387 | 0.0055 |
| TIMP2 | 1.6015 | 0.0313 | RPRD1B | −1.1958 | 0.0089 |
| TIMP3 | 1.8886 | 0.0357 | RPRD2 | −1.389 | 0.0231 |
| TIMP4 | 3.788 | 0.0257 | RPS26P13 | −2.4379 | 0.0333 |
| TLE2 | 1.5209 | 0.0323 | RPS28P7 | −2.0109 | 0.0194 |
| TLN2 | 1.4569 | 0.0392 | RPS4XP5 | −2.1789 | 0.0347 |
| TLR6 | 1.7163 | 0.0086 | RPS6KA2 | −1.1551 | 0.0279 |
| TM6SF2 | 2.6728 | 0.0344 | RPS6KB1 | −1.4785 | 0.0184 |
| TMEM133 | 1.5221 | 0.004 | RPS9P1 | −5.8933 | 0.0376 |
| TMEM176A | 1.553 | 0.0385 | RPSAP13 | −3.6691 | 0.0164 |
| TMEM176B | 1.7832 | 0.0084 | RPTOR | −1.3022 | 0.0038 |
| TMEM178A | 2.1052 | 0.0237 | RTF1 | −1.1954 | 0.0329 |
| TMEM190 | 4.9423 | 0.048 | RUNDC1 | −1.2114 | 0.0381 |
| TMEM61 | 1.8418 | 0.0449 | SAP130 | −1.1379 | 0.0111 |
| TMEM71 | 1.9491 | 0.0018 | SAPCD2 | −1.3136 | 0.0351 |
| TMEM8B | 1.5925 | 0.0138 | SAR1B | −1.438 | 0.0139 |
| TMPRSS15 | 1.388 | 0.0447 | SARS | −1.2383 | 0.0098 |
| TMPRSS3 | 3.6822 | 0.0034 | SART3 | −1.2063 | 0.0127 |
| TMPRSS5 | 2.5013 | 0.015 | SBDS | −1.242 | 0.0445 |
| TMSB15B | 1.6412 | 0.0135 | SBNO1 | −1.3987 | 0.0196 |
| TNFRSF14 | 1.6189 | 0.0215 | SC5D | −1.4223 | 0.0338 |
| TNFSF12 | 1.6455 | 0.0201 | SCAF11 | −1.3698 | 0.0473 |
| TNFSF12-TNFSF13 | 32.0013 | 0.0066 | SCAMP1 | −1.354 | 0.0265 |
| TNIK | 1.8778 | 0.0153 | SCAMP2 | −1.2297 | 0.0314 |
| TNMD | 5.2248 | 0.0038 | SCD | −1.9615 | 0.009 |
| TNS2 | 1.8287 | 0.0187 | SCO1 | −1.2137 | 0.0352 |
| TNS3 | 1.3413 | 0.0029 | SCYL2 | −1.4369 | 0.0236 |
| TNXA | 13.8375 | 0.0072 | SDE2 | −1.2889 | 0.0447 |
| TOX | 1.7266 | 0.0488 | SDHAF2 | −1.1628 | 0.0353 |
| TPK1 | 1.3826 | 0.0077 | SDR42E1 | −1.2541 | 0.0195 |
| TPT1-AS1 | 1.772 | 0.0041 | SEC22A | −1.3598 | 0.0085 |
| TPTE2 | 2.262 | 0.0402 | SEC23B | −1.5582 | 0.0164 |
| TRABD2A | 1.7184 | 0.0343 | SEC23IP | −1.4253 | 0.0273 |
| TRAF3IP2-AS1 | 1.5275 | 0.0171 | SEC24A | −1.534 | 0.0429 |
| TRAF5 | 1.5778 | 0.0074 | SEC24C | −1.2964 | 0.0437 |
| TRAM2-AS1 | 1.5947 | 0.0235 | SEC63P1 | −2.6944 | 0.0186 |
| TRAV25 | 5.0926 | 0.0409 | SEH1L | −1.2285 | 0.0493 |
| TRAV8-1 | 4.333 | 0.0221 | SELT | −1.356 | 0.0275 |
| TRBC1 | 1.7078 | 0.03 | SENP1 | −1.3196 | 0.0368 |
| TRBV4-1 | 6.9827 | 0.0313 | SENP2 | −1.1866 | 0.0433 |
| TRGC2 | 2.3482 | 0.0098 | SEPHS2 | −1.4069 | 0.0404 |
| TRIM52 | 1.3798 | 0.0376 | SERAC1 | −1.3286 | 0.002 |
| TRIM54 | 2.1377 | 0.0386 | SERBP1 | −1.4092 | 0.0134 |
| TRIM71 | 1.2324 | 0.0199 | SERBP1P6 | −2.7688 | 0.0408 |
| TRIM80P | 1.6674 | 0.0448 | SERINC3 | −1.1672 | 0.0356 |
| TRIO | 1.3507 | 0.0242 | SERINC5 | −1.3904 | 0.0489 |
| TRIP10 | 1.3458 | 0.0421 | SERP1 | −1.3424 | 0.0309 |
| TRO | 1.8188 | 0.007 | SERPINB5 | −1.6003 | 0.0436 |
| TRPC1 | 1.5694 | 0.0008 | SETD3 | −1.1839 | 0.0206 |
| TRPC4 | 2.1669 | 0.0247 | SETD7 | −1.3647 | 0.0184 |
| TRPC5 | 1.7127 | 0.041 | SETD8 | −1.2034 | 0.0144 |
| TRPM2 | 1.8019 | 0.0197 | SETP20 | −3.9672 | 0.0006 |
| TSPAN18 | 2.0263 | 0.0018 | SETX | −1.2192 | 0.0185 |
| TSPAN32 | 2.4293 | 0.0043 | SFPQ | −1.3872 | 0.0243 |
| TSPYL2 | 1.4519 | 0.05 | SFTPB | −1.5482 | 0.0324 |
| TSSC2 | 2.3538 | 0.0141 | SGOL2 | −1.3858 | 0.048 |
| TSTD3 | 1.5654 | 0.0087 | SGPL1 | −1.3117 | 0.0293 |
| TTC28 | 1.4465 | 0.0048 | SGPP2 | −2.0091 | 0.0362 |
| TTLL3 | 2.0123 | 0.0269 | SH3GLB1 | −1.264 | 0.0043 |
| TUBB8P11 | 4.2253 | 0.0223 | SHOC2 | −1.3038 | 0.036 |
| U47924.32 | 5.0364 | 0.0052 | SHQ1 | −1.323 | 0.0206 |
| U73166.2 | 1.6394 | 0.0259 | SIGMAR1 | −1.2888 | 0.0121 |
| UBE2E1-AS1 | 5.5735 | 0.0084 | SKE1 | −1.2485 | 0.021 |
| UBL4B | 3.0354 | 0.0109 | SKP1 | −1.2365 | 0.0231 |
| UCHL1 | 1.5228 | 0.0299 | SKP2 | −1.2698 | 0.0475 |
| UGT1A10 | 2.1096 | 0.0209 | SLC16A13 | −1.871 | 0.0128 |
| UMODL1 | 1.55 | 0.0489 | SLC25A15 | −1.6636 | 0.0377 |
| UNQ6494 | 2.6311 | 0.0135 | SLC25A39P1 | −3.8947 | 0.0346 |
| UROC1 | 1.409 | 0.0493 | SLC25A44 | −1.349 | 0.0011 |
| USHBP1 | 1.6783 | 0.023 | SLC30A5 | −1.2523 | 0.0127 |
| VCPKMT | 1.2257 | 0.0457 | SLC30A6 | −1.271 | 0.0053 |

TABLE 10-continued

Differentially Expressed Genes in the Skin Biopsies
of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| VDAC1P8 | 1.582 | 0.0496 | SLC31A1 | −1.5992 | 0.042 |
| VGLL3 | 1.7933 | 0.0204 | SLC33A1 | −1.5644 | 0.0098 |
| VILL | 1.2976 | 0.0077 | SLC35A2 | −1.3735 | 0.0005 |
| VSTM5 | 2.1036 | 0.0497 | SLC35A4 | −1.1999 | 0.0264 |
| VWA5B2 | 2.1039 | 0.022 | SLC35C1 | −1.2386 | 0.0472 |
| VWCE | 2.4853 | 0.03 | SLC35F5 | −1.5847 | 0.0331 |
| WASH2P | 1.5174 | 0.0415 | SLC37A3 | −1.1418 | 0.019 |
| WDR86 | 3.2208 | 0.0004 | SLC38A9 | −1.2497 | 0.0108 |
| WISP2 | 2.7922 | 0.0237 | SLC39A6 | −1.4519 | 0.0434 |
| XKR4 | 1.8271 | 0.0481 | SLC4A1AP | −1.1793 | 0.0293 |
| XPNPEP2 | 2.6522 | 0.0093 | SLC4A8 | −1.9298 | 0.0406 |
| XX-C00717C00720L.1 | 2.0535 | 0.042 | SLC52A3 | −1.7429 | 0.0289 |
| XXYLT1-AS2 | 5.6 | 0.0048 | SLC6A2 | −2.2444 | 0.0186 |
| YBX1P4 | 3.6625 | 0.0078 | SMARCA4 | −1.1684 | 0.0013 |
| YES1P1 | 4.2543 | 0.003 | SMARCA5 | −1.3757 | 0.0353 |
| YPEL1 | 1.7602 | 0.0305 | SMCR8 | −1.3634 | 0.0196 |
| YWHAQP7 | 3.4966 | 0.0007 | SMG7 | −1.2001 | 0.0005 |
| YWHAZP4 | 3.6956 | 0.0044 | SMG8 | −1.2828 | 0.0279 |
| Z69890.1 | 4.4301 | 0.04 | SMIM13 | −1.3175 | 0.0083 |
| ZBED3-AS1 | 2.1768 | 0.0293 | SMIM15 | −1.4856 | 0.0076 |
| ZBTB16 | 2.8553 | 0.0177 | SMIM2-AS1 | −3.8144 | 0.0327 |
| ZCCHC5 | 3.3388 | 0.0397 | SMNDC1 | −1.304 | 0.0445 |
| ZDHHC17 | 1.3253 | 0.0029 | SMU1 | −1.2623 | 0.0071 |
| ZEB2-AS1 | 4.2172 | 0.0241 | SNAP29 | −1.2973 | 0.0224 |
| ZKSCAN8 | 1.3159 | 0.0373 | SNORA16A | −2.0493 | 0.0483 |
| ZMAT1 | 2.6647 | 0.0012 | SNX1 | −1.2304 | 0.0103 |
| ZNF160 | 1.3868 | 0.0356 | SNX11 | −1.291 | 0.0001 |
| ZNF177 | 4.1639 | 0.0133 | SNX12 | −1.1667 | 0.0116 |
| ZNF192P1 | 2.5255 | 0.0383 | SNX18P24 | −1.6203 | 0.0333 |
| ZNF224 | 1.6086 | 0.0177 | SNX18P9 | −3.4886 | 0.0394 |
| ZNF25 | 1.3894 | 0.0057 | SNX19 | −1.2616 | 0.0393 |
| ZNF251 | 1.376 | 0.0325 | SNX27 | −1.2029 | 0.02 |
| ZNF26 | 1.4699 | 0.0391 | SNX4 | −1.2999 | 0.0331 |
| ZNF32-AS1 | 8.7542 | 0.0015 | SNX6 | −1.3464 | 0.0497 |
| ZNF345 | 1.3591 | 0.0048 | SOCS5P4 | −2.9872 | 0.0051 |
| ZNF358 | 1.543 | 0.0202 | SOCS7 | −1.3583 | 0.002 |
| ZNF37BP | 1.4674 | 0.0357 | SOGA1 | −1.2603 | 0.0281 |
| ZNF419 | 1.5094 | 0.0235 | SOX21-AS1 | −1.3179 | 0.0382 |
| ZNF432 | 1.3034 | 0.0476 | SPAST | −1.5285 | 0.0247 |
| ZNF441 | 1.4439 | 0.0043 | SPATA2L | −1.2303 | 0.035 |
| ZNF528-AS1 | 2.0712 | 0.0205 | SPATA5L1 | −1.3277 | 0.008 |
| ZNF529-AS1 | 1.596 | 0.0249 | SPECC1L | −1.3176 | 0.0073 |
| ZNF559 | 1.5759 | 0.0245 | SPG20 | −1.3842 | 0.009 |
| ZNF613 | 1.2468 | 0.0171 | SPOP | −1.2781 | 0.0346 |
| ZNF676 | 2.6849 | 0.0113 | SPRYD7 | −1.1621 | 0.032 |
| ZNF773 | 1.2703 | 0.0088 | SPTLC1 | −1.4679 | 0.0156 |
| ZNF80 | 3.2852 | 0.025 | SPTLC3 | −1.4833 | 0.0482 |
| ZNF836 | 1.4071 | 0.0083 | SPTY2D1 | −1.4877 | 0.0082 |
| ZNF841 | 1.3309 | 0.0447 | SQLE | −1.7533 | 0.0138 |
| ZNF880 | 1.3809 | 0.0386 | SREBF1 | −1.3262 | 0.0441 |
| ZNF99 | 1.3066 | 0.006 | SREBF2 | −1.3267 | 0.0052 |
| ZRANB2-AS2 | 2.7732 | 0.0247 | SRP19 | −1.1827 | 0.0348 |
| ZSCAN16-AS1 | 2.1246 | 0.0044 | SRP54 | −1.3084 | 0.0195 |
| ZSCAN26 | 1.365 | 0.0452 | SRP68 | −1.1633 | 0.0225 |
| ZSCAN9 | 1.5323 | 0.0108 | SRSF8 | −1.1536 | 0.0221 |
| | | | SRXN1 | −1.4536 | 0.0148 |
| | | | SSFA2 | −1.4279 | 0.0409 |
| | | | SSR1 | −1.4492 | 0.0362 |
| | | | SSSCA1-AS1 | −1.609 | 0.0034 |
| | | | STAMBP | −1.2636 | 0.0185 |
| | | | STAU1 | −1.185 | 0.0152 |
| | | | STAU2 | −1.3732 | 0.0332 |
| | | | STIL | −1.4101 | 0.0486 |
| | | | STIP1 | −1.3201 | 0.0236 |
| | | | STRIP1 | −1.1903 | 0.0026 |
| | | | STRN | −1.5182 | 0.0493 |
| | | | STRN3 | −1.4775 | 0.0095 |
| | | | STX6 | −1.2588 | 0.0154 |
| | | | STXBP5 | −1.5394 | 0.047 |
| | | | SUDS3P1 | −3.3601 | 0.0326 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| | | | SULT1D1P | −1.8151 | 0.0333 |
| | | | SUMO2 | −1.1855 | 0.0297 |
| | | | SUPT5H | −1.1473 | 0.0389 |
| | | | SURF4 | −1.2378 | 0.0404 |
| | | | SVIL-AS1 | −1.4477 | 0.0145 |
| | | | SYNRG | −1.4454 | 0.0091 |
| | | | TADA2B | −1.2514 | 0.0036 |
| | | | TAF13 | −1.6923 | 0.0132 |
| | | | TAF9BP1 | −2.3984 | 0.0326 |
| | | | TAGLN2P1 | −3.6756 | 0.047 |
| | | | TAOK1 | −1.4012 | 0.0255 |
| | | | TAOK2 | −1.1883 | 0.0359 |
| | | | TARDBP | −1.1427 | 0.0311 |
| | | | TARS | −1.5522 | 0.0042 |
| | | | TATDN2 | −1.2006 | 0.0391 |
| | | | TBC1D10B | −1.1986 | 0.0017 |
| | | | TBC1D22B | −1.2724 | 0.0193 |
| | | | TBC1D23 | −1.2895 | 0.021 |
| | | | TBCCD1 | −1.3255 | 0.0497 |
| | | | TBK1 | −1.2223 | 0.0291 |
| | | | TBX20 | −1.2923 | 0.0333 |
| | | | TCAIM | −1.1943 | 0.0147 |
| | | | TCEB3 | −1.382 | 0.0056 |
| | | | TCEB3C | −1.2916 | 0.0333 |
| | | | TDG | −1.3344 | 0.0138 |
| | | | TDP1 | −1.44 | 0.0062 |
| | | | TDRD7 | −1.4578 | 0.0249 |
| | | | TEFM | −1.3114 | 0.0363 |
| | | | TERF2 | −1.2927 | 0.0152 |
| | | | TERF2IP | −1.1288 | 0.0172 |
| | | | TEX10 | −1.3603 | 0.0047 |
| | | | TEX2 | −1.3928 | 0.0074 |
| | | | TFB2M | −1.339 | 0.0489 |
| | | | TFG | −1.2172 | 0.0342 |
| | | | TFIP11 | −1.1262 | 0.0319 |
| | | | THAP11 | −1.275 | 0.0235 |
| | | | THOC3 | −1.4478 | 0.0239 |
| | | | THUMPD3 | −1.2288 | 0.0462 |
| | | | THUMPD3P1 | −1.7593 | 0.0333 |
| | | | TICRR | −1.3291 | 0.0149 |
| | | | TIMM8A | −1.2687 | 0.0471 |
| | | | TLCD2 | −1.3537 | 0.0487 |
| | | | TLK2 | −1.1962 | 0.0409 |
| | | | TM4SF19-AS1 | −2.3133 | 0.0296 |
| | | | TM4SF5 | −2.1815 | 0.0333 |
| | | | TM9SF1 | −1.4646 | 0.0105 |
| | | | TM9SF3 | −1.1967 | 0.0378 |
| | | | TMBIM6 | −1.2151 | 0.0333 |
| | | | TMCC1 | −1.3143 | 0.0118 |
| | | | TMED10 | −1.2464 | 0.0381 |
| | | | TMED2 | −1.3218 | 0.0247 |
| | | | TMED7 | −1.3799 | 0.0457 |
| | | | TMED7-TICAM2 | −2.5706 | 0.0088 |
| | | | TMEFF1 | −2.7434 | 0.0352 |
| | | | TMEM123 | −1.3894 | 0.0471 |
| | | | TMEM127 | −1.3598 | 0.0066 |
| | | | TMEM135 | −1.3401 | 0.0103 |
| | | | TMEM154 | −1.5329 | 0.017 |
| | | | TMEM159 | −1.2218 | 0.0434 |
| | | | TMEM165 | −1.3299 | 0.0137 |
| | | | TMEM167A | −1.2226 | 0.0352 |
| | | | TMEM182 | −1.4498 | 0.0466 |
| | | | TMEM184C | −1.5243 | 0.0102 |
| | | | TMEM192 | −1.361 | 0.0355 |
| | | | TMEM206 | −1.4641 | 0.0239 |
| | | | TMEM229A | −5.604 | 0.0469 |
| | | | TMEM245 | −1.3366 | 0.0299 |
| | | | TMEM26 | −1.6027 | 0.0141 |
| | | | TMEM265 | −1.4767 | 0.0256 |
| | | | TMEM33 | −1.4475 | 0.0452 |
| | | | TMEM41A | −1.3408 | 0.0022 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| | | | TMEM45B | −1.4789 | 0.043 |
| | | | TMEM65 | −1.2048 | 0.0481 |
| | | | TMEM70 | −1.3988 | 0.0012 |
| | | | TMOD2 | −1.2859 | 0.0486 |
| | | | TMOD3 | −1.7146 | 0.0342 |
| | | | TMTC3 | −1.3465 | 0.0285 |
| | | | TMX1 | −1.3237 | 0.0463 |
| | | | TNFRSF1A | −1.2185 | 0.0392 |
| | | | TNKS1BP1 | −1.2718 | 0.0273 |
| | | | TNPO3 | −1.1697 | 0.0165 |
| | | | TNRC6B | −1.4265 | 0.0309 |
| | | | TOLLIP | −1.3487 | 0.0081 |
| | | | TOM1L1 | −1.3996 | 0.0216 |
| | | | TOMM70A | −1.2895 | 0.0297 |
| | | | TOP3A | −1.1316 | 0.022 |
| | | | TOR1A | −1.1571 | 0.0104 |
| | | | TOR1B | −1.2849 | 0.0035 |
| | | | TOX4 | −1.1866 | 0.0143 |
| | | | TP53RK | −1.3471 | 0.0004 |
| | | | TPI1P2 | −1.9364 | 0.0079 |
| | | | TPST2 | −1.2766 | 0.0478 |
| | | | TRAF3IP1 | −1.5373 | 0.0113 |
| | | | TRIB3 | −1.2949 | 0.033 |
| | | | TRIM15 | −1.711 | 0.0261 |
| | | | TRIM25 | −1.3681 | 0.0441 |
| | | | TRIM33 | −1.2885 | 0.049 |
| | | | TRIM69 | −1.6642 | 0.0144 |
| | | | TRIP11 | −1.4917 | 0.0063 |
| | | | TRIP12 | −1.4584 | 0.0105 |
| | | | TRMO | −1.1389 | 0.0452 |
| | | | TRMT10A | −1.3908 | 0.0296 |
| | | | TRMT1L | −1.4313 | 0.0179 |
| | | | TRMT44 | −1.348 | 0.0016 |
| | | | TROVE2 | −1.4897 | 0.0256 |
| | | | TSACC | −2.3487 | 0.0228 |
| | | | TSPYL1 | −1.3428 | 0.0436 |
| | | | TSR1 | −1.3022 | 0.037 |
| | | | TSSK5P | −3.7017 | 0.029 |
| | | | TTC1 | −1.234 | 0.0266 |
| | | | TTC5 | −1.3316 | 0.003 |
| | | | TTF2 | −1.2204 | 0.0384 |
| | | | TTI1 | −1.3347 | 0.0082 |
| | | | TTLL11 | −1.4254 | 0.0225 |
| | | | TTPAL | −1.3111 | 0.0184 |
| | | | TUBBP1 | −2.8856 | 0.0019 |
| | | | TUBG1 | −1.3208 | 0.0209 |
| | | | TXLNA | −1.2723 | 0.0182 |
| | | | TXNDC9 | −1.289 | 0.0165 |
| | | | TYRO3 | −1.7968 | 0.0299 |
| | | | UBAC2 | −1.1806 | 0.0259 |
| | | | UBAP2L | −1.1985 | 0.0401 |
| | | | UBE2A | −1.1732 | 0.0041 |
| | | | UBE2D3 | −1.184 | 0.035 |
| | | | UBE2E2 | −1.3847 | 0.0107 |
| | | | UBE2J1 | −1.2211 | 0.0321 |
| | | | UBE2K | −1.2077 | 0.0182 |
| | | | UBE2O | −1.1636 | 0.002 |
| | | | UBE2S | −1.3364 | 0.0448 |
| | | | UBE2W | −1.3192 | 0.0404 |
| | | | UBFD1 | −1.3648 | 0.0068 |
| | | | UBN1 | −1.2769 | 0.0091 |
| | | | UBQLN1 | −1.3497 | 0.0097 |
| | | | UBR3 | −1.3134 | 0.0344 |
| | | | UBTFL1 | −1.4161 | 0.0333 |
| | | | UBXN2A | −1.2039 | 0.0367 |
| | | | UCK1 | −1.1435 | 0.0025 |
| | | | UCK2 | −1.2526 | 0.0404 |
| | | | UEVLD | −1.3918 | 0.0199 |
| | | | UFSP2 | −1.2009 | 0.0155 |
| | | | UGDH | −1.5189 | 0.0309 |
| | | | UNC119B | −1.2989 | 0.0147 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| | | | UPF1 | −1.255 | 0.0132 |
| | | | UPF2 | −1.2881 | 0.0145 |
| | | | UQCRC2 | −1.2722 | 0.0308 |
| | | | UQCRFS1P1 | −1.4648 | 0.0055 |
| | | | URB1 | −1.4699 | 0.0075 |
| | | | URB2 | −1.5984 | 0.0377 |
| | | | URI1 | −1.3498 | 0.0232 |
| | | | USO1 | −1.2895 | 0.0051 |
| | | | USP10 | −1.4053 | 0.0176 |
| | | | USP14 | −1.366 | 0.0219 |
| | | | USP17L4 | −4.6197 | 0.0422 |
| | | | USP19 | −1.1296 | 0.0364 |
| | | | USP22 | −1.1513 | 0.0195 |
| | | | USP28 | −1.3227 | 0.044 |
| | | | USP38 | −1.6489 | 0.0287 |
| | | | USP47 | −1.2976 | 0.0386 |
| | | | USP7 | −1.2968 | 0.0124 |
| | | | USP8 | −1.4514 | 0.0262 |
| | | | UTP14C | −1.3596 | 0.0263 |
| | | | UTP18 | −1.3265 | 0.0247 |
| | | | UTP3 | −1.2066 | 0.0352 |
| | | | VAPA | −1.226 | 0.0477 |
| | | | VAPB | −1.2315 | 0.0042 |
| | | | VCP | −1.3125 | 0.0173 |
| | | | VDAC2P3 | −1.5375 | 0.0333 |
| | | | VHLL | −2.5044 | 0.032 |
| | | | VKORC1L1 | −1.2486 | 0.0065 |
| | | | VPS26B | −1.1088 | 0.0484 |
| | | | VPS35 | −1.3321 | 0.0289 |
| | | | VPS37A | −1.2773 | 0.044 |
| | | | VPS37C | −1.1968 | 0.005 |
| | | | VPS4B | −1.4152 | 0.0372 |
| | | | VPS50 | −1.2862 | 0.0213 |
| | | | VPS53 | −1.3958 | 0.0278 |
| | | | VTA1 | −1.3561 | 0.0319 |
| | | | VWA9 | −1.1694 | 0.0114 |
| | | | WAPL | −1.2858 | 0.0024 |
| | | | WASL | −1.2978 | 0.0356 |
| | | | WDFY3 | −1.2839 | 0.0498 |
| | | | WDR20 | −1.1959 | 0.0314 |
| | | | WDR3 | −1.8169 | 0.0257 |
| | | | WDR45B | −1.1702 | 0.0058 |
| | | | WDR82 | −1.2705 | 0.0337 |
| | | | WHAMM | −1.1365 | 0.0496 |
| | | | WI2-1959D15.1 | −1.0279 | 0.0212 |
| | | | WIPF2 | −1.257 | 0.0091 |
| | | | WNK3 | −1.7117 | 0.0079 |
| | | | WRBP1 | −1.9659 | 0.0333 |
| | | | WSB2 | −1.1549 | 0.0267 |
| | | | WWTR1 | −1.4248 | 0.0408 |
| | | | XBP1 | −1.345 | 0.027 |
| | | | XIAP | −1.3181 | 0.0294 |
| | | | XKR6 | −1.6196 | 0.0111 |
| | | | XPNPEP3 | −1.2873 | 0.0159 |
| | | | XPO5 | −1.3132 | 0.0005 |
| | | | XPO7 | −1.2357 | 0.0029 |
| | | | XPOT | −1.2652 | 0.003 |
| | | | XXbac-BPG248L24.12 | −5.1783 | 0.0034 |
| | | | YKT6 | −1.2517 | 0.0207 |
| | | | YLPM1 | −1.1935 | 0.0268 |
| | | | YME1L1 | −1.3738 | 0.0323 |
| | | | YTHDF2 | −1.2094 | 0.0308 |
| | | | YTHDF3 | −1.3477 | 0.0313 |
| | | | Z99756.1 | −1.4786 | 0.0333 |
| | | | ZBED4 | −1.415 | 0.0081 |
| | | | ZBTB11-AS1 | −1.2613 | 0.0402 |
| | | | ZBTB45 | −1.1957 | 0.0288 |
| | | | ZBTB45P1 | −18.0353 | 0.001 |
| | | | ZBTB7A | −1.4301 | 0.0219 |
| | | | ZC3H14 | −1.2598 | 0.0351 |
| | | | ZC3H15 | −1.2146 | 0.0208 |

TABLE 10-continued

Differentially Expressed Genes in the Skin Biopsies of Responders Compared to Non-Responders

| Up-regulated in Responders vs. Non-Responders | | | Down-regulated in Responders vs. Non-Responders | | |
|---|---|---|---|---|---|
| Gene Symbol | Fold Change | Raw P Value | Gene Symbol | Fold Change | Raw P Value |
| | | | ZC3H18 | −1.3222 | 0.0253 |
| | | | ZC3HAV1 | −1.3438 | 0.0446 |
| | | | ZCCHC17 | −1.1747 | 0.0467 |
| | | | ZDHHC5 | −1.3768 | 0.0066 |
| | | | ZFAND4 | −1.2911 | 0.0167 |
| | | | ZFHX2 | −1.4127 | 0.0382 |
| | | | ZFP41 | −1.406 | 0.0219 |
| | | | ZFP64 | −1.2749 | 0.0354 |
| | | | ZFP69B | −1.669 | 0.0311 |
| | | | ZHX1 | −1.6142 | 0.0259 |
| | | | ZNF106 | −1.3599 | 0.0204 |
| | | | ZNF131 | −1.243 | 0.0151 |
| | | | ZNF24 | −1.1589 | 0.0078 |
| | | | ZNF252P | −1.5435 | 0.0187 |
| | | | ZNF268 | −1.3352 | 0.0126 |
| | | | ZNF346 | −1.2897 | 0.0064 |
| | | | ZNF410 | −1.1952 | 0.008 |
| | | | ZNF518B | −1.5166 | 0.0163 |
| | | | ZNF609 | −1.3513 | 0.0105 |
| | | | ZNF622 | −1.1906 | 0.0212 |
| | | | ZNF623 | −1.3455 | 0.0412 |
| | | | ZNF670-ZNF695 | −2.0431 | 0.0402 |
| | | | ZNF672 | −1.1539 | 0.0285 |
| | | | ZNF770 | −2.0284 | 0.0444 |
| | | | ZNF778 | −1.5494 | 0.0027 |
| | | | ZNHIT2 | −1.2778 | 0.0302 |
| | | | ZW10 | −1.3804 | 0.0063 |
| | | | ZYG11B | −1.2478 | 0.0139 |

Example 5: Identification of Gene Combinations that Predict Responsiveness to Treatment with Ruxolitinib Robust drug response genomic signatures were identified by selecting biomarkers and building prediction models from the baseline RNA-Seq data in Example 1. Starting with the biomarker candidates listed in Table 8, the genes were ranked based on information gain and biological relevance and then the top genes were plugged into the support vector machine algorithm to train classification models. Performance of the models were assessed by leave-one-out cross validation.

Information gain is the amount of information that is gained by knowing the value of the attribute (gene), which is the entropy of the distribution before the split minus the entropy of the distribution after it. The largest information gain is equivalent to the smallest entropy.

Support vector machine (SVM) is a widely used supervised learning algorithm in data mining. In this algorithm, each sample in the data set is plotted as a point in n-dimensional space (where n is number of attributes (genes)) with the value of each attribute being the value of a particular coordinate. Then, classification is performed by finding a separating hyper-plane that differentiate the two classes very well.

Cross validation is a standard way in data mining to measure the performance of a model during training process. Leave-one-out cross validation (LOOCV) uses a single sample from the original data set as the validation data, and the remaining samples as the training data. This is repeated such that each sample in the data set is used once as the validation data.

Second, all candidate markers in Table 8 were evaluated with baseline RNA-Seq data from both Example 1 (Day 28 therapeutic response) and Example 4 (Day 84 therapeutic response) by calculating the information gain of each gene, then selecting six genes among which three (BZW1P2, HTR1F, TMED7-TICAM2) have the top overall information gain and another three (CCL18, IL1RAPL2, PRSS30P) are disease related markers with the best information gain. An SVM model built on the expression level of these six genes yields perfect classification (no mistake) on samples from both data sets. Three genes, IL1RAPL2, PRSS30P and HTR1F are up-regulated while another three CCL18, BZW1P2, and TMED7-TICAM2 are down-regulated in the responder group.

Third, similar to the previous exercise, all candidate markers in Table 8 were evaluated with baseline RNA-Seq data from both Example 1 and Example 4 (Day28 therapeutic response). An SVM model built on nine genes with the best information gain yields perfect prediction on all samples. Among these genes, two (CCL18, IL1RAPL2) are disease biomarkers, seven (FSIP2, H1FNT, HTR1F, IL1RAPL2, PTPN5, RBP3, and WDR88) are up-regulated while two (CCL18, PLA2G2D) are down-regulated in the responder group.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject having an inflammatory skin disease selected from psoriasis, atopic dermatitis, vitiligo, hidradenitis suppurativa, rosacea, Lichen planus, generalized pustular psoriasis, palmoplantar pustulosis, acne, cutaneous lupus, and dermatomyositis comprising administering to the human subject a JAK1 inhibitor, wherein the human subject has been previously determined to have (i) a baseline expression level of a gene, which is CCL18, in a biological sample obtained from the human subject that is lower than a control, wherein the control is the expression level of the gene CCL18 in a sample or samples obtained from one or more subjects that have not responded to treatment with the JAK1 inhibitor, and/or (ii) a baseline expression level of a gene, which is IL1RAPL2, in a biological sample obtained from the human subject that is higher than a control, wherein the control is the expression level of the gene IL1RAPL2 in a sample or samples obtained from one or more subjects that have not responded to treatment with the JAK1 inhibitor, wherein the JAK1 inhibitor is:
ruxolitinib,
itacitinib, or
4-[3-(cyanomethyl)-3-(3',5'-dimethyl-1H,1'H-4,4'-bi-pyrazol-1-yl)azetidin-1-yl]-2,5-difluoro-N-[(1S)-2,2,2-trifluoro-1-methylethyl]benzamide,
or a pharmaceutically acceptable salt of any of the aforementioned.

2. The method of claim 1, wherein the human subject has been previously determined to have (i) baseline expression levels of the genes CCL18 and PLA2G2D in a biological sample obtained from the human subject that are lower than controls, wherein the controls are the expression levels of the genes CCL18 and PLA2G2D in a sample or samples obtained from one or more subjects that have not responded to treatment with the JAK1 inhibitor, and (ii) baseline expression levels of the genes FSIP2, H1FNT, HTR1F, IL1RAPL2, PTPN5, RBP3, and WDR88 in a biological sample obtained from the human subject that are higher than controls, wherein the controls are the expression levels of the genes FSIP2, H1FNT, HTR1F, IL1RAPL2, PTPN5, RBP3, and WDR88 in a sample or samples obtained from one or more subjects that have not responded to treatment with the JAK1 inhibitor.

3. A method of treating a human subject having an inflammatory skin disease selected from psoriasis, atopic dermatitis, vitiligo, hidradenitis suppurativa, rosacea, Lichen planus, generalized pustular psoriasis, palmoplantar pustulosis, acne, cutaneous lupus, and dermatomyositis, comprising:
providing a biological sample obtained from the human subject;
measuring in the biological sample a reduced expression level, as compared to a control, of a gene, which is CCL18, wherein the control is the expression level of the CCL18 gene in a sample or samples obtained from one or more subjects that have not responded to treatment with the JAK1 inhibitor, and/or an increased expression level, as compared to a control, of a gene, which is IL1RAPL2, wherein the control is the expression level of the IL1RAPL2 gene in a sample or samples obtained from one or more subjects that have not responded to treatment with the JAK1 inhibitor; and
administering a therapy comprising a JAK1 inhibitor to the human subject, wherein the JAK1 inhibitor is:
ruxolitinib,
itacitinib, or
4-[3-(cyanomethyl)-3-(3',5'-dimethyl-1H,1'H-4,4'-bi-pyrazol-1-yl)azetidin-1-yl]-2,5-difluoro-N-[(1S)-2,2,2-trifluoro-1-methylethyl]benzamide,
or a pharmaceutically acceptable salt of any of the aforementioned.

4. The method of claim 3, comprising measuring in the biological sample reduced expression levels, as compared to controls, of the genes CCL18 and PLA2G2D, wherein the controls are the expression levels of the genes CCL18 and PLA2G2D in a sample or samples obtained from one or more subjects that have not responded to treatment with the JAK1 inhibitor, and increased expression levels, as compared to controls, of the genes FSIP2, H1FNT, HTR1F, IL1RAPL2, PTPN5, RBP3, and WDR88, wherein the controls are the expression levels of the genes FSIP2, H1FNT, HTR1F, IL1RAPL2, PTPN5, RBP3, and WDR88 in a sample or samples obtained from one or more subjects that have not responded to treatment with the JAK1 inhibitor.

5. The method of claim 1, wherein the JAK1 inhibitor is topically administered to the human subject.

6. The method of claim 1, wherein the expression levels of no more than 20 genes are measured.

7. The method of claim 1, wherein the expression levels of no more than 10 genes are measured.

8. The method of claim 1, wherein the biological sample comprises a skin biopsy.

9. The method of claim 8, wherein the skin biopsy is obtained by use of a non-invasive tape strip, an adhesive patch, a dermal shaving, or a skin microplanning.

10. The method of claim 1, wherein the expression level of the gene is measured by RNA sequencing or quantitative PCR.

11. The method of claim 1, wherein the human subject has been previously determined to have a baseline expression level of the gene PLA2G2D in a biological sample obtained from the human subject that is lower than a control, wherein the control is the expression level of the gene PLA2G2D in a sample or samples obtained from one or more subjects that have not responded to treatment with the JAK1 inhibitor.

12. The method of claim 1, wherein the human subject has been previously determined to have a baseline expression level of the gene FSIP2 in a biological sample obtained from the human subject that is higher than a control, wherein the control is the expression level of the gene FSIP2 in a sample or samples obtained from one or more subjects that have not responded to treatment with the JAK1 inhibitor.

13. The method of claim 1, wherein the human subject has been previously determined to have a baseline expression level of the gene H1FNT in a biological sample obtained from the human subject that is higher than a control, wherein the control is the expression level of the gene H1FNT in a sample or samples obtained from one or more subjects that have not responded to treatment with the JAK1 inhibitor.

14. The method of claim 1, wherein the human subject has been previously determined to have a baseline expression level of the gene HTR1F in a biological sample obtained from the human subject that is higher than a control, wherein the control is the expression level of the gene HTR1F in a sample or samples obtained from one or more subjects that have not responded to treatment with the JAK1 inhibitor.

15. The method of claim 1, wherein the human subject has been previously determined to have a baseline expression level of the gene PTPN5 in a biological sample obtained from the human subject that is higher than a control, wherein the control is the expression level of the gene PTPN5 in a sample or samples obtained from one or more subjects that have not responded to treatment with the JAK1 inhibitor.

16. The method of claim 1, wherein the human subject has been previously determined to have a baseline expression level of the gene RBP3 in a biological sample obtained from the human subject that is higher than a control, wherein the control is the expression level of the gene RBP3 in a sample or samples obtained from one or more subjects that have not responded to treatment with the JAK1 inhibitor.

17. The method of claim 1, wherein the human subject has been previously determined to have a baseline expression level of the gene WDR88 in a biological sample obtained from the human subject that is higher than a control, wherein the control is the expression level of the gene WDR88 in a sample or samples obtained from one or more subjects that have not responded to treatment with the JAK1 inhibitor.

18. The method of claim 1, wherein the JAK1 inhibitor is ruxolitinib or a pharmaceutically acceptable salt thereof.

19. The method of claim 1, wherein the JAK1 inhibitor is itacitinib or a pharmaceutically acceptable salt thereof.

20. The method of claim 1, wherein the JAK1 inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide or a pharmaceutically acceptable salt thereof.

21. The method of claim 3, wherein the JAK1 inhibitor is topically administered to the human subject.

22. The method of claim 3, wherein the expression levels of no more than 20 genes are measured.

23. The method of claim 3, wherein the expression levels of no more than 10 genes are measured.

24. The method of claim 3, wherein the biological sample comprises a skin biopsy.

25. The method of claim 24, wherein the skin biopsy was obtained by use of a non-invasive tape strip, an adhesive patch, a dermal shaving, or a skin microplanning.

26. The method of claim 3, wherein the expression level of the gene is measured by RNA sequencing or quantitative PCR.

27. The method of claim 3, comprising measuring in the biological sample a reduced baseline expression level of the gene PLA2G2D, as compared to a control, wherein the control is the expression level of the gene PLA2G2D in a sample or samples obtained from one or more subjects that have not responded to treatment with the JAK1 inhibitor.

28. The method of claim 3, comprising measuring in the biological sample an increased baseline expression level of the gene FSIP2, as compared to a control, wherein the control is the expression level of the gene FSIP2 in a sample or samples obtained from one or more subjects that have not responded to treatment with the JAK1 inhibitor.

29. The method of claim 3, comprising measuring in the biological sample an increased baseline expression level of the gene H1FNT, as compared to a control, wherein the control is the expression level of the gene H1FNT in a sample or samples obtained from one or more subjects that have not responded to treatment with the JAK1 inhibitor.

30. The method of claim 3, comprising measuring in the biological sample an increased baseline expression level of the gene HTR1F, as compared to a control, wherein the control is the expression level of the gene HTR1F in a sample or samples obtained from one or more subjects that have not responded to treatment with the JAK1 inhibitor.

31. The method of claim 3, comprising measuring in the biological sample an increased baseline expression level of the gene PTPN5, as compared to a control, wherein the control is the expression level of the gene PTPN5 in a sample or samples obtained from one or more subjects that have not responded to treatment with the JAK1 inhibitor.

32. The method of claim 3, comprising measuring in the biological sample an increased baseline expression level of the gene RBP3, as compared to a control, wherein the control is the expression level of the gene RBP3 in a sample or samples obtained from one or more subjects that have not responded to treatment with the JAK1 inhibitor.

33. The method of claim 3, comprising measuring in the biological sample an increased baseline expression level of the gene WDR88, as compared to a control, wherein the control is the expression level of the gene WDR88 in a sample or samples obtained from one or more subjects that have not responded to treatment with the JAK1 inhibitor.

34. The method of claim 3, wherein the JAK1 inhibitor is ruxolitinib or a pharmaceutically acceptable salt thereof.

35. The method of claim 3, wherein the JAK1 inhibitor is itacitinib or a pharmaceutically acceptable salt thereof.

36. The method of claim 3, wherein the JAK1 inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro methylethyl]benzamide or a pharmaceutically acceptable salt thereof.

* * * * *

UNITED STATES PATENT AND TRADEMARK OFFICE
CERTIFICATE OF CORRECTION

PATENT NO. : 11,584,961 B2  
APPLICATION NO. : 16/369724  
DATED : February 21, 2023  
INVENTOR(S) : Howell et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 351 days.

Signed and Sealed this  
Sixth Day of February, 2024

Katherine Kelly Vidal  
*Director of the United States Patent and Trademark Office*